(12) United States Patent
Pardon et al.

(10) Patent No.: US 9,518,084 B2
(45) Date of Patent: Dec. 13, 2016

(54) EPITOPE TAG FOR AFFINITY-BASED APPLICATIONS

(75) Inventors: Els Pardon, Lubbeek (BE); Jan Steyaert, Beersel (BE); Lode Wyns, Antwerp (BE)

(73) Assignees: VIB VZW, Gent (BE); Vrije Universiteit Brussel, Brussels (BE)

( * ) Notice: Subject to any disclaimer, the term of this patent is extended or adjusted under 35 U.S.C. 154(b) by 993 days.

(21) Appl. No.: 13/698,624

(22) PCT Filed: May 25, 2011

(86) PCT No.: PCT/EP2011/058591
§ 371 (c)(1),
(2), (4) Date: Jan. 17, 2013

(87) PCT Pub. No.: WO2011/147890
PCT Pub. Date: Dec. 1, 2011

(65) Prior Publication Data
US 2013/0115635 A1    May 9, 2013

(30) Foreign Application Priority Data
May 25, 2010 (GB) .................................. 1008682.5

(51) Int. Cl.
C07K 5/113 (2006.01)
C07K 1/22 (2006.01)

(52) U.S. Cl.
CPC ............... *C07K 5/1021* (2013.01); *C07K 1/22* (2013.01); *C07K 2319/40* (2013.01)

(58) Field of Classification Search
CPC ...... C07K 5/1021; C07K 1/22; C07K 2319/40
See application file for complete search history.

(56) References Cited

U.S. PATENT DOCUMENTS 5,716,854 A * 2/1998 Löfås et al. ..... G01N 33/54373
435/7.92
2003/0219854 A1   11/2003 Guarna et al.
2004/0001827 A1   1/2004 Dennis
2004/0096444 A1   5/2004 Pizzo et al.
2005/0287153 A1   12/2005 Dennis
2006/0259986 A1   11/2006 Chilcote et al.
2007/0020264 A1   1/2007 Dennis
2009/0035217 A1   2/2009 Chilcote et al.
2010/0104588 A1   4/2010 Dennis

FOREIGN PATENT DOCUMENTS

| WO | WO95/10532 | * | 4/1995 | ............ C07K 5/093 |
|---|---|---|---|---|
| WO | WO 95/10532 A1 | | 4/1995 | |
| WO | WO97/22706 | | 6/1997 | |
| WO | WO98/28429 | | 7/1998 | |
| WO | WO 2004/016230 A2 | | 2/2004 | |
| WO | WO 2006/ 020581 A2 | * | 2/2006 | ............ A61K 39/00 |
| WO | WO 2006/045037 A2 | | 4/2006 | |
| WO | WO 2010/022980 A1 | * | 3/2010 | .......... G01N 33/543 |
| WO | WO 2011/147890 A1 | | 12/2011 | |

OTHER PUBLICATIONS

Vuchelen et al., H-1, C-13 and N-15 assignments of a camelid nanobody directed against human alpha-synuclean, Biomolecular NMR Assignments, Dec. 2009, pp. 231-233, vol. 3, No. 2.
Yonemoto et al. A General strategy for the bacterial expression of amyloidogenic peptides using BCL-XL-1/2 fusions, Protein Science, Sep. 2009, pp. 1978-1986, vol. 18, No. 9.
De Genst et al., Structure and Properties of a Complex of alpha-Synuclein and a Single Domain Camelid Antibody, Journal of Molecular Biology, Sep. 17, 2010, pp. 326-343, vol. 402, No. 2, London, GB.
PCT International Search Report, PCT/EP2011/058591 Dated Aug. 22, 2011.

* cited by examiner

*Primary Examiner* — Christine Foster
(74) *Attorney, Agent, or Firm* — TraskBritt, P.C.

(57) ABSTRACT

Described is an epitope tag useful in affinity-based applications. The invention further includes fusion proteins, methods for preparing fusion proteins, nucleic acid molecules encoding these fusion proteins and recombinant host cells that contain these nucleic acid molecules. The invention also relates to nanobodies and other affinity ligands specifically recognizing the epitope tag, and uses thereof in affinity-based applications.

6 Claims, 10 Drawing Sheets
(8 of 10 Drawing Sheet(s) Filed in Color)

```
                         --CDR1--                    --CDR2---
Nb_85       qvqlqesgggsvqaggslrlscaas gltysnyc mgwfrqapgkarevvar istr-gikt yyadsvngrf
Nb_88       qvqlqesggglvqpggslrlscaas gytysric mgwfrqapgkarevvar istr-gikt yyadsvngrf
Nb_Syn2     qgqlvesgggsvqaggslrlscaas gidsssyc mgwfrqrpgkeregvar inglggvkt ayadsvkdrf
Nb_Syn2 PstI qvqlqesgggsvqaggslrlscaas gidsssyc mgwfrqrpgkeregvar inglggvkt ayadsvkdrf
Nb_Syn1a    evqlvesgggsvqaggslslacaps glnassyc mgwfrqspgkeregvar ingnagikt ayadsvkdrf
Nb_Syn1b    dvqlvesgggsvqaggslrlscaps glnassyc mgwfrqspgkeregvar ingnagikt ayadsvkdrf
Nb_Syn1c    qvqlvesgggsvqaggslrlscapl glnassyc mgwfrqspgkeregvar ingnagikt ayadsvkdrf
Nb_86       qvqlqesgggsvqaggslrlscals gytfrgnr mawfrqapgkeregvar intg-gvnt yvadsvkgrf
Nb_87       qvqlqesgggsvqtggslrlscvas gys---gy mawfrqapgkeregiaa iyrg-dkit yyahsvqgrf --------CDR3---------
Nb_85       tisrdnaknmvylqmnslkpedtaiyyc aaviypgygdscpwttsvny wgqgtqvtvss (SEQ ID NO:18)
Nb_88       tisrdnaknmvylqmnslkpedtaiyyc aaviypgygdscpwttsvny wgqgtqvtvss (SEQ ID NO:19)
Nb_Syn2     tisrdnaentvylqmnslkpedtaiyyc aakfspgyc--ggswsnfgy wgqgtqvtvss (SEQ ID NO:21)
Nb_Syn2 qvq tisrdnaentvylqmnslkpedtaiyyc aakfspgyc--ggswsnfgy wgqgtqvtvss (SEQ ID NO:20)
Nb_Syn1a    tlsrdnakntvylqmnslkaedsaiyfc aaksspgyc--ggnwdnfgy wgqgtqvtvss (SEQ ID NO:24)
Nb_Syn1b    tlsrdnakntvylqmnslkaedsamyyc aaksspgyc--ggnwdnfgy wgqgtqvtvss (SEQ ID NO:22)
Nb_Syn1c    tlsrdnakntvylqmnslkaedsamyyc aaksspgyc--ggnwdnfgy wgqgtqvtvss (SEQ ID NO:23)
Nb_86       tisqdnakntvylqmnnlqpedtamyfc aadltgwrp---vgfsgyny wgqgtqvtvss (SEQ ID NO:25)
Nb_87       tisqanakntvyllmnslkpedtaiyyc aarrvvadp--sllsktyay wgqgtqvtvss (SEQ ID NO:26)
```

*FIG. 1*

EPITOPE TAG FOR AFFINITY-BASED APPLICATIONS

CROSS-REFERENCE TO RELATED APPLICATIONS

This is a national phase entry under 35 U.S.C. §371 of International Patent Application PCT/EP2011/058591, filed May 25, 2011, published in English as International Patent Publication WO 2011/147890 A1 on Dec. 1, 2011, which claims the benefit under Article 8 of the Patent Cooperation Treaty to Great Britain Patent Application Serial No. 1008682.5, filed May 25, 2010.

TECHNICAL FIELD

The disclosure relates to an epitope tag useful in affinity-based applications. The disclosure further includes fusion proteins, methods for preparing fusion proteins, nucleic acid molecules encoding these fusion proteins, and recombinant host cells that contain these nucleic acid molecules. The disclosure also relates to nanobodies and other affinity ligands specifically recognizing the epitope tag, and uses thereof in affinity-based applications.

BACKGROUND

Epitope tagging is a technique in which a known epitope tag (typically 6 to 30 amino acids) is fused to a recombinant protein by placing sequence encoding the epitope within the same open reading frame of the protein by means of genetic engineering. By choosing an epitope tag for which an antibody is available, the technique makes it possible to detect tagged proteins for which no antibody is available. By selection of the appropriate epitope tag and antibody pair, it is possible to find a combination with properties that are suitable for the desired experimental application, such as Western blot analysis, immunoprecipitation, immunochemistry, and affinity purification, amongst others.

The first commercially available tags were originally designed for protein purification. Examples of these early commercial products include FLAG, 6xHis, and glutathione-S-transferase (GST) systems. The FLAG tagging system in its original version included the anti-FLAG M1 monoclonal antibody with calcium-dependent binding. FLAG-tagged proteins can be eluted from the M1 antibody with EDTA (Hopp et al. 1988). Likewise, the 6xHis tag is used for purification of recombinant proteins by means of metal chelate chromatography (Hochuli et al. 1988). Similarly, GST-tagged proteins can be purified using glutathione agarose (Smith et al. 1988). In addition to the commercial tags, the development of other tags such as HA (Field et al. 1988) and c-myc (Evan et al. 1985) were reported. As research progressed and recombinant DNA technology evolved, the utility of epitope tags in the study of protein interaction was recognized. For example, the anti-FLAG M2 monoclonal antibody was made available commercially (Brizzard et al. 1994) as were monoclonal antibodies for the 6xHis tag (Kaufmann et al. 2002), HA tag, and c-myc tag. Today, there are numerous types of tags with different features suited to diverse applications (Jarvik and Telmer 1998).

In addition to the traditional antibody and epitope combinations, other types of epitope tags have been discovered. An early example is the protein A tag, which binds to IgG (Uhlén et al. 1983). Other examples include those based on interaction with streptavidin (Schmidt and Skerra 2007) and biotin (Tucker and Grisshammer 1996), maltose-binding peptide (MBP tag) and maltose (di Guan et al. 1988), chitin-binding domain (CBD) and chitin (Chong et al. 1997), and the calmodulin-binding peptide that binds to calmodulin (Rigaut et al. 1999). Another type of tag is the S-peptide tag that binds to the S-protein derived from pancreatic RNAse A (Hackbarth et al. 2004).

Further advancements in the field are the use of multiple epitope tags to increase signal strength and signal-to-noise ratio, e.g., multiple copies of FLAG, His, c-myc and HA tags, or the use of tandem copies of different tags. For example, in tandem affinity purification (TAP), used for the study of protein networks, an IgG-binding domain and calmodulin-binding peptide with an intervening tobacco etch virus (TEV) protease cleavage site are used (Rigaut et al. 1999). Recently, a shorter TAP tag has been described, the SF-TAP tag (Gloeckner et al. 2007), in which two tandem copies of the Strep-tag II were combined with the FLAG tag.

While the use of epitope-tagging facilitates the study and characterization of newly discovered proteins, the technique does have limitations. The insertion of (an) epitope tag(s) can alter protein function, especially when a large tag is used (e.g., GST and MBP tag). Notably, the relatively short epitope tags, such as FLAG, rarely affect the properties of the heterologous protein of interest and are very specific for their respective primary antibodies. However, antibody affinity chromatography often involves low or high pH elution, which can irreversibly affect the properties of the fusion protein. It also employs resin, which has limited reusability. Poly-Histidine, typically in the form of a hexa-His tag, appended to the N- or C-terminus of a recombinant polypeptide, has been widely used to purify recombinant proteins using immobilized metal ion chromatography (IMAC). However, only moderate purity from *Escherichia coli* extracts and relatively poor purification from yeast, *Drosophila* and HeLa extracts are retrieved using a (His)6 tag (Lichty et al. 2005). Also, aspecific binding of contaminating proteins (e.g., *E. coli* SlyD, a prolyl isomerase) is often observed in IMAC preparations of heterologously expressed (His)6-tagged proteins, due to histidine clusters or intrinsic metal binding sites on these proteins. Further, few of the tags that have been described in literature have been tested in a high-throughput context. Peptide epitopes like the FLAG-tag, the calmodulin-binding peptide, the Strep-tag or Streptag II and the biotin acceptor peptide all exhibit a high degree of specificity for their cognate binding partners. However, the resins (immobilized proteins) that they interact with tend to be expensive, are easily fouled and have relatively low binding capacities, making them less than ideal for high-throughput applications. Several other advantages and limitations of epitope tagging are listed in Jarvik and Telmer (1998), Kimple and Sondek (2004), Waugh (2005), and Brizzard (2008).

Given that epitope tagging has the potential to make major contributions to the emerging fields of functional genomics and proteomics, there remains a need for alternative epitope tags. Indeed, future applications in these fields will increasingly depend on the separate tagging of individual proteins, requiring multiple epitope tags that can be used in combination.

DISCLOSURE

Proteins do not naturally lend themselves to high-throughput analysis because of their diverse physiochemical properties. Consequently, epitope tags have become indispensable tools for structural and functional proteomics initiatives. High-throughput protein production and analysis must, almost by definition, entail a generic strategy for purification. This is obviously a key attribute of epitope tags.

The small four-amino acid tag of the disclosure provides a good alternative for the His tag and other peptide tags that can be engineered into recombinant proteins. In particular, the C-terminal EPEA-tag (SEQ ID NO:1) is short and is specifically recognized by a small single-domain antibody fragment that can be immobilized to produce effective affinity resins to be used in the purification of tagged proteins. As exemplified further, the EPEA-tag (SEQ ID NO:1) can also be used for the visualization/identification of tagged proteins (ELISA, Western blot), for the copurification of protein complexes (Tap-tag applications), for (in vivo) imaging, for localizing the protein in the cell, for identifying interactions with other proteins/determining subunit structure, for determining the function of the protein and how it responds to changes in cell conditions, for determining what happens to the protein during the lifetime of the cell, for characterizing new proteins derived from cloned genes, and many others.

In a first aspect, the epitope tag consists of a four-amino acid sequence, the sequence defined by EPEA (SEQ ID NO:1), or by an amino acid sequence that has at least 75% sequence identity with SEQ ID NO:1, or by an amino acid sequence wherein at least 50% or 75% of the amino acids have been substituted by a conservative amino acid.

In one embodiment, disclosed is a non-naturally occurring fusion protein comprising the epitope tag hereof and a target protein. Herein, the epitope tag is directly coupled to the C-terminal end of the target protein or via a linker.

In a further embodiment, disclosed is an isolated nucleic acid sequence encoding the above-described epitope tag or fusion protein. A vector comprising the above nucleic acid sequence and a host cell comprising the vector or the nucleic acid sequence also forms part hereof.

In a further aspect, the disclosure relates to an affinity ligand specifically binding to the above-described epitope tag. In particular, the affinity ligand can be an antibody or an antibody fragment or a Nanobody™. In specific embodiments, disclosed is an isolated nucleic acid sequence encoding the herein-described affinity ligands, as well as a vector comprising such a nucleic acid sequence and a host cell comprising the vector or the nucleic acid sequence.

In a further aspect, the disclosure relates to a complex of (i) an affinity ligand as described herein, and (ii) a non-naturally occurring fusion protein as described herein, and (iii) optionally a ligand bound to the target protein comprised in the non-naturally occurring fusion protein. The complex may be crystalline.

In another aspect, disclosed is the use of the above epitope tag and/or the affinity ligand and/or the complex for affinity-based applications, such as affinity chromatography, affinity purification, immunoprecipitation, in vivo imaging, tandem affinity purification, protein detection, immunochemistry, surface-display, FRET-type applications, and co-crystallization. Protein detection can be performed in an ELISA detection assay or Western blot analysis. Affinity purification can be performed on a column or on beads.

Disclosed is a method for purifying a non-naturally occurring fusion protein comprising the steps of:
a) applying a solution containing a non-naturally occurring fusion protein as described herein to a solid support possessing an immobilized affinity ligand as described herein;
b) forming a complex between the immobilized affinity ligand and the fusion protein;
c) removing weakly bound or unbound molecules; and
d) eluting the bound molecules.

Also disclosed is a method for immobilizing and/or capturing a non-naturally occurring fusion protein on a solid support comprising the steps of:
a) applying a solution containing a non-naturally occurring fusion protein to a solid support possessing an immobilized affinity ligand as described herein;
b) forming a complex between the immobilized affinity ligand and the fusion protein; and
c) removing weakly bound or unbound molecules.

Another aspect hereof is a method for detecting a non-naturally occurring fusion protein in a sample by using the affinity ligand.

Also provided is a kit comprising an epitope tag as described herein, and/or a non-naturally occurring fusion protein as described herein, and/or a nucleic acid sequence as described herein, and/or a vector as described herein, and/or an affinity ligand as described herein and/or a complex as described herein. The kit may be used for affinity-based applications, such as affinity chromatography, affinity purification, immunoprecipitation, in vivo imaging, tandem affinity purification, protein detection, immunochemistry, surface-display, FRET-type applications, or co-crystallization.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1: Amino acid sequences of the different nanobodies that specifically bind to α-synuclein.

DETAILED DESCRIPTION

Figure 2A:
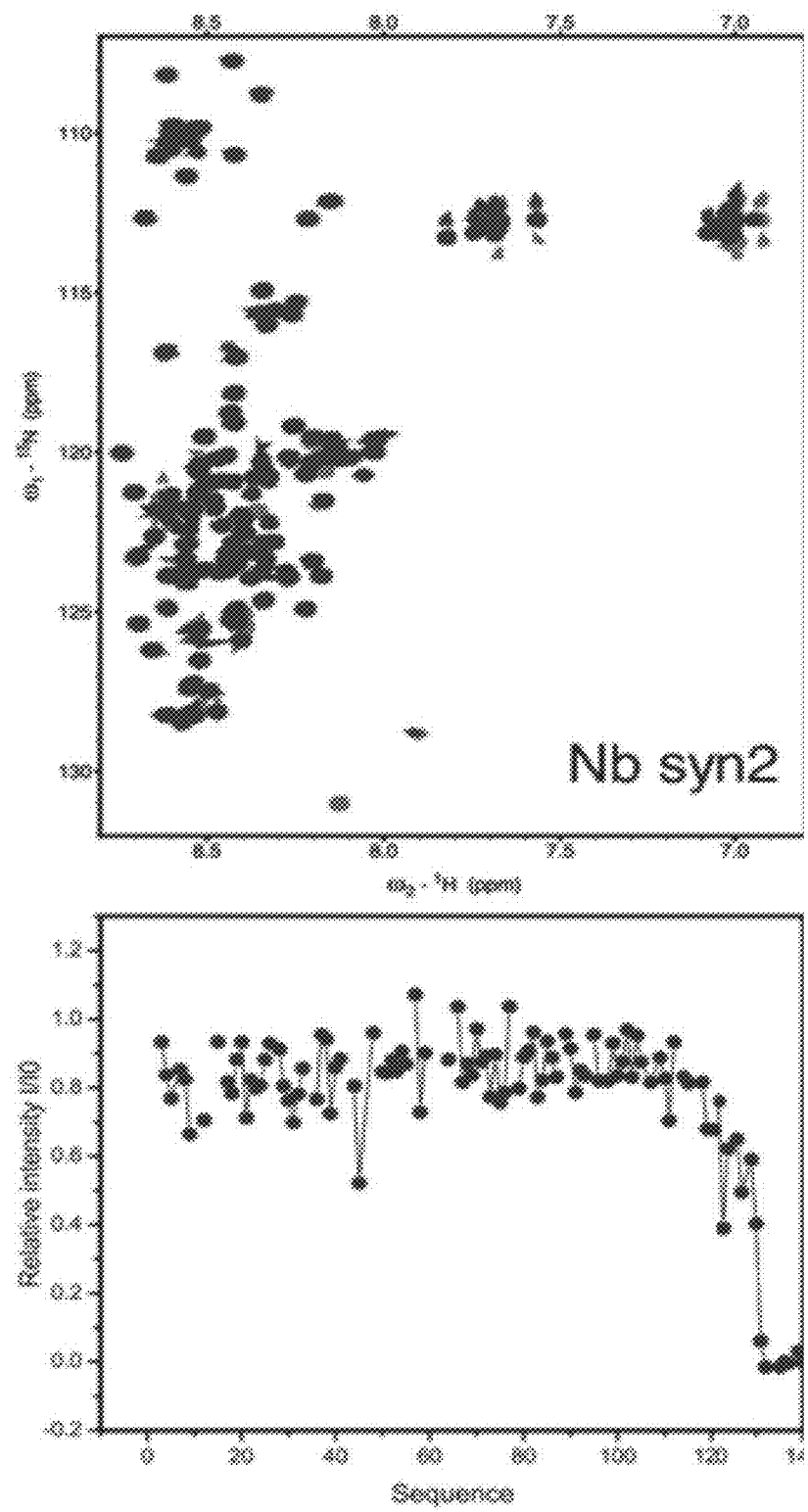
FIGS. 2A-2C: Analysis of the interactions between α-synuclein and a series of α-synuclein-specific Nanobodies™ by Chemical Shift Mapping using NMR spectroscopy. The top panel represents the HSQC spectra of $N^{15}$-labeled α-synuclein obtained in the absence (red) and the presence (blue) of one equivalent of Nbsyn2, Nb85 or Nb87. The bottom panel represents the relative intensity changes upon binding of the different Nanobodies™. Relative intensities ($I/I_0$) were calculated for each amino acid from the proton-nitrogen cross-peaks of free α-synuclein ($I_0$) and Nanobody™ bound α-synuclein (I) and plotted against the residue numbers.

The disclosure will be described with respect to particular embodiments and with reference to certain drawings, the invention not being limited thereto, but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun, e.g., "a," "an," or "the," this includes a plural of that noun unless something else is specifically stated. Furthermore, the terms "first," "second," "third," and the like, in the description and in the claims, are used for distinguishing between similar elements and not necessarily for describing a sequential or chronological order. It is to be understood that the terms so used are interchangeable under appropriate circumstances and that the embodiments hereof described herein are capable of operation in sequences other than described or illustrated herein.

Unless otherwise defined herein, scientific and technical terms and phrases used in connection with the disclosure shall have the meanings that are commonly understood by those of ordinary skill in the art. Generally, nomenclatures used in connection with, and techniques of molecular and cellular biology, genetics, protein, nucleic acid chemistry, and hybridization described herein are those well known and commonly used in the art. The methods and techniques of the disclosure are generally performed according to conventional methods well known in the art and as described in various general and more specific references that are cited and discussed throughout the present specification unless otherwise indicated. See, for example, Sambrook et al., *Molecular Cloning: A Laboratory Manual,* 2d ed., Cold Spring Harbor Laboratory Press, Cold Spring Harbor, N.Y. (1989); and Ausubel et al., *Current Protocols in Molecular Biology*, Greene Publishing Associates (1992, and Supplements to 2002).

In a first aspect hereof, an epitope tag consisting of a four-amino acid sequence has been identified, wherein the sequence is defined by the amino acid sequence EPEA (SEQ ID NO:1) or by an amino acid sequence that has at least 25%, at least 50%, preferably at least 75% sequence identity with SEQ ID NO:1, or by an amino acid sequence wherein at least 25%, at least 50% or at least 75% of the amino acids have been substituted by a conservative amino acid.

As used herein, the term "epitope tag," or otherwise "affinity tag," refers to a short amino acid sequence or peptide enabling a specific interaction with a protein or a ligand.

Conservative substitutions, as used herein, are those in which at least one residue in the amino acid sequence has been removed and a different residue inserted in its place. Such substitutions generally are made in accordance with Table 1. Table 1 shows amino acids that can be substituted for an amino acid in a protein and are typically regarded as conservative substitutions.

TABLE 1

| Residue | Conservative Substitutions |
| --- | --- |
| Ala | Ser |
| Arg | Lys |
| Asn | Gln, His |
| Asp | Glu |
| Gln | Asn |
| Cys | Ser |
| Glu | Asp |
| Gly | Pro |
| His | Asn, Gln |
| Ile | Leu, Val |
| Leu | Ile, Val |
| Lys | Arg, Gln |
| Met | Leu, Ile |
| Phe | Met, Leu, Tyr |
| Ser | Thr, Gly |
| Thr | Ser, Val |
| Trp | Tyr |
| Tyr | Trp, Phe |
| Val | Ile, Leu |

As used herein, the terms "identical" or "percent identity" in the context of two or more polypeptide sequences, refer to two or more sequences or subsequences that are the same or have a specified percentage of amino acid residues that are the same (e.g., 75% identity over a specified region) when compared and aligned for maximum correspondence over a comparison window or designated region as measured using sequence comparison algorithms or by manual alignment and visual inspection. In particular, the identity exists over a region that is four amino acids in length.

In a second aspect, the epitope tag is linked to or coupled to a molecule, the combination being referred to herein as a "fusion molecule" or a "fusion construct." Accordingly, the disclosure relates to a fusion molecule comprising the epitope tag as described herein. Preferably, the affinity tag is linked to a protein of interest or otherwise "target protein".

The epitope tag can be linked directly or indirectly to the molecule. The tag can be linked to any site of the molecule, e.g., to or near the end or terminus of the molecule, to one or more internal sites, attached to a side chain, or to the amino-terminal amino acid (N-terminal) or to the carboxy-terminal amino acid (C-terminal). Also, more than one epitope tag can be linked to the molecule. In a preferred embodiment, the epitope tag is linked to the C-terminal end of a target protein by placing a DNA sequence encoding the epitope tag within the same open reading frame of the recombinant protein by means of genetic engineering, which is a well-known technique by the person skilled in the art.

The term "fusion molecule" or "fusion construct" as used herein generally denotes a composition that does not occur in nature, or otherwise a non-naturally occurring fusion molecule or fusion construct.

In the case of indirect linking, a suitable linker sequence is inserted between the desired molecule and the epitope tag. The epitope tag can then be removed chemically or enzymatically if a cleavage site is present in the linker sequence, using methods known in the art. Preferred linkers are peptides of 1 to 30 amino acids long and include, but are not limited to, the peptides EEGEPK (SEQ ID NO:13) (Kjeldsen et al. in WO98/28429) or EEAEPK (SEQ ID NO:14) (Kjeldsen et al. in WO97/22706); the GGGGS (SEQ ID NO:81) immunosilent linker; a protease cleavage site, such as Factor Xa cleavage site, having the sequence IEGR (SEQ ID NO:15); the thrombin cleavage site having the sequence LVPR (SEQ ID NO:16) or the enterokinase cleaving site having the sequence DDDDK (SEQ ID NO:17). Other suitable linkers are carbohydrates, PEG-based linkers, and others available in the art. Preferably, the amino acid linker sequence is short and does not interfere with the biological activity of the protein and the specific interaction with the antibody fragment. Non-limiting examples of suitable short linker sequences are as described in the Examples section, e.g., GAA and GAGA (SEQ ID NO:12), as well as in Table 2.

The term "molecule" as used herein refers to proteins, including antibodies and enzymes, peptides, nucleotides, lipids, carbohydrates, drugs and cofactors, or combinations thereof. The nature of the molecule is not critical to the invention. The molecule may be of varying length, size or molecular weight, and can have any activity known and/or desired by the skilled person.

In a particular embodiment, the molecule is a protein. More particularly, the epitope tag hereof is coupled to a protein, or a fragment thereof, the combination also being referred to as a "fusion protein." In fact, and as used herein, a "fusion protein" refers to a polypeptide that comprises the amalgamation of two amino acid sequences derived from heterogeneous sources, and as such, can be referred to as a "non-naturally occurring fusion protein." The protein can have any activity known and/or desired by the skilled person, e.g., immunogenic activity, enzymatic activity, or binding activity. The protein can also be a structural protein. Specific proteins, including fragments thereof, which can be linked to the epitope tag of this invention, include, for example, hormones, enzymes, cytokines, intracellular signaling peptides, receptors, antibodies, growth factors, blood factors, vaccines, reporter proteins, and synthetic peptides. Non-limiting examples of specific proteins are described in the Examples section, e.g., fluorescent proteins, antibody fragments, viral regulatory proteins, membrane proteins, cell cycle proteins, amongst others. In a specific embodiment, the proteins are derived from bacteria, yeasts, viruses, mammalians, plants, insects, and the like.

As used herein, the terms "polypeptide," "protein," and "peptide" are used interchangeably and refer to a polymeric form of amino acids of any length, which can include coded and non-coded amino acids, chemically or biochemically modified or derivatized amino acids, and polypeptides having modified peptide backbones.

As will be evident to one of ordinary skill in the art, various fragments of the herein-described proteins may be combined. The fragment(s) may be of varying length, although it is generally preferred that these are at least four amino acids long, and up to the length of the entire protein.

The preparation of the fusion molecules of this invention can be carried out using standard recombinant DNA methods known in the art.

According to another embodiment, the disclosure relates to an isolated nucleic acid fragment that encodes the epitope tag described herein, an isolated nucleic acid comprising the nucleic acid fragment, an isolated nucleic acid encoding the fusion molecule hereof, as well as to a composition comprising such a nucleic acid molecule. As used herein, the terms "nucleic acid," "polynucleotide," and "polynucleic acid" are used interchangeably and refer to a polymeric form of nucleotides of any length, either deoxyribonucleotides or ribonucleotides, or combinations and/or analogs thereof. The nucleic acid segments that encode the molecule and the epitope tag may be contiguous, such that in the transcription and/or translation products of the coding segments, the segments are juxtaposed. In some embodiments, the coding sequences of the tag hereof and a molecule may be separated by a linker-encoding nucleic acid sequence, or by one or more sequences that are non-coding. Thus, the disclosure encompasses nucleic acid molecules containing one or more intervening sequences (e.g., introns) that may be transcribed from a DNA molecule into an RNA molecule and subsequently removed (e.g., by splicing) prior to translation of the RNA molecule into protein. Nucleic acid molecules hereof may be synthesized in vitro, in vivo, or by the action of cell-free transcription. Preferably, a nucleotide sequence coding for the epitope tag is first synthesized and then linked to a nucleotide sequence coding for the desired molecule or protein. The thus-obtained hybrid gene can be incorporated into an expression or cloning vector using standard methods. Vectors according to this aspect hereof can be double-stranded or single-stranded and may be DNA, RNA, or DNA/RNA hybrid molecules, in any conformation including, but not limited to, linear, circular, coiled, supercoiled, torsional, nicked and the like. These vectors hereof include, but are not limited to, plasmid vectors and viral vectors, such as a bacteriophage, baculovirus, retrovirus, lentivirus, adenovirus, vaccinia virus, semliki forest virus and adeno-associated virus vectors, all of which are well-known and can be purchased from commercial sources. Any vector may be used to construct the fusion molecules used in the methods hereof. In particular, vectors known in the art and those commercially available (and variants or derivatives thereof) may be engineered, in accordance with the invention, to include one or more recombination sites for use in the methods hereof. General classes of vectors of particular interest include prokaryotic and/or eukaryotic cloning vectors, expression vectors, fusion vectors, two-hybrid or reverse two-hybrid vectors, phage and ribosome display vectors, TAP vectors, shuttle vectors for use in different hosts, mutagenesis vectors, transcription vectors, vectors for receiving large inserts and the like. Other vectors of interest include viral origin vectors (M 13 vectors, bacterial phage 8 vectors, adenovirus vectors, and retrovirus vectors), and high, low and adjustable copy number vectors. Most of the requisite methodology can be found in Ausubel et al. 2007.

Vector constructs prepared for introduction into a prokaryotic or eukaryotic host will typically comprise a replication system recognized by the host, including the intended DNA fragment encoding the fusion molecule of the disclosure, and will preferably also include transcription and translational initiation regulatory sequences operably linked to the molecule-encoding segment. Expression systems may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides may also be included, where appropriate, from secreted polypeptides of the same or related species, which allow the protein to cross and/or lodge in cell membranes, or be secreted from the cell.

An appropriate promoter and other necessary vector sequences will be selected so as to be functional in the host. Examples of workable combinations of cell lines and expression vectors are described in Sambrook et al. (1989), Ausubel et al. (Eds.) (2007), and Metzger et al. (1988). Many useful vectors for expression in bacteria, yeast, fungal, mammalian, insect, plant or other cells are well known in the art. In addition, the construct may be joined to an amplifiable gene (e.g., DHFR) so that multiple copies of the gene may be made. For appropriate enhancer and other expression control sequences, see also Enhancers and Eukaryotic Gene Expression (1983) Cold Spring Harbor Press, N.Y. While such expression vectors may replicate autonomously, they may less preferably replicate by being inserted into the genome of the host cell.

Expression and cloning vectors will likely contain a selectable marker, that is, a gene encoding a protein necessary for the survival or growth of a host cell transformed with the vector. Although such a marker gene may be carried on another polynucleotide sequence co-introduced into the host cell, it is most often contained on the cloning vector. Only those host cells into which the marker gene has been introduced will survive and/or grow under selective conditions. Typical selection genes encode proteins that (a) confer resistance to antibiotics, e.g., kanamycin, tetracycline, etc., or other toxic substances; (b) complement auxotrophic deficiencies; or (c) supply critical nutrients not available from complex media. The choice of the proper selectable marker will depend on the host cell; appropriate markers for different hosts are known in the art.

Recombinant host cells, in the present context, are those that have been genetically modified to contain an isolated DNA molecule of the instant invention. The DNA can be introduced by any means known to the art that are appropriate for the particular type of cell, including, without limitation, transformation, lipofection, electroporation or viral-mediated transduction. A DNA construct capable of enabling the expression of the fusion molecule hereof can be easily prepared by the art-known techniques such as cloning, hybridization screening and Polymerase Chain Reaction (PCR). Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989), Maniatis et al. (1982), Wu (ed.) (1993) and Ausubel et al. (1992).

An "isolated polypeptide" or an "isolated polynucleotide," as used herein, refers to, respectively, an amino acid sequence or a polynucleotide sequence that is not naturally occurring or no longer occurring in the natural environment wherein it was originally present.

In a further embodiment, the disclosure encompasses host cells comprising one or more nucleic acid molecules hereof (e.g., a nucleic acid molecule encoding one or more fusion molecules hereof). Representative host cells that may be used with the invention include, but are not limited to, bacterial cells, yeast cells, plant cells and animal cells. Bacterial host cells suitable for use with the invention include *Escherichia* spp. cells, *Bacillus* spp. cells, *Streptomyces* spp. cells, *Erwinia* spp. cells, *Klebsiella* spp. cells, *Serratia* spp. cells, *Pseudomonas* spp. cells, and *Salmonella* spp. cells. Animal host cells suitable for use with the invention include insect cells (most particularly *Drosophila melanogaster* cells, *Spodoptera frugiperda* Sf9 and SfZ1 cells and *Trichoplusa* High-Five cells), nematode cells (particularly *C. elegans* cells), avian cells, amphibian cells (particularly *Xenopus laevis* cells), reptilian cells, and mammalian cells (most particularly derived from Chinese hamster (e.g., CHO), monkey (e.g., COS and Vero cells), baby hamster kidney (BHK), pig kidney (PKl 5), rabbit kidney 13 cells (RKl 3), the human osteosarcoma cell line 143 B, the human cell line HeLa and human hepatoma cell lines like Hep G2). Yeast host cells suitable for use with the invention include species within *Saccharomyces, Schizosaccharomyces, Kluyveromyces, Pichia* (e.g., *Pichia pastoris*), *Hansenula* (e.g., *Hansenula polymorpha*), *Yarowia, Schwaniomyces, Schizosaccharomyces, Zygosaccharomyces* and the like. *Saccharomyces cerevisiae, S. carlsbergensis* and *K. lactis* are the most commonly used yeast hosts, and are convenient fungal hosts. The host cells may be provided in suspension or flask cultures, tissue cultures, organ cultures, and the like. Alternatively, the host cells may also be transgenic animals.

Methods for introducing the nucleic acid molecules and/or vectors hereof into the host cells described herein, to produce host cells comprising one or more of the nucleic acid molecules and/or vectors hereof, will be familiar to those of ordinary skill in the art. For instance, the nucleic acid molecules and/or vectors hereof may be introduced into host cells using well-known techniques of infection, transduction, transfection, and transformation. The nucleic acid molecules and/or vectors hereof may be introduced alone or in conjunction with other nucleic acid molecules and/or vectors. Alternatively, the nucleic acid molecules and/or vectors hereof may be introduced into host cells as a precipitate, such as a calcium phosphate precipitate, or in a complex with a lipid.

Electroporation also may be used to introduce the nucleic acid molecules and/or vectors hereof into a host. Likewise, such molecules may be introduced into chemically competent cells such as *E. coli*. If the vector is a virus, it may be packaged in vitro or introduced into a packaging cell and the packaged virus may be transduced into cells. Hence, a wide variety of techniques suitable for introducing the nucleic acid molecules and/or vectors hereof into cells in accordance with this aspect hereof are well known and routine to those of skill in the art. Such techniques are reviewed at length, for example, in Sambrook et al. (1989), Watson et al. (1992), and Winnacker (1987), which are illustrative of the many laboratory manuals that detail these techniques and which are incorporated by reference herein in their entireties for their relevant disclosures.

In a further aspect, the disclosure relates to an affinity ligand specifically binding to the above-described epitope tags. As used herein, the "affinity ligand" binds non-covalently to the tags of the disclosure and can be any molecule and, more particular, a metal affinity ligand, an antibody, an antibody fragment, a Nanobody™, a small molecule or a synthetic affinity ligand. In a preferred embodiment, the affinity ligand is a Nanobody™ specifically binding to the above-described epitope tag. It should be clear that the specific binding of the affinity ligand to the epitope tag, when the epitope tag is directly or indirectly coupled to a target molecule, is particularly envisaged in the disclosure.

The terms "specifically bind" and "specific binding" as used herein refer to the ability of an antibody, an antibody fragment or a Nanobody™ to preferentially bind to a particular antigen that is present in a homogeneous mixture of different antigens. In certain embodiments, a specific binding interaction will discriminate between desirable and undesirable antigens in a sample, in some embodiments more than about ten- to 100-fold or more (e.g., more than about 1000- or 10,000-fold). "Specificity" refers to the ability of an immunoglobulin or an immunoglobulin fragment, such as a Nanobody™, to bind preferentially to one antigenic target versus a different antigenic target and does not necessarily imply high affinity.

Antibodies specifically binding the herein-described tag are also part hereof Antibodies may be polyclonal and/or monoclonal. As used herein, the term "antibody" (Ab) is meant to include whole antibodies, including single-chain whole antibodies, and antigen-binding fragments. In some embodiments, antigen-binding fragments may be mammalian antigen-binding antibody fragments that include, but are not limited to, Fab, Fab' and F(ab')2, Fd, single-chain Fvs (scFv), single-chain antibodies, disulfide-linked Fvs (sdFv) and fragments comprising either a VL or VH domain, as well as nanobodies (see further herein). One or more of the epitope tags and/or fusion molecules hereof may be used as immunogens to prepare polyclonal and/or monoclonal antibodies capable of binding the epitope tags and/or fusion molecules using techniques well known in the art (Harlow and Lane, 1988). In brief, antibodies are prepared by immunization of suitable subjects (e.g., mice, rats, rabbits, goats, etc.) with all or a part of the epitope tags and/or fusion molecules hereof. If the epitope tag and/or fusion molecule, or a fragment thereof, is sufficiently immunogenic, it may be used to immunize the subject. If necessary or desired to increase immunogenicity, the epitope tag and/or fusion molecule, or fragment, may be conjugated to a suitable carrier molecule (e.g., BSA, KLH, and the like).

Thus, according to a specific embodiment, the disclosure also encompasses a method for generating antibodies specifically binding to the above-described epitope tags comprising the steps of:

(i) immunizing an animal with an epitope tag according to the invention and/or with a (fusion) protein comprising the epitope tag according to the invention; and
(ii) screening for antibodies specifically binding to the epitope tag.

Monoclonal antibodies can be prepared from the immune cells of animals (e.g., mice, rats, etc.) immunized with all or a portion of one or more epitope tags and/or fusion molecules hereof using conventional procedures, such as those described by Kohler and Milstein (1975). Thus, the disclosure provides monoclonal antibodies specific to the epitope tag and/or fusion molecule hereof, as well as cell lines producing such monoclonal antibodies. Antibodies hereof may be prepared from any animal origin including birds and mammals.

A Nanobody™ (Nb) is the smallest functional fragment or single variable domain ($V_HH$) of a naturally occurring single-chain antibody and is known to the person skilled in the art. They are derived from heavy chain only antibodies, seen in camelids (Hamers-Casterman et al. 1993; Desmyter et al. 1996). In the family of "camelids," immunoglobulins devoid of light polypeptide chains are found. "Camelids" comprise old world camelids (*Camelus bactrianus* and *Camelus dromedarius*) and new world camelids (for example, *Lama paccos, Lama glama, Lama guanicoe* and *Lama vicugna*). The single variable domain heavy chain antibody is herein designated as a NANOBODY® or a $V_HH$ antibody. NANOBODY™, NANOBODIES™ and NANOCLONE™ are trademarks of Ablynx NV (Belgium).

The small size and unique biophysical properties of Nbs excel conventional antibody fragments for the recognition of uncommon or hidden epitopes and for binding into cavities or active sites of protein targets. Further, Nbs can be designed as bispecific and bivalent antibodies or attached to reporter molecules (Conrath et al. 2001). Nbs are stable, survive the gastro-intestinal system and can easily be manufactured. Therefore, Nbs can be used in many applications including drug discovery and therapy (Saerens et al. 2008).

As used herein, "epitope" refers to an antigenic determinant of a polypeptide. An epitope could comprise three amino acids in a spatial conformation, which is unique to the epitope. Generally, an epitope consists of at least 4, 5, 6, or 7 such amino acids, and more usually, consists of at least 8, 9, or 10 such amino acids. Methods of determining the spatial conformation of amino acids are known in the art, and include, for example, x-ray crystallography and two-dimensional nuclear magnetic resonance.

The Nanobodies™ hereof generally comprise a single amino acid chain that can be considered to comprise four "framework sequences" or "FRs" and three "complementary determining regions" or "CDRs." The term "complementary determining region" or "CDR" refers to variable regions in Nanobodies™ and contains the amino acid sequences capable of specifically binding to antigenic targets. These CDR regions account for the basic specificity of the Nanobody™ for a particular antigenic determinant structure. Such regions are also referred to as "hypervariable regions." The Nanobodies™ have three CDR regions, each non-contiguous with the others (termed CDR1, CDR2, CDR3). Some preferred Nanobodies™ of the disclosure as well as their CDRs are as described herein (see Tables 3 and 4). The delineation of the CDR sequences is based on the IMGT unique numbering system for V-domains and V-like domains (Lefranc et al. 2003).

In a particular embodiment, the Nanobody™ hereof is bivalent and formed by bonding together, chemically or by recombinant DNA techniques, two monovalent single domains of heavy chains. In another particular embodiment, the Nanobody™ hereof is bi-specific and formed by bonding together two variable domains of heavy chains, each with a different specificity. Similarly, polypeptides comprising multivalent or multi-specific NANOBODIES® are included here as non-limiting examples.

Examples of the above Nanobodies™ include, but are not limited to, Nanobodies™ as defined by SEQ ID NOS:18-26 (see FIG. 1; Table 3). A non-limiting example of a bivalent Nanobody™ is defined by SEQ ID NO:68. In another embodiment, the above Nanobodies™ can comprise at least one of the complementary determining regions (CDRs) with an amino acid sequence selected from SEQ ID NOS:27-42 (see FIG. 1; Table 4). More specifically, the above Nanobodies™ can be selected from the group comprising SEQ ID NOS:18-26 (see FIG. 1; Table 3).

It should be noted that the term "Nanobody™," as used herein in its broadest sense, is not limited to a specific biological source or to a specific method of preparation. For example, the Nanobodies™ hereof can generally be obtained: (1) by isolating the $V_HH$ domain of a naturally occurring heavy chain antibody; (2) by expression of a nucleotide sequence encoding a naturally occurring $V_HH$ domain; (3) by "humanization" of a naturally occurring $V_HH$ domain or by expression of a nucleic acid encoding such humanized $V_HH$ domain; (4) by "camelization" of a naturally occurring VH domain from any animal species and, in particular, from a mammalian species, such as from a human being, or by expression of a nucleic acid encoding such a camelized VH domain; (5) by "camelization" of a "domain antibody" or "Dab" as described in the art, or by expression of a nucleic acid encoding such a camelized VH domain; (6) by using synthetic or semi-synthetic techniques for preparing proteins, polypeptides or other amino acid sequences known per se; (7) by preparing a nucleic acid encoding a Nanobody™ using techniques for nucleic acid synthesis known per se, followed by expression of the nucleic acid thus obtained; and/or (8) by any combination of one or more of the foregoing.

It is also within the scope hereof to use natural or synthetic analogs, mutants, variants, alleles, homologs and orthologs (herein collectively referred to as "analogs") of the antibodies hereof as defined herein. Thus, according to one embodiment hereof, the term "antibody hereof" in its broadest sense also covers such analogs. Generally, in such analogs, one or more amino acid residues may have been replaced, deleted and/or added, compared to the antibodies hereof as defined herein.

By means of non-limiting examples, a substitution may, for example, be a conservative substitution (as described above; see also Table 1) and/or an amino acid residue may be replaced by another amino acid residue that naturally occurs at the same position. Thus, any one or more substitutions, deletions or insertions, or any combination thereof, that either improve the properties of the antibody hereof or that at least do not detract too much from the desired properties or from the balance or combination of desired properties of the antibody hereof (i.e., to the extent that the antibody is no longer suited for its intended use) are included within the scope hereof. A skilled person will generally be able to determine and select suitable substitutions, deletions or insertions, or suitable combinations thereof, based on the disclosure herein and optionally after a limited degree of routine experimentation, which may, for example, involve introducing a limited number of possible substitutions and determining their influence on the properties of the antibodies thus obtained.

Yet another modification may comprise the introduction of one or more detectable labels or other signal-generating groups or moieties, depending on the intended use of the labeled antibody. Suitable labels and techniques for attaching, using and detecting them will be clear to the skilled person and, for example, include, but are not limited to, fluorescent labels (such as fluorescein, isothiocyanate, rhodamine, phycoerythrin, phycocyanin, allophycocyanin, o-phthaldehyde, and fluorescamine and fluorescent metals such as Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radio-isotopes, metals, metal chelates or metallic cations or other metals or metallic cations that are particularly suited for use in vivo, in vitro or in situ imaging, as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase). Other suitable labels will be clear to the skilled person and, for example, include moieties that can be detected using NMR or ESR spectroscopy. Such labeled antibodies hereof may, for example, be used for in vitro, in vivo or in situ assays (including immunoassays known per se such as ELISA, RIA, EIA and other "sandwich assays," etc.) as well as in vivo imaging purposes, depending on the choice of the specific label. As will be clear to the skilled person, another modification may involve the introduction of a chelating group, for example, to chelate one of the metals or metallic cations referred to above. Suitable chelating groups, for example, include, without limitation, diethyl-enetriaminepentaacetic acid (DTPA) or ethylenediaminetetraacetic acid (EDTA). Yet another modification may comprise the introduction of a functional group that is one part of a specific binding pair, such as the biotin-(strept)avidin binding pair. Such a functional group may be used to link the antibody hereof to another protein, polypeptide or chemical compound that is bound to the other half of the binding pair, i.e., through formation of the binding pair. For example, an antibody hereof may be conjugated to biotin, and linked to another protein, polypeptide, compound or carrier conjugated to avidin or streptavidin. For example, such a conjugated antibody may be used as a reporter, for example, in a system where a detectable signal-producing agent is conjugated to avidin or streptavidin.

In still another embodiment, a nucleic acid sequence (as defined herein) encodes any of the antibodies, antibody fragments, and/or nanobodies as described herein. Further, a vector (as defined herein) comprising a nucleic acid sequence encoding any of the antibodies, antibody fragments, and/or nanobodies as described herein is also provided, as well as a host cell (as defined herein) comprising such a vector or such a nucleic acid.

Also provided in a further aspect of the disclosure is a complex of (i) an affinity ligand as described above, and (ii) a non-naturally occurring fusion protein as described above, and (iii) optionally, a ligand specifically bound to the target protein comprised in the non-naturally occurring fusion protein. In a specific embodiment, the complex is crystalline. As used herein, the term "ligand" means a molecule that specifically binds to a target protein. A ligand may be, for example, a polypeptide, a lipid, a small molecule, an antibody or an antibody fragment (such as a Nanobody™). A ligand also includes a "native ligand," which is a ligand that is an endogenous, natural ligand for a native target protein.

As used herein, the term "complex" refers to a group of two or more associated molecules. In a preferred embodiment, a complex can be a protein complex. As used herein, the terms "protein complex" or "multiprotein complex" refer to a group of two or more associated polypeptide chains. Proteins in a protein complex are linked by non-covalent protein-protein. The quaternary structure is the structural arrangement of the associated folded proteins in the protein complex.

The epitope tags of the disclosure, as well as the affinity ligands specifically binding to these epitope tags, as well as complexes of epitope tags and affinity ligands, and/or any combinations thereof, may serve any purpose including, but not limited to:
  make a fusion molecule amenable to affinity purification methods;
  make a fusion molecule amenable to co-purification with an affinity ligand specifically binding to the epitope tag;
  make a complex of proteins and/or nucleic acids that contains the fusion molecule amenable to affinity purification methods;
  make a fusion molecule suitable for covalent or non-covalent immobilization;
  enable one to identify whether a fusion molecule is present in a sample or composition;
  enable one to localize a fusion molecule within a tissue;
  localize a fusion molecule within a cell;
  identify interactions of the fusion molecule with other proteins/protein complexes;
  determine the function of a fusion protein and how it responds to changes in cell conditions;
  determine what happens to the fusion protein during the lifetime of the cell;
  characterize new proteins derived from cloned genes; and/or
  make a fusion molecule amenable to co-crystallization with a Nanobody™ specifically binding to the epitope tag.

In particular, the epitope tags of the disclosure, as well as the affinity ligands specifically binding to these epitope tags, as well as complexes of epitope tags and affinity ligands, and/or any combinations thereof, can be used for affinity-based applications, such as affinity chromatography, affinity purification, immunoprecipitation, in vivo imaging, tandem affinity purification, protein detection, immunochemistry, surface-display, FRET-type applications, crystallography, and the like. The usefulness of the presently disclosed universal epitope tag in the above applications has been further illustrated in a non-limiting way in the Examples section.

In a specific embodiment, the disclosure relates to the use of any of the above-described epitope tags and/or affinity ligands for the purification of fusion molecules comprising one or more epitope tags hereof. As such, molecules can be purified using generalized protocols in contrast to highly customized procedures associated with conventional chromatography. Fusion molecules may be purified from the host cell or from the host cell culture medium into which they have been secreted. Typically, when purified from a host cell, the host cell is lysed using standard techniques (e.g., enzymatic digestion, sonication, French press, etc.) to form a lysate comprising the fusion molecule. The fusion molecule may be purified from a lysate or from a host cell culture medium material by contacting the lysate or medium with a suitable chromatography medium under conditions suitable for binding of the fusion molecule to the chromatography medium. The lysate or culture medium may be contacted with a chromatography medium in either a batch-wise technique (e.g., by mixing the chromatography medium with the lysate or culture medium) or column technique. The resin-bound fusion molecule may be washed one or more times to remove any weakly bounded materials, i.e., materials that do not bind as tightly as the fusion molecule to the chromatography medium. The molecule may then be eluted from the medium by contacting the medium with a suitable elution buffer known to the skilled person. The elution of the fusion molecule from the column can be carried out at a constant pH or with linear or discontinuously falling or raising pH gradients. The optimal elution conditions depend on the amount and type of impurities that are present, the amount of material to be purified, the column dimensions, the chromatography resin used, etc., and are easily determined by routine experimentation on a case-by-case basis.

In a particular embodiment, the invention relates to a method for purifying a non-naturally occurring fusion molecule comprising the steps of:
 a) applying a solution containing a molecule linked to the epitope tag as described herein to a solid support possessing an immobilized affinity ligand as described herein;
 b) forming a complex between the immobilized affinity ligand and the molecule;
 c) removing weakly bound or unbound molecule; and
 d) eluting the bound molecule.

As discussed herein, a fusion molecule may comprise a cleavage site for a protease, for example, located between the tag hereof and a molecule of interest. After elution from the chromatography medium or while still bound to the medium, a fusion molecule hereof may be contacted with a solution comprising a protease enzyme that cleaves at the cleavage site. Accordingly, in a specific embodiment, the above-described purification method further comprises a step (e) wherein the epitope tag is removed.

The purification method may be any method known in the art. Suitable purification methods include, but are not limited to, affinity chromatography (e.g., immunoaffinity chromatography, Immobilized Metal Ion Affinity Chromatography (IMAC)), metal-affinity precipitation, immobilized-metal-ion-affinity electrophoresis and immunoprecipitation.

In the case of affinity chromatography, the affinity medium contains a solid support (e.g., resin, magnetic bead, etc.) coupled to one or more of the following affinity ligands: Fe, Co, Ni, Cu, Zn, or Al-charged IMAC ligand, an antibody, an antibody fragment, a Nanobody™, a small molecule or a synthetic affinity ligand (e.g., aptamers or ligands derived using VERSAFFM™).

As is demonstrated herein, the use of the epitope tag and/or affinity ligand of the disclosure for purification results in highly purified proteins with a good yield. The term "purity" or "purified" as applied to proteins herein implies that the desired protein preferably comprises at least 60%, more preferably at least 70%, more preferably at least about 80%, still more preferably at least about 90%, and most preferably at least about 95% of the total protein component.

The elution step can be performed, amongst others, with a small compound, a peptide, using solutions of high ionic strength, or by changing the pH. In a particular embodiment, the fusion molecule can be eluted from the affinity chromatography medium by excess amounts of the epitope tag or excess amounts of the affinity ligand.

The disclosure furthermore encompasses a method for immobilizing and/or capturing a non-naturally occurring fusion molecule on a solid support comprising the steps of:
 a) applying a solution containing a molecule linked to the epitope tag as described herein to a solid support possessing an immobilized affinity ligand;
 b) forming a complex between the immobilized affinity ligand and the molecule; and
 c) removing weakly bounded molecules.

The method may be performed using immobilized elements and the immobilization may be carried out using a variety of immobilization means on various solid supports (e.g., columns, beads, adsorbents, nitrocellulose paper, etc.).

The immobilization assay can, for example, be used to screen a sample or a composition for antibodies against the molecule linked to the tag, or can be part of a screening assay in order to screen large libraries of test compounds (e.g., drugs, new antimicrobials, etc.). The screening assay is preferably conducted in a microplate format. Any means or method of detection can be used. For example, the detection means might be a plate reader, a scintillation counter, a mass spectrometer or fluorometer.

The invention further relates to a method for identifying whether a molecule is present in a sample or composition. For example, the epitope tag of the disclosure can be used in detection of a fusion molecule using the affinity ligand fused to a reporter molecule (radioactive label, alkaline phosphatase, GFP, peroxidases, and the like, see above). In a particular embodiment, the invention relates to the detection of a fusion protein according to the invention with antibodies specifically binding to the epitope tag. This embodiment can be useful in tissue or subcellular localization experiments, ELISA, Western blotting or other immunoanalytical methods.

In a particular embodiment, antibodies, including antibody fragments or nanobodies, may be used for the detection of the epitope tag in an immunoassay, such as ELISA, Western blot, radioimmunoassay, enzyme immunoassay, and may be used in immunocytochemistry. In some embodiments, an anti-tag antibody may be in solution and the tag to be recognized may be in solution (e.g., an immunoprecipitation) or may be on or attached to a solid surface (e.g., a Western blot). In other embodiments, the antibody may be attached to a solid surface and the tag may be in solution (e.g., immunoaffinity chromatography or ELISA).

Antibodies, including antibody fragments or nanobodies, to the tags and/or fusion molecules hereof may be used to determine the presence, absence or amount of one or more molecules in a sample. The amount of specifically bound tag and/or fusion molecule may be determined using an antibody to which a reporter molecule is attached, such as a radioactive, a fluorescent, or an enzymatic label. Alternatively, a labeled secondary antibody (e.g., an antibody that recognizes the antibody that is specific to the polypeptide) may be used to detect a polypeptide-antibody complex between the specific antibody and the polypeptide.

It should be clear to the skilled person that the above-described methods using the presently disclosed epitope tag can also be used in a high-throughput approach. Furthermore, combinatorial tagging also forms part of the disclosure.

In another specific embodiment, the epitope tag of the disclosure can also be useful in crystallography of proteins, where a short tag or no tag is preferred. Usually, tags are removed as it is a disadvantage for crystallization to have unstructured parts in the protein. Limited proteases are used to remove the flexible parts. Once a protein is tagged with an epitope tag of the disclosure, an affinity ligand, in particular a Nanobody™, can bind the tag, making the whole complex more soluble, easier to crystallize and helping to solve the structure of the complex. It has been shown that Nb can help in crystallization by fixating flexible loops or making crystal contacts (Loris et al. 2003; Korotkov et al. 2009).

In still another specific embodiment, the invention also provides for the use of the epitope tag and/or the affinity ligand of the disclosure in a Tandem Affinity Purification (TAP) method in order to purify protein complexes under native conditions. The TAP tagging method (Rigaut et al.

1999; Puig et al. 2001) can be applied to the yeast proteome very successfully, and has been adapted to various cells and organisms. However, while the method is intrinsically sound, it has a number of drawbacks, in particular, the size of the TAP tag can be in the region of 21 kDa and the larger a tag is, the greater the possibility that it will interfere with the function or structure of the polypeptide to be isolated, or, alternatively, be cleaved or digested by the polypeptide target. Commonly used tag combinations for TAP are well known and summarized in Li (2010). The epitope tags of the disclosure can be incorporated in the development of TAP tags for affinity-based applications.

In a further aspect, the invention also provides for a kit for use in any of the affinity-based applications as described herein. Such a kit may comprise, without the purpose of being limitative, one or more of the following elements:
- one or more (poly)peptides hereof, optionally detectably labeled, and optionally associated with a non-soluble matrix or solid support;
- one or more affinity ligands hereof, optionally pre-immobilized to a non-soluble matrix or solid support;
- nucleic acids hereof;
- vector constructs hereof;
- labeling reagents known in the art;
- a set of instructions; and/or
- buffers, elution components, detection components known in the art.

It is to be understood that although preferred embodiments, specific constructions and configurations, as well as materials, have been discussed herein for the methods and tools according to the disclosure, various changes or modifications in form and detail may be made without departing from the scope and spirit of this invention. Therefore, the disclosure is limited only by the claims attached herein.

TABLE 2

| Epitope tags, peptides, linker sequences | |
|---|---|
| Amino acid sequence | SEQ ID NO: |
| EPEA | 1 |
| GYQDYEPEA | 2 |
| DYEPEA | 3 |
| YQDYEPEA | 4 |
| QDYEPEA | 5 |
| GYQDYEPE | 6 |
| SEEGYQDYEPEA | 7 |
| GAAEPEA | 8 |
| GAGAEPEA | 9 |
| GAGAGYQDYEPEA | 10 |
| YEPEA | 11 |
| GAGA | 12 |
| EEGEPK | 13 |
| EEAEPK | 14 |
| IEGR | 15 |
| LVPR | 16 |
| DDDDK | 17 |

TABLE 3

| Nanobodies that specifically bind to α-synuclein | | |
|---|---|---|
| NAME (see FIG. 1) | NO. OF AMINO ACIDS | SEQ ID NO: |
| Nb85 | 127 | 18 |
| Nb88 | 127 | 19 |
| NbSyn2 PstI | 126 | 20 |
| NbSyn2 | 126 | 21 |
| NbSyn1b | 126 | 22 |
| NbSyn1c | 126 | 23 |
| NbSyn1a | 126 | 24 |
| Nb86 | 124 | 25 |
| Nb87 | 122 | 26 |

TABLE 4

| CDRs of nanobodies that specifically bind to α-synuclein | | | |
|---|---|---|---|
| Nanobody (see FIG. 1) | CDR1 | CDR2 | CDR3 |
| Nb85 | GLTYSNYC (SEQ ID NO: 27) | ISTRGIKT (SEQ ID NO: 28) | AAVIYPGYGDSCPWTT SVNY (SEQ ID NO:29) |
| Nb88 | GYTYSRIC (SEQ ID NO: 30) | ISTRGIKT (SEQ ID NO: 28) | AAVIYPGYGDSCPWTT SVNY (SEQ ID NO: 29) |
| NbSyn2 PstI | GIDSSSYC (SEQ ID NO: 31) | INGLGGVKT (SEQ ID NO: 32) | AAKFSPGYCGGSWSN FGY (SEQ ID NO: 33) |
| NbSyn2 | GIDSSSYC (SEQ ID NO: 31) | INGLGGVKT (SEQ ID NO: 32) | AAKFSPGYCGGSWSN FGY (SEQ ID NO: 33) |
| NbSyn1b | GLNASSYC (SEQ ID NO: 34) | INGNAGIKT (SEQ ID NO: 35) | AAKSSPGYCGGNWDN FGY (SEQ ID NO: 36) |
| NbSyn1c | GLNASSYC (SEQ ID NO: 34) | INGNAGIKT (SEQ ID NO: 35) | AAKSSPGYCGGNWDN FGY (SEQ ID NO: 36) |

TABLE 4 -continued

CDRs of nanobodies that specifically bind to α-synuclein

| Nanobody (see FIG. 1) | CDR1 | CDR2 | CDR3 |
|---|---|---|---|
| NbSyn1a | GLNASSYC (SEQ ID NO: 34) | INGNAGIKT (SEQ ID NO: 35) | AAKSSPGYCGGNWDN FGY (SEQ ID NO: 36) |
| Nb86 | GYTFRGNR (SEQ ID NO: 37) | INTGGVNT (SEQ ID NO: 38) | AADLTGWRPVGFSGY NY (SEQ ID NO: 39) |
| Nb87 | GYSGY (SEQ ID NO: 40) | IYRGDKIT (SEQ ID NO: 41) | AARRVVADSPLLSKTY AY (SEQ ID NO: 42) |

EXAMPLES

Example 1

Isolation, Expression and Purification of Nanobodies Against α-Synuclein

Camelid nanobodies, e.g., NbSyn1a, NbSyn1b, NbSyn1c and NbSyn2, Nb85, Nb86, Nb87 and Nb88 were isolated from either a dromedary immunized with α-synuclein (Uniprot accession number P37840) or a dromedary immunized with two proteins: the α-synuclein Ala53Thr mutant and β-synuclein (Uniprot accession number is Q16143). α-Synuclein and β-synuclein share 85% identity in the N-temiinal part of the protein; in the C-terminal part, both proteins are less homologous (±40%). Both proteins share the same C-terminal EPEA (SEQ ID NO:1) sequence. All nanobodies were selected by phage-display, essentially according to published protocols (Lauwereys et al. 1998; Conrath et al. 2001) or as described in materials and methods. In vitro selection on immobilized α-synuclein only revealed one family of binders: NbSyn1a, NbSyn1b, and NbSyn1c. A second in vitro selection was performed on immobilized α-synuclein in the presence of 10 μM of NbSyn1a. From this selection, we obtained NbSyn2 after three rounds of panning. From the dromedary immunized with two proteins (the α-synuclein A53T mutant and β-synuclein), one independent phage display library of $10^7$ independent clones was constructed. This library was panned in parallel against β-synuclein and the α-synuclein A53T mutant in two separate in vitro selections. Nb85, Nb86 and Nb87 were recovered from the beta-synuclein panning. Two of these binders (Nb85, Nb86) were also selected on Ala53Thr α-synuclein. One add binder Nb88 was also recovered from the Ala53Thr α-synuclein panning. It thus appears that Nb85 and Nb86 bind α-synuclein A53T as well as β-synuclein. Nb88 only differs from Nb85 by a few point mutations in framework 1 and CDR1, while the CDR2 and CDR3 are identical (FIG. 1).

All nanobodies were recloned into pHEN6 to have six histidines at the C-terminus. The purification occurred using immobilized metal affinity chromatography (IMAC) and size exclusion chromatography essentially according to published protocols (Conrath et al. 2001).

Example 2

Epitope Characterization of the Nanobodies Against Synuclein

We used $^{15}$N—$^{1}$H heteronuclear single quantum correlation spectroscopy (HSQC) to map the epitope of NbSyn2, Nb85 and Nb87 on α-synuclein by observing perturbations to the backbone amide resonances. Titration of unlabeled Nb into $^{15}$N-labeled α-synuclein resulted in both broadening and shifts of specific resonances in the HSQC spectrum of the latter.

Figure 2B:
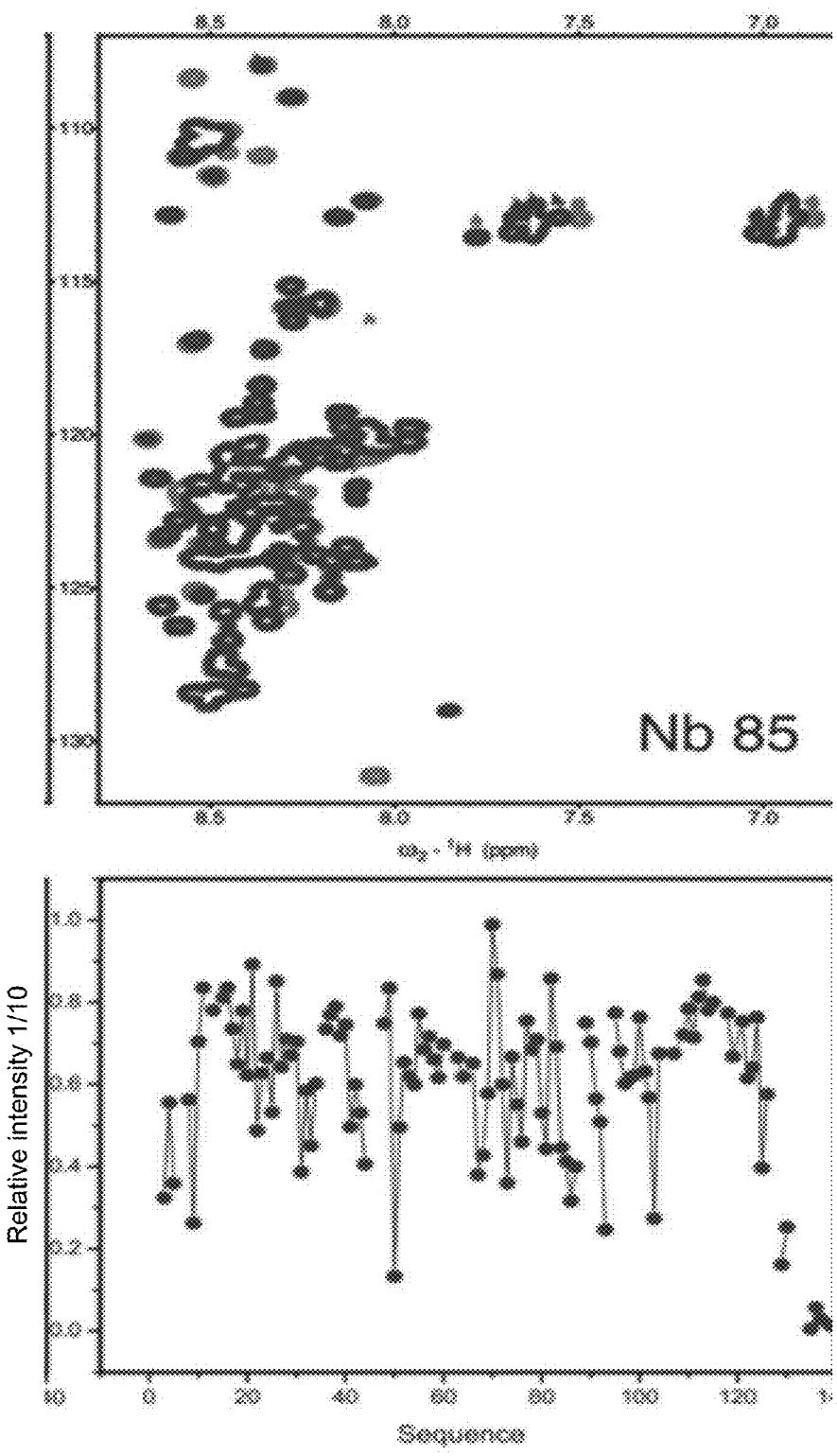
Figure 2C:
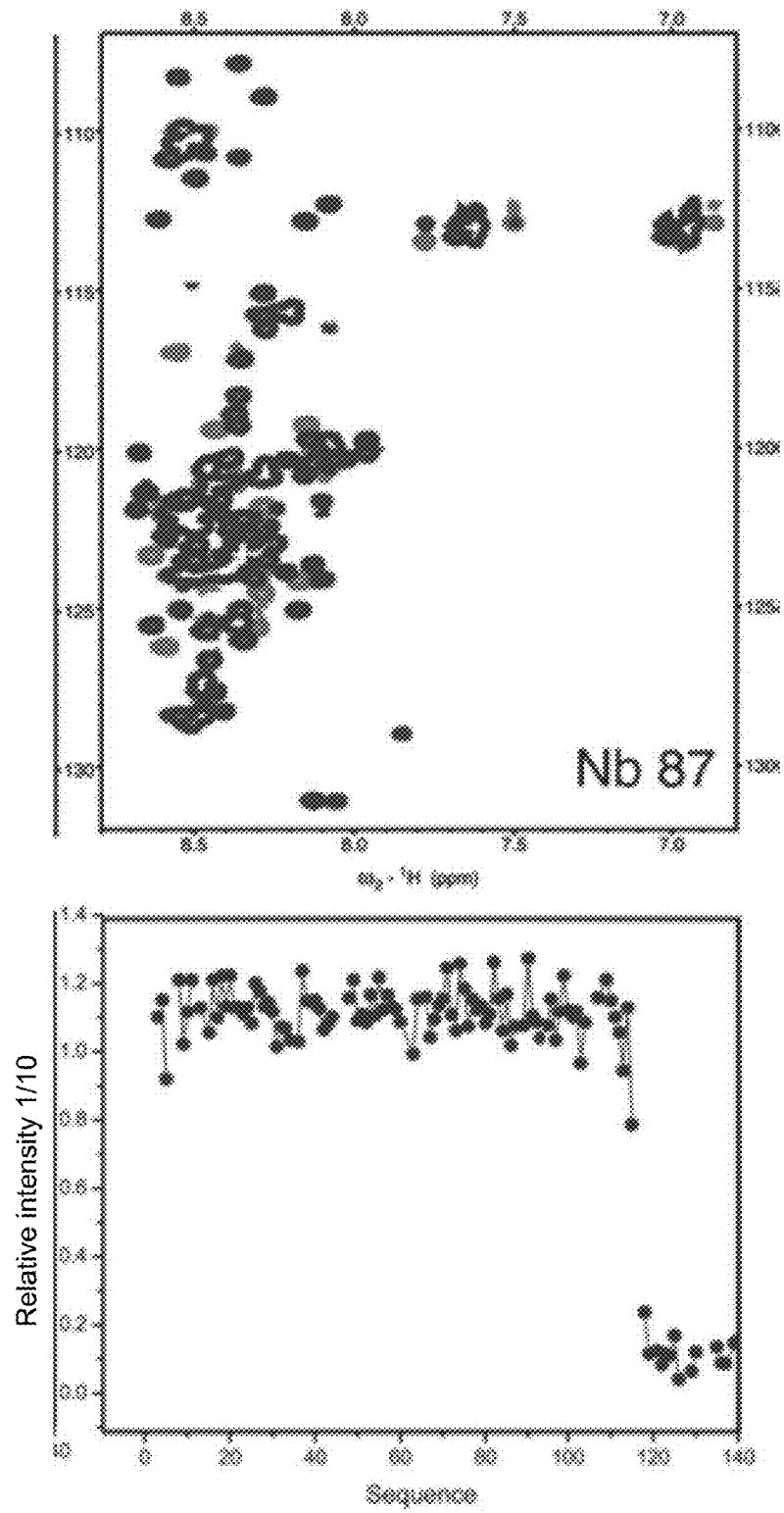

The effect of binding of NbSyn2, NbSyn85 and Nb87 to the HSQC spectrum of labeled α-synuclein is shown in FIGS. 2A-2C. The top panel represents the raw spectra obtained upon addition of Nb, where the red peaks correspond to the free and the blue peaks correspond to the signals of α-synuclein in complex with the different nanobodies. The lower panels of FIGS. 2A-2C summarize a titration experiment using subequimolar to equimolar concentrations of Nb as the titrant. In the used concentration range, most of the affected HSQC cross-peaks of labeled α-synuclein either disappear completely (intermediate exchange) or reappear in a different region in the spectrum (slow exchange). This is highly consistent with the formation of a stable complex upon binding. When the relative intensity of the peaks of the free synuclein spectrum in the free and bound spectra is plotted for each amino acid along the sequence (bottom panel of FIGS. 2A-2C), the C-terminal region is subjected to the greatest perturbations in terms of chemical shift or intensity upon binding of each of the nanobodies. These data indicated that all three nanobodies bind to the C-terminal region of α-synuclein.

Example 3

Affinity Measurements of Nanobodies Interacting with α-Synuclein

Isothermal titration calorimetry (ITC) was used to monitor the binding of NbSyn2 to α-synuclein. Measurements were performed at temperatures between 20° C. and 37° C. and the data are consistent with a 1:1 bimolecular association between NbSyn2 and α-synuclein in each case, with Kd values of 106±21 nM, 130±23 nM, 99±17 nM and 260±69 nM at 20° C., 25° C., 30° C. and at 37° C., respectively (Table 5).

TABLE 5

Thermodynamic parameters of the NbSyn2:alpha-synuclein interaction as measured by Isothermal Calorimetry (ITC)

| Ligand | T (K) | ΔH (kcal mol−1) | TΔS (kcal mol−1) | ΔG (kcal mol−1) | Stoichiometry | Kd (nM) | ΔCp (kcal mol−1 K−1)[a] |
|---|---|---|---|---|---|---|---|
| Peptide[b] | 293.1 | −11.20 ± 0.24 | 2.31 ± 0.25 | −8.88 ± 0.07 | 0.98 ± 0.01 | 240 ± 26 | −0.22 ± 0.01 |
|  | 298.1 | −12.44 ± 0.35 | 3.28 ± 0.36 | −9.16 ± 0.09 | 0.99 ± 0.01 | 190 ± 30 |  |
|  | 303.1 | −13.50 ± 0.76 | 4.72 ± 0.77 | −8.78 ± 0.14 | 0.94 ± 0.02 | 460 ± 110 |  |
|  | 310.1 | −14.89 ± 0.83 | 6.29 ± 0.84 | −8.61 ± 0.09 | 0.92 ± 0.03 | 850 ± 130 |  |
| Full-length α-synuclein | 293.1 | −18.00 ± 0.53 | 8.65 ± 0.55 | −9.35 ± 0.12 | 0.99 ± 0.01 | 106 ± 21 | −0.23 ± 0.01 |
|  | 298.1 | −19.05 ± 0.45 | 9.67 ± 0.46 | −9.39 ± 0.10 | 0.93 ± 0.01 | 130 ± 23 |  |
|  | 303.1 | −20.32 ± 0.42 | 10.61 ± 0.43 | −9.71 ± 0.10 | 0.87 ± 0.01 | 99 ± 17 |  |
|  | 310.1 | −21.79 ± 1.23 | 12.47 ± 1.24 | −9.33 ± 0.16 | 0.91 ± 0.03 | 260 ± 69 |  |

[a]The contribution of protonation to the value of ΔH was determined using a 10 mM tris-HCL buffer 100 mM NaCl at pH 7.4 and was found to be insignificant.
[b]The sequence of the peptide, N-YEPEA-C (SEQ ID NO: 11), corresponds to the residues Y136-A140 of full-length α-synuclein.

A similar ITC measurement was performed as described in material and methods using NbSyn2 and a peptide fragment of α-synuclein, encompassing D135-A140 of the α-synuclein sequence (NH2-DYEPEA-COOH (SEQ ID NO:3)). Similar binding characteristics were observed, indicating that this peptide contains the epitope of NbSyn2 on α-synuclein (see Example 4). We found that the corresponding affinities and ΔCp value are very similar to those for the interaction with the full-length α-synuclein (Table 5). This finding confirms that the ΔCp value arises overwhelmingly from the direct binding of NbSyn2 to these residues located within the C-terminal peptide of α-synuclein, and not as a consequence of significant conformational changes within the remainder of the molecule.

Example 4

Crystallization of the NbSyn2-Peptide Complex

Figure 6:
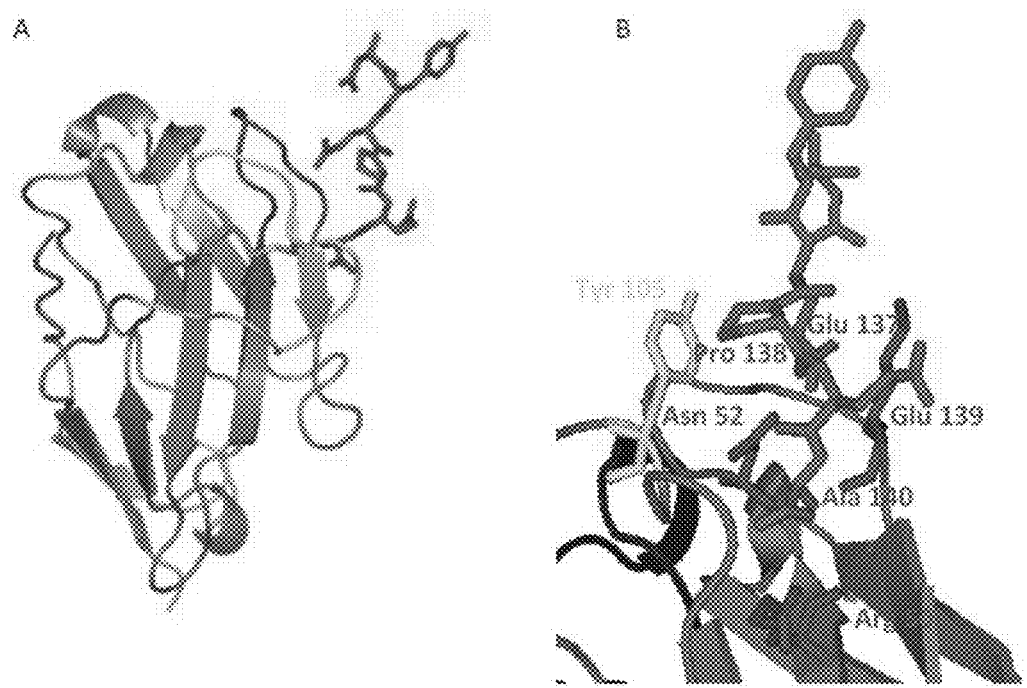
FIG. 6: Structure of the single-domain camelid antibody fragment Nbsyn2 in complex with the C-terminal peptide (GYQDYEPEA—SEQ ID NO:2) of α-synuclein. Panel (A) gives a schematic overview of the complex. The framework is represented in grey while the CDR1, CDR2 and CDR3 loops are in green, red and yellow, respectively. The peptide is colored purple. Panel (B) depicts the molecular interactions between the Nanobody™ and the peptide.

In another experiment, we crystallized NbSyn2 in complex with the peptide NH$_2$-GYQDYEPEA-COOH (SEQ ID NO:2), corresponding to residues 132-140 of α-synuclein (FIG. 6). In the X-ray structure of the complex, we observe significant electron density only for the last six C-terminal residues of the peptide. The other residues of the peptide are not visible in the electron density, indicating that they are highly flexible and disordered in the complex and implying that they are not involved in specific interactions with NbSyn2. The residue Asp135 only shows poor-defined electron density (FIG. 7, first top panel) and although there is clear density for Tyr136, this residue is involved in crystal-packing contacts with a symmetry-related complex (FIG. 7, second top panel), indicating that the conformation of the side chain of Tyr136 could be more flexible in solution.

Figure 7:
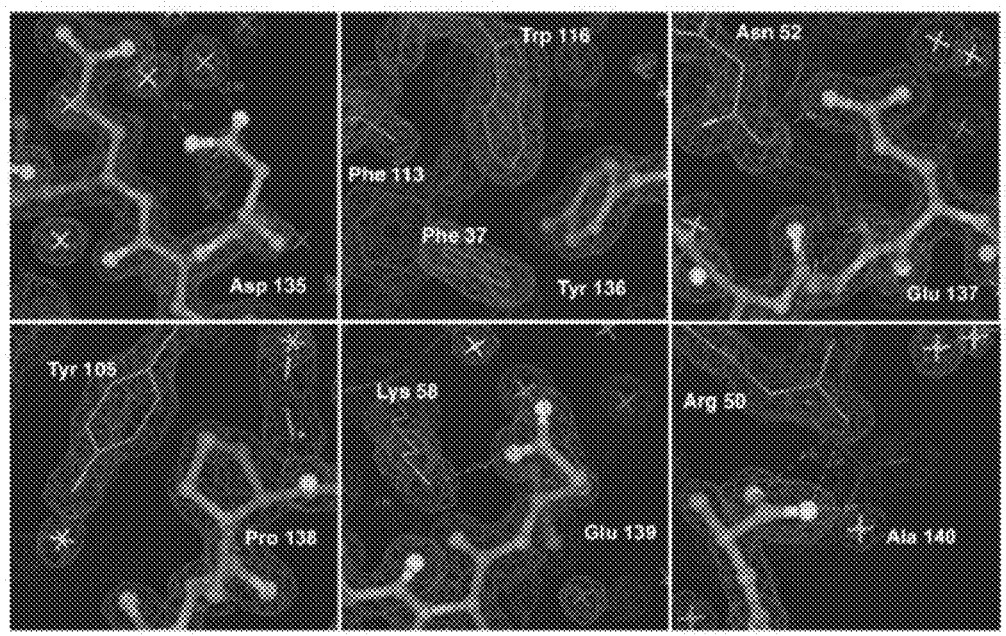
FIG. 7: Detailed view of the side-chain interactions between the residues of the peptide with NbSyn2. Residues of the peptide are represented as sticks and residues of NbSyn2 are drawn as lines. Atoms are color-coded: C: green; N: pink; O: yellow. A $2F_o$-$F_c$ map contoured at 1σ, is represented as a light blue mesh. The interactions for each side chain are represented in different panels (from left to right, top panels: Asp 135, Tyr 136, Glu 137; bottom panels: Pro 138, Glu 139, Ala 140). Note that the side-chain of Tyr 136 interacts with residues of a symmetry-related NbSyn2 molecule.

Analysis of the structure at the atomic level reveals that the peptide binds to NbSyn2 in a pocket formed by residues of the CDR3 and CDR2 loops of NbSyn2. The residues of CDR2 and CDR3 loops make contacts with residues Tyr136, Glu137, Pro 138, Glu139 and Ala140 of the peptide. The binding is primarily mediated through side-chain interactions and is mainly electrostatic in nature, although an important hydrophobic interaction occurs between Pro138 of the peptide and Tyr105 of NbSyn2, where the $C_\gamma$ and $C_\delta$ of the cyclic aliphatic ring of Pro138 stack perpendicularly against the aromatic ring of Tyr105. The $C_\beta$ of Ala140 is deeply buried in a pocket formed between the CDR3 and CDR2 loops of the Nb (FIG. 6, Panel B), while the carbonyl groups of the C-terminus of Ala140 make a salt-bridge with Arg50 of NbSyn2 (FIG. 7). The peptide main-chain atoms, apart from the carbonyl groups of Ala140 and the carbonyl oxygens of Pro138 and Glu137, which make direct hydrogen bonds with residues of NbSyn2, are either exposed to solvent or make indirect contact with the Nanobody™ through bridging water molecules.

The determination of the crystal structure of NbSyn2 bound to a peptide encompassing the nine C-terminal residues of α-synuclein (PDB-code 2×6M) confirms that NbSyn2 binds the last four C-terminal residues of α-synuclein and, more specifically, the C-teriminal sequence EPEA (SEQ ID NO:1) (FIG. 6).

Example 5

Affinity Purification of Tagged GFP

The NMR experiments (Example 2) and the ICT data (Example 3) show that the nanobodies NbSyn2, Nb85 and Nb87 bind the C-terminal end of α-synuclein. The X-ray structure (Example 4) confirms that NbSyn2 interacts mainly to the last four amino acids. To further confirm that these nanobodies bind this C-terminal linear four-amino acid epitope, we decided to construct different GFP-peptide hybrids. By standard DNA cloning techniques, we made four different constructs of a GFP (Green Fluorescent Protein) fused to different tags at the C-terminal end:

```
                                        (SEQ ID NO: 2)
    1. GFP-GYQDYEPEA (CA1508)

(SEQ ID NO: 4)
    2. GFP-YQDYEPEA (CA1509)

(SEQ ID NO: 5)
    3. GFP-QDYEPEA (CA1510)

(SEQ ID NO: 6)
    4. GFP-GYQDYEPE (CA1511)
```

The four constructs were cloned into the pBADmycHis vector as described in material and methods.

All GFP hybrids were expressed in the cytoplasm of *E. coli*. No green fluorescence could be observed in cells transformed with construct CA1510, indicating that this fusion protein is poorly expressed. However, functional GFP expression could be obtained for CA1508, CA1509 and CA1511, as indicated by the green fluorescence of the induced cells transformed with these constructs. Nanobodies Nb85, Nb87, Nb88 and NbSyn2 were expressed by standard procedures in the periplasm of *E. coli*. Next, periplasmatic fractions containing one of the nanobodies were mixed with cellular lysates containing one of the four tagged GFP proteins and incubated for one hour. Then, we copurified the different GFP fusions with the His-tagged nanobodies from these mixtures by IMAC. In this co-purification experiment, high salt (1 M NaCl) was added to avoid aspecific binding.

Figure 3:
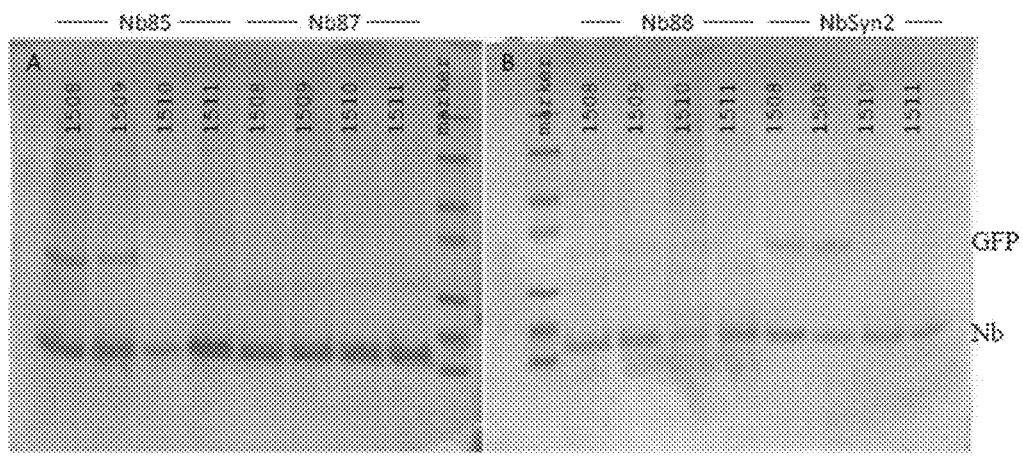
FIG. 3: IMAC purification of EPEA (SEQ ID NO:1)-tagged GFP in complex with Nanobodies™ Nb85, Nb87, Nb88 or NbSyn2. Purified complexes were analyzed by SDS-PAGE analysis. Panel (A) lanes 1 to 4: Nb85 in complex with CA1508, CA1509, CA1510 or CA1511; lanes 5 to 8: Nb87 in complex with CA1508, CA1509, CA1510 or CA1511; lane 9: protein marker. Panel (B) lane 1: protein marker; lanes 2 to 5: Nb88 in complex with CA1508, CA1509, CA1510 or CA1511; lanes 6 to 9: NbSyn2 in complex with CA1508, CA1509, CA1510 or CA1511.

Next, copurified Nb-GFP complexes were eluted from the column by imidazol and the eluted fractions were analyzed by SDS-PAGE (FIG. 3). Using Nb85 or NbSyn2, we were able to copurify the tagged GFPs encoded by CA1508 and CA1509 from crude cell lysate mixtures. The GFP construct where the last Alanine from the Tag was missing (CA1511) could never be recovered, indicating that this C-terminal Ala is crucial for the binding of these GFP fusions by Nb85 or NbSyn2.

Figure 4:
FIG. 4: Affinity purification of a tagged GFP (CA1508) using NbSyn2 coupled to a resin: affinity-purified tagged GFP was analyzed by SDS-PAGE analysis. Lane 1: protein marker; lane 2: wash with 50 mM Tris HCl pH7.5 without salt; lane 3: elution with 50 mM Tris HCl containing 1 M NaCl pH7.5; lane 4: elution with 50 mM TrisHCl containing 1 M NaCl pH7.5; lane 5: elution with 50 mM Tris HCl pH7.5 containing 0.5 M adipic acid.
Figure 5:
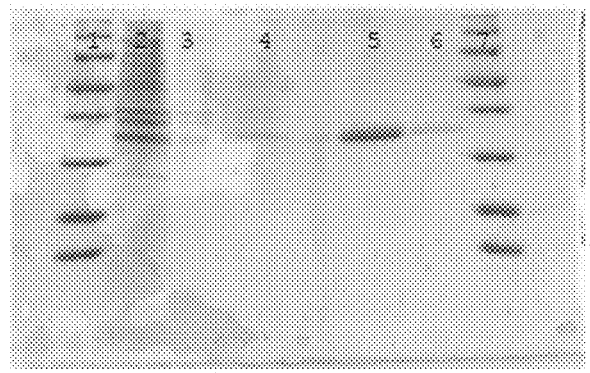
FIG. 5: Affinity purification of a tagged GFP (CA1508) using NbSyn2 coupled to a resin: affinity-purified tagged GFP was analyzed by SDS-PAGE analysis. Lane 1: protein marker; lane 2: flow through; lanes 3 and 4: wash with 50 mM TrisHCl pH7.5; lane 5: elution containing 750 μM peptide GYQDYEPEA (SEQ ID NO:2); lane 6: elution with 50 mM Tris HCl containing 2 M NaCl pH7.5; lane 7: protein marker.

In a second step, an affinity column was prepared by immobilizing NbSyn2 on a sepharose matrix. NbSyn2 was coupled to a CNBr-activated sepharose according to the manufacturer's instructions. In a separate experiment, GFP fused to the GYQDYEPEA (SEQ ID NO:2) tag (construct CA1508) was expressed in E. coli. Cells were recovered by centrifugation and lysed. This crude lysate containing the tagged GFP (construct CA1508) was then mixed with agarose slurry containing the immobilized NbSyn2 and incubated for one hour at 4° C. Next all the beads were recovered on a filter in a small column and washed with ten column volumes (cv) 50 mM Tris pH 7.5 and with 10 cv of 50 mM Tris/1 M NaCl pH7.5 to get rid of aspecific binding and equilibrated with 50 mM Tris pH7.5. We tried to elute the GYQDYEPEA (SEQ ID NO:2)-tagged GFP with different buffers, all containing 50 mM TrisHCl and titrated to pH7.5: 0.5 M citric acid, 0.5 M N-L-a-aspartyl-L-fenylalanine-1-methylester (Aspartame), 0.5 M aspartaat/tyrosine, 0.5 M glutamic acid/tyrosine, 0.5 M formic acid or 0.5 M adipic acid. Elution of the GFP fusion was monitored by measuring the fluorescence of the eluate: adipic acid as well as NaCl was found to elute the tagged GFP from the affinity matrix. Eluates were next analyzed on SDS-PAGE and confirmed this observation: one specific band with a molecular weight corresponding to the GFP fusion could be identified on SDS-PAGE (FIG. 4). In a separate experiment, we trapped the GFP-GYQDYEPEA (SEQ ID NO:2) fusion from a crude lysate onto the NbSyn2 affinity column, washed it with 10 cv of buffer and successfully eluted the tagged GFP with 750 μM of the (synthesized) free NH$_2$-GYQDYEPEA-COOH (SEQ ID NO:2) peptide (FIG. 5). In this case, we also identified one band with a molecular weight corresponding to the GFP fusion on SDS-PAGE. With a second high salt wash (2 M NaCl), hardly any remaining protein could be eluted from the column, indicating that the peptide quantitatively elutes GYQDYEPEA (SEQ ID NO:2)-tagged proteins with the synthetic GYQDYEPEA (SEQ ID NO:2) peptide.

In conclusion, in using a NbSyn2 affinity column, we were able to trap the GFP-GYQDYEPEA (SEQ ID NO:2) fusion (CA1508) from a cell lysate and to elute it from the affinity column with molar concentrations of NaCl or adipic acid or with millimolar concentrations of the synthetic NH$_2$-GYQDYEPEA-COOH (SEQ ID NO:2) peptide.

Example 6

Affinity Purification of Tagged Nanobodies

Figure 8:
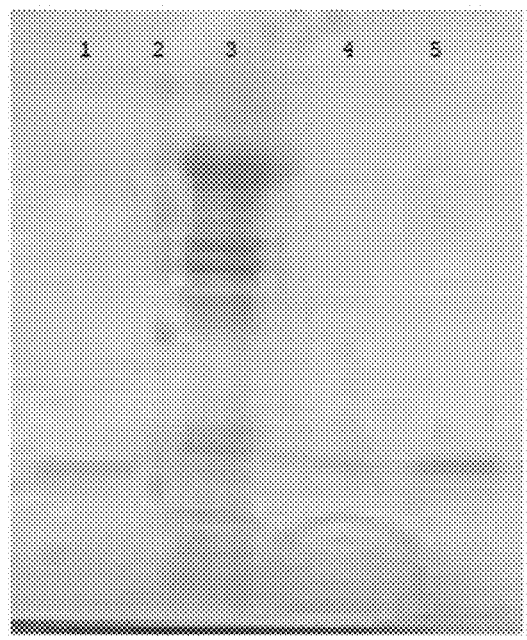
FIG. 8: Affinity purification of a tagged Nanobody™ (Nb458) using NbSyn2 coupled to a resin: affinity-purified tagged versions of Nb458 were analyzed by SDS-PAGE analysis: lane 1: Nb458-GYQDYEPEA (SEQ ID NO:2); lane 2: protein marker; lane 3: Flow through; lane 4: Nb458-gaaEPEA (SEQ ID NO:8); lane 5: Nb458-gaaEPEA (SEQ ID NO:8).

As another example, we also tagged a Nanobody™ (that is specific for another protein) and purified it using a NbSyn2 affinity resin. To produce tagged Nanobodies™, we constructed two new plasmids, pMESy1 and pMESy2, that are described in detail in Material and Methods. In pMESy1, the original His-tag was replaced by the longer GYQDYE-PEA (SEQ ID NO:2). In pMESy2, we cloned the four-amino acid EPEA (SEQ ID NO:1) tag behind a small GAA-linker. One VHH, Nb458 (recognizing an unrelated antigen or Aox1 of Pichia pastoris; SEQ ID NO:66), was cloned in both vectors using the PstI and Eco91I site. Both tagged versions of Nb458 were expressed in the periplasm of E. coli. Fresh periplasmic fractions were prepared and mixed with a slurry of NbSyn2 cross-linked to Sepharose®-beads as described in Example 4. The Sepharose® slurries were collected on the filter of small columns and washed with 50 mM TrisHCl pH7.5. Both tagged Nanobodies™ could be successfully eluted from these columns with 1 M of NaCl (FIG. 8). In conclusion, using a NbSyn2 affinity column, we were able to trap the Nb458-GYQDYEPEA (SEQ ID NO:2) fusion and the Nb458-gaaEPEA (SEQ ID NO:8) fusion from a cell lysate and were able to elute it from the affinity column with molar concentrations of NaCl.

Example 7

Application of the EPEA-Tag in ELISA

Figure 9:
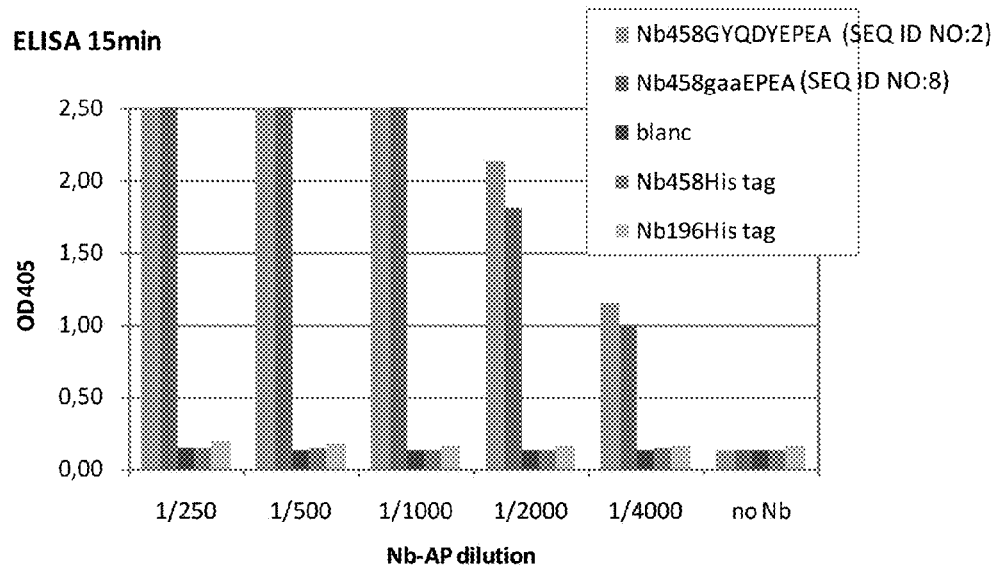
FIG. 9: Detection of EPEA (SEQ ID NO:1)-tagged nanobodies in ELISA using a self-made NbSyn2 alkaline phosphatase conjugate. Nb458-GYQDYEPEA (SEQ ID NO:2) (CA2944), Nb458-gaaEPEA (SEQ ID NO:8) (CA2945), and two His-tagged nanobodies (Nb458—SEQ ID NO:66 and Nb196—SEQ ID NO:65) were coated in different wells of an ELISA plate. Self-made NbSyn2 alkaline phosphatase conjugate was added. The ELISA was developed using p-Nitrophenyl phosphate as a substrate.

First, we coated different wells of a 96-well plate with Nb458 tagged at its C-terminus with GYQDYEPEA (SEQ ID NO:2) and with Nb458 tagged with the gaaEPEA (SEQ ID NO:8) tag, respectively. Next, the plate was blocked with milk in PBS. Both immobilized EPEA (SEQ ID NO:1)-tagged Nb458 were detected using the His-tagged NbSyn2 (His-tag at the C-terminus of NbSyn2), followed by an antiHis mouse monoclonal and an anti-mouse alkaline phosphatase conjugate. Significant alkaline phosphate activity could be detected only in those wells that were coated with Nb458 tagged at its C-terminus with GYQDYEPEA (SEQ ID NO:2) or with Nb458 tagged with the gaaEPEA (SEQ ID NO:2) tag as compared to the blank wells, which were only blocked with milk. Next, we coated different wells of an ELISA plate with (1) Nb458 with the hexa Histidine-epitope tag, (2) Nb458 with the GYQDYEPEA (SEQ ID NO:2) tag and (3) Nb458 with the gaaEPEA (SEQ ID NO:8) tag. All wells were blocked with milk. In this experiment, the EPEA (SEQ ID NO:1)-tagged, but not the His-tagged, Nanobody™ could be detected with a self-made NbSyn2 alkaline phosphatase conjugate. A clear signal was obtained only for the GYQDYEPEA (SEQ ID NO:2) and the gaaEPEA (SEQ ID NO:8)-tagged constructs (FIG. 9). It thus appears that the short EPEA (SEQ ID NO:1) tag can be used in combination with NbSyn2 to detect recombinantly expressed proteins in ELISAs.

Example 8

Application of the EPEA-Tag in Western Blot

Figure 10:
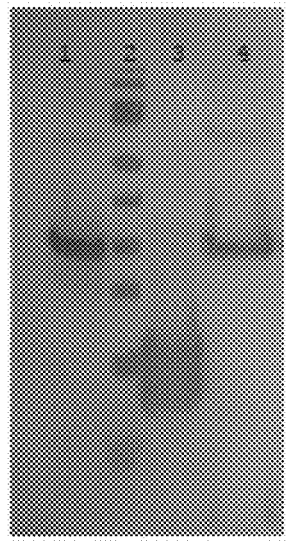
FIG. 10: Detection of EPEA (SEQ ID NO:1)-tagged proteins in Western Blot. GYQDYEPEA (SEQ ID NO:2)-tagged GFP (lanes 1 and 4), α-synuclein (lane 3), and a protein marker (lane 2) were separated on SDS-PAGE and transferred to a nitro-cellulose sheet. The Western blot was developed using His-tagged NbSyn2 as the primary antibody. Nb190 is an His-tagged Nanobody™ that recognizes an unrelated antigen.
Figure 11:
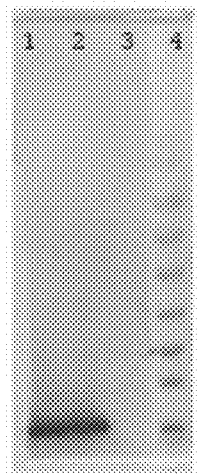
FIG. 11: Detection of EPEA (SEQ ID NO:1)-tagged proteins in Western Blot. Nb458-gaaEPEA (SEQ ID NO:8) (lane 1), Nb458-GYQDYEPEA (SEQ ID NO:2) (lane 2) and a protein marker (lane 3) were separated on SDS-PAGE and transferred to a nitro-cellulose sheet. The Western blot was developed using a self-made NbSyn2 alkaline phosphatase conjugate in combination with NBT/BCIP.

We tested the EPEA (SEQ ID NO:1) tag NbSyn2 combination in Western blot analysis. In a first experiment, GYQDYEPEA (SEQ ID NO:2)-tagged GFP (CA1508) and α-synuclein were run on an SDS-PAGE and transferred to a nitrocellulose sheet. Both blotted proteins could be visualized by using the His-tagged NbSyn2 as the primary antibody, a mouse monoclonal anti His-tag antibody as the secondary antibody and an anti-mouse alkaline phosphatase conjugate in combination with NBT and BCIP to develop the blot (FIG. 10). In a similar Western blot experiment, we could visualize blotted GYQDYEPEA (SEQ ID NO:2)-tagged Nb458 (CA2944) and also Nb458-gaaEPEA (SEQ ID NO:8) (CA2945) in a single step with our self-made NbSyn2-alkaline phosphatase conjugate (NbSyn2-AP) in combination with NBT and BICP (FIG. 11). It thus appears that the short EPEA (SEQ ID NO:1) tag can be used in combination with NbSyn2 to detect recombinantly expressed proteins in Western blots.

Example 9

In Vitro Detection and Analysis of Large Protein Libraries with the EPEA Tag

Figure 12:
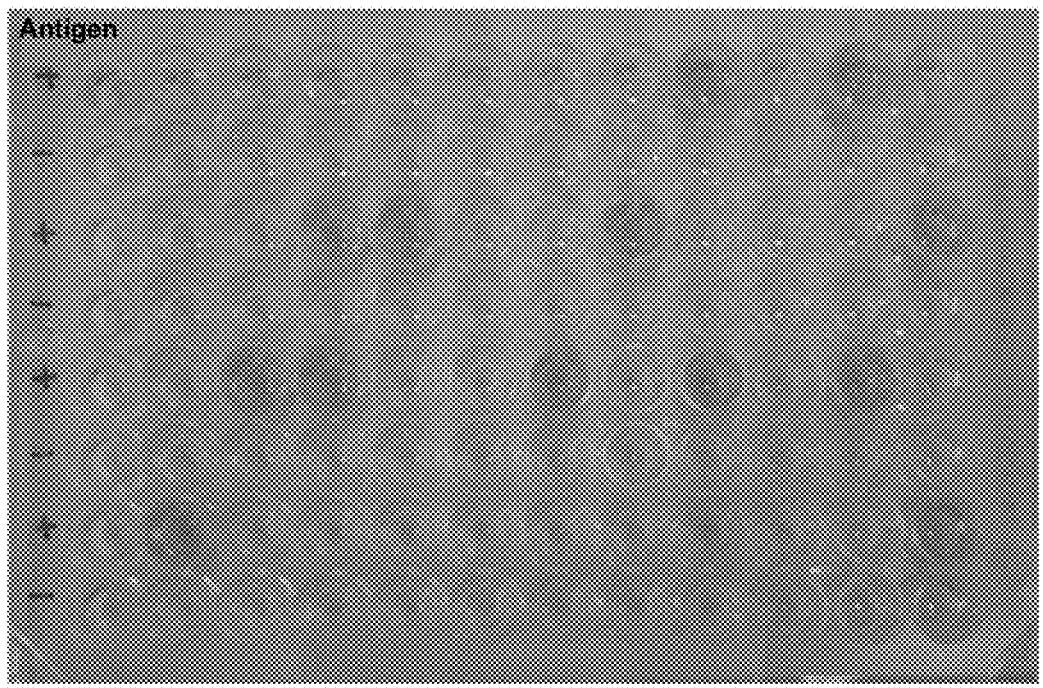
FIG. 12: High throughput screening of a collection of VHHs carrying the EPEA (SEQ ID NO:1) tag using ELISA. Antigen was coated to the wells of the rows marked + of an ELISA plate. Forty-eight nanobodies, selected through phage display, were added to the coated wells and to control wells without antigen (marked −). Antigen-specific nanobodies were detected using our self-made NbSyn2 alkaline phosphatase conjugate and p-nitrophenyl phosphate as a substrate.

It is clear from Example 7 that C-terminally EPEA (SEQ ID NO:1)-tagged proteins can be detected in ELISA with NbSyn2-AP. To confirm that this tag also works in high throughput applications, we used NbSyn2 to screen large phage-displayed libraries of EPEA (SEQ ID NO:1)-tagged VHHs. For this purpose, we cloned a VHH (Nanobody™) library (of an immunized llama) in phage display vector pMESy2. Two different in vitro selections by phage display were carried out to select subsets of Nanobodies™ against two different antigens. Screening of these subsets of clones for Nanobodies™ that are specific for one antigen were performed by an ELISA as follows: antigen was coated on 96-well plates, plates were blocked, and each well was incubated with the perplasmatic fraction of another clone expressing a different VHH gene in fusion with the EPEA (SEQ ID NO:1) tag. Detection was performed with the NbSyn2 AP conjugate (FIG. 12). In both experiments, different specific binders were identified. It thus appears that the short EPEA (SEQ ID NO:1) tag can be used in combination with NbSyn2 to detect recombinantly expressed proteins in a high-throughput analysis of phage display libraries and of libraries of recombinant proteins generated by other genomics or proteomics approaches.

Example 10

In Vivo Detection of EPEA Tagged Proteins with NbSyn2

Figure 13:
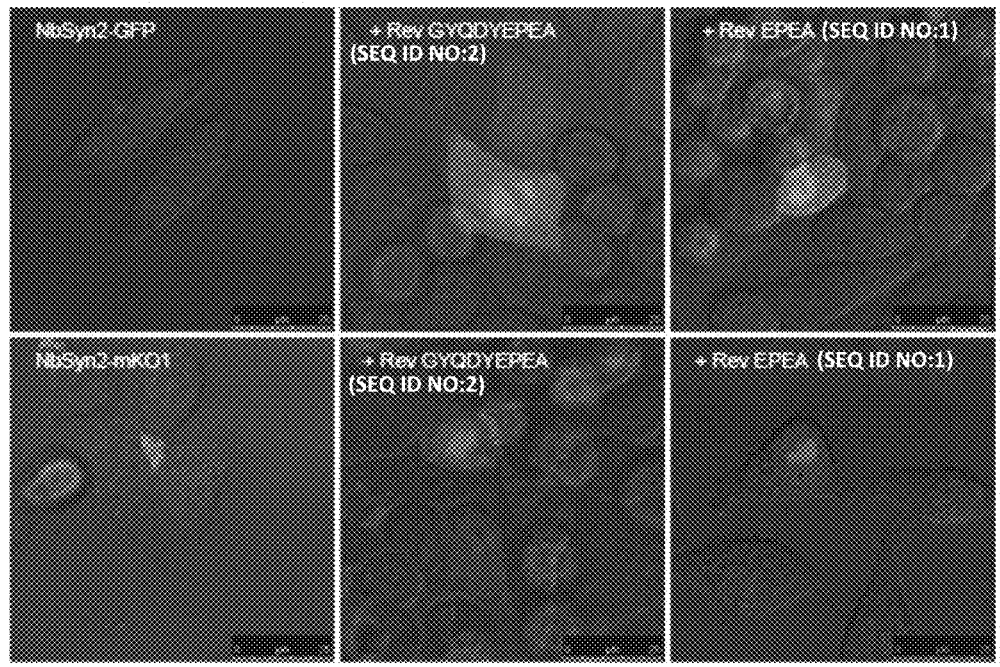
FIG. 13: Visualization of the EPEA (SEQ ID NO:1)-tagged HIV-Rev protein inside a HeLa cell with a NbSyn2-GFP fusion or NbSyn2-mKO1. Upper panels: HeLa cell lines were transfected with NbSyn2-GFP separately and in combination with HIV-Rev-GYQDYEPEA (SEQ ID NO:2) and HIV-Rev-EPEA (SEQ ID NO:1), respectively. Lower panels: HeLa cell lines were transfected with NbSyn2-mKO1 separately and in combination with HIV-Rev-GYQDYEPEA (SEQ ID NO:2) and HIV-Rev-EPEA (SEQ ID NO:1), respectively.

In another set of experiments, we explored the use of the EPEA (SEQ ID NO:1) tag to detect/visualize the expression of recombinant proteins within a (living) eukaryotic cell. For this purpose, two different proteins (HIV-Rev and GFP) were EPEA (SEQ ID NO:1)-tagged (Rev-GAGAGYQDYE-PEA (SEQ ID NO:10), Rev-GAGAEPEA (SEQ ID NO:9), GFP-GYQDYEPEA (SEQ ID NO:2) and GFP-GAAEPEA (SEQ ID NO:8)) and cloned into a pcDNA transfection vector for transient expression in eukaryotic cells. To allow the detection of EPEA (SEQ ID NO:1)-tagged proteins, NbSyn2 or NbSyn1a were fused to mKO1 or GFP and cloned into pcDNA to give NbSyn1a-mKO1, NbSyn2-mKO1, NbSyn1a-GFP and NbSyn2-GFP fusions. HeLa cells were transfected with these vectors or with combinations of these vectors to see whether we could detect the expression and specify the location of the EPEA (SEQ ID NO:1)-tagged proteins with GFP or mKO1 fused to NbSyn1a or NbSyn2. FIG. 13 shows that the cells that are transfected with NbSyn2 or NbSyn1a fused to mKO1 or GFP color the cell uniformly. Cells that are double-transfected with Rev-GAGAGYQDYEPEA (SEQ ID NO:10) or Rev-GAGAEPEA (SEQ ID NO:9) and NbSyn2 or NbSyn1a fused to mKO1 or GFP have a deeper color in the nucleoli. It is known that wild-type Rev shuttles between the nucleoli and the cytoplasm of the cell with the majority of the protein localized in the nucleoli (Perkins et al. 1989). It thus appears that the fluorescent Nanobody™ fusions and the EPEA (SEQ ID NO:1)-tagged Rev protein colocalize in the nucleus of a double-transfected cell, confirming that both the GYQDYE-PEA (SEQ ID NO:2) and the EPEA (SEQ ID NO:1) tags are recognized in vivo NbSyn2 or NbSyn1a fusions, even in the nucleus of the cell (FIG. 13).

Example 11

Figure 14:
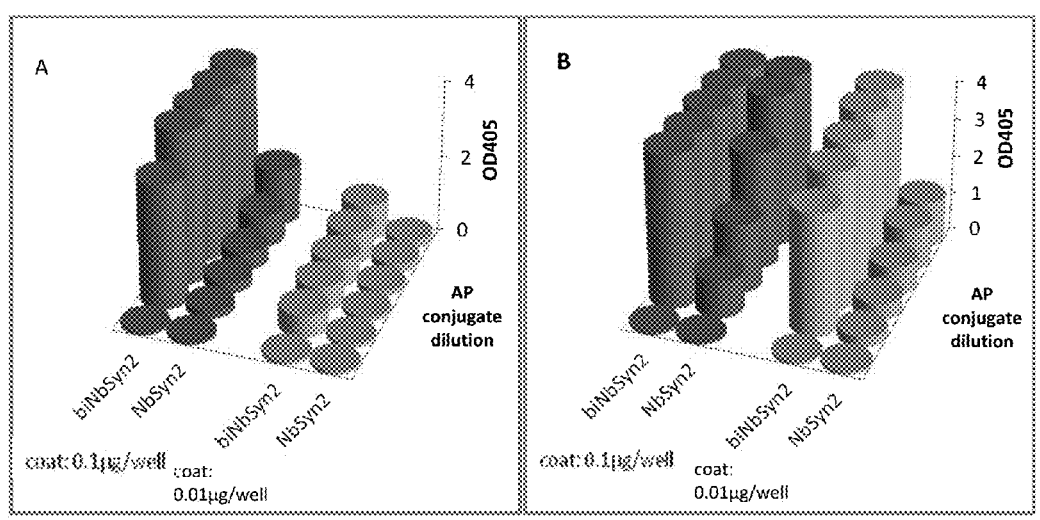
FIG. 14: Detection of EPEA (SEQ ID NO:1)-tagged nanobodies in ELISA using the biNbSyn2 alkaline phosphatase conjugate. Nb458-gaaEPEA (SEQ ID NO:8) (CA2945) was coated at different concentrations per well of an ELISA plate (0.1 μg or 0.01 μg/well). biNbSyn2 alkaline phosphatase conjugate or NbSyn2 alkaline phosphatase conjugate were added in different dilutions: 1/250, 1/500, 1/1000, 1/2000 and 1/4000. The ELISA was developed using p-Nitrophenyl phosphate as a substrate. The OD405 value was measured (A) after 60 minutes of incubation and (B) after an overnight incubation.

Improvement of the Sensitivity of the In Vitro Detection Using a Bivalent Nanobody It is clear from Example 9 that the EPEA (SEQ ID NO:1) tag works in high-throughput applications. To improve the sensitivity of the ELISA, we constructed a bivalent version of NbSyn2, named biNbSyn2 (SEQ ID NO:68). For this purpose, we amplified the NbSyn2 gene and cloned it as a bivalent construct with a GGGGSGGGS (SEQ ID NO:69) linker between both NbSyn2 sequences in the phage display vector pMES4. Expression, purification and conjugation of the biNbSyn2 to alkaline phosphatase were done as described in Materials and Methods to the Examples. To compare the monovalent NbSyn2 with the bivalent "biNb-Syn2," an ELISA was done as follows: antigen Nb458-gaaEPEA (SEQ ID NO:8) was coated on 96-well plates, at different concentrations, plates were blocked. Detection was performed, either with the NbSyn2-AP conjugate or with the biNbSyn2-AP conjugate. From this experiment, it is clear that the sensitivity of detection increases by using the biNbSyn2 (FIG. 14, Panels A and B).

Example 12

Detection and Affinity Purification of a Tagged Membrane Protein

Figure 15:
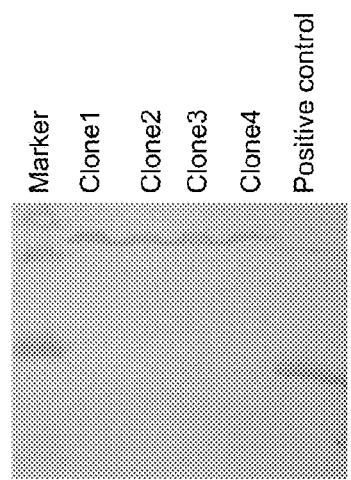
FIG. 15: Detection of an EPEA (SEQ ID NO:1)-tagged membrane protein CsgG in Western blot. A protein marker (lane 2), clones 1 to 4 of the EPEA (SEQ ID NO:1)-tagged CsgG (lanes 2 to 5) and a positive control (EPEA (SEQ ID NO:1)-tagged Nanobody™) (lane 6) were separated on SDS-PAGE and transferred to a nitro-cellulose sheet. The Western blot was developed using the self-made NbSyn2 alkaline phosphatase conjugate.
Figure 16:
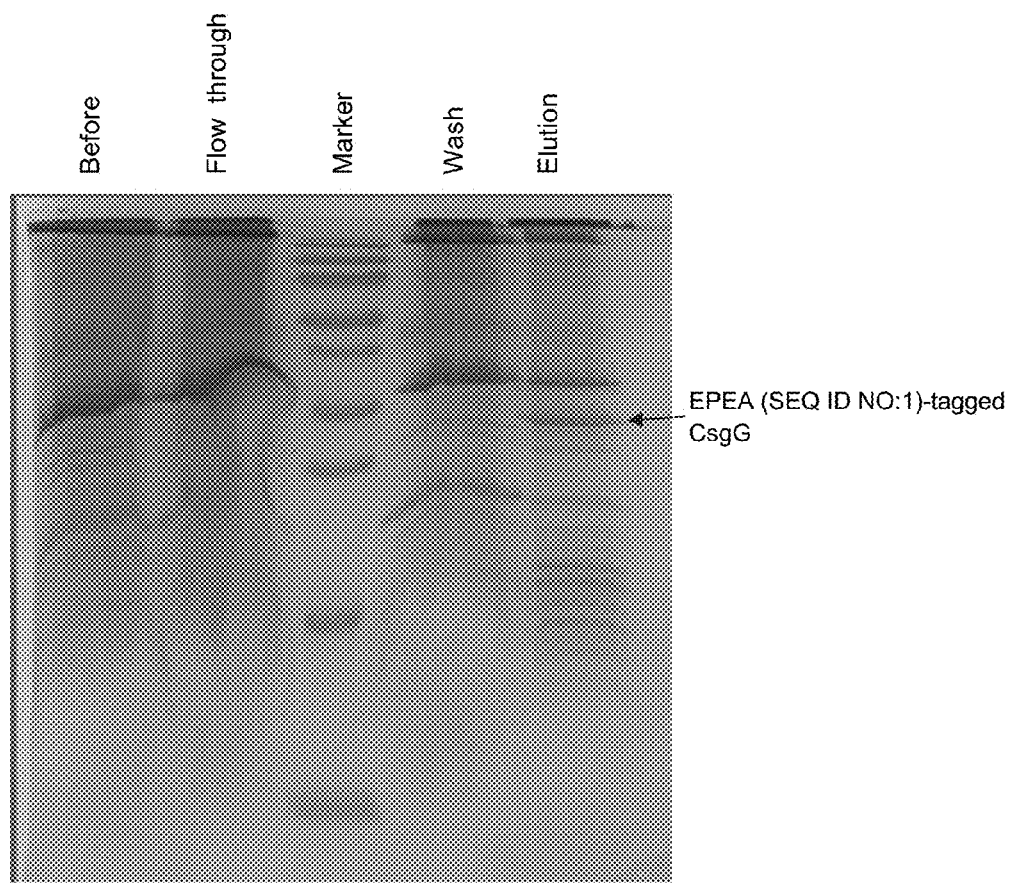
FIG. 16: Affinity purification of a tagged membrane protein (CsgG) using NbSyn2 coupled to a resin: affinity-purified material was analyzed by SDS-PAGE analysis: lane 1: sample before purification, Nb458-GYQDYEPEA (SEQ ID NO:2); lane 2: Flow through; lane 3: protein marker; lane 4: wash; lane 5: CsgG-EPEA (SEQ ID NO:1).

As another example, we also tested whether tagged membrane proteins could be detected and purified by using affinity purification. Therefore, we tagged a membrane protein CsgG, checked its expression by Western blot, and partially purified it using a NbSyn2 affinity resin. The *E. coli* UTI89 CsgG, cloned with its native RBS, behind the trc promotor in the pTrc99a (pMC2; Robinson et al. 2006) was modified to include a C-terminal EPEA (SEQ ID NO:1) affinity tag. Using the SLIM (Site-directed Ligation Independent Mutagenesis; Chiu et al. 2004) method, this C-terminal His tag was replaced with a sequence encoding GGEPEA (SEQ ID NO:70), as described in detail in Material and Methods. A small-scale culture of *E. coli* cells were grown and IPTG was added to induce the production of the EPEA-tagged CsgG (SEQ ID NO:72). Western blot was done on four individual clones of this construct to prove the presence of the CsgG protein. A clear band running at the correct height could be detected (FIG. 15). The plasmid was transformed to BL21 cells for a large-scale production of the EPEA (SEQ ID NO:1)-tagged CsgG. Cell membranes were prepared as described in Material and Methods. Finally, the membranes were solubilized overnight in 1% n-dodecyl beta-D-maltoside (DDM) and the solubilized material was run over a small column containing the NbSyn2 cross-linked to Sepharose-beads as described in Example 4. The beads were washed with 25 mM Tris pH8, 1 mM DTT, 0.02% DDM, 1% C8E4, 5 mM LDAO. A clear enrichment of the membrane protein could be seen after elution with the small synthetic $NH_2$-SEPEA-COOH peptide (SEQ ID NO:71), demonstrating that capturing of EPEA (SEQ ID NO:1)-tagged membrane proteins from 1% detergent solution is possible (FIG. 16).

Materials and Methods to the Examples

All restriction enzymes, T4 DNA ligase were purchased from Fermentas.

Bacterial Strains and Plasmids

The *Escherichia coli* strains used were TG1: supE thi-1 Δ(lac-proAB) Δ(mcrB-hsdSM)5 ($r_k^- m_k^-$) [F' traD36 proAB lacI$^q$ZΔM15], Top10 [mcrA Δ(mrr-hsdRMS-mcrBC) φ80lacZΔM15 ΔlacX74 deoR recA1 araD139 Δ (ara-leu) 7697 galU galK rpsL (=Str$^R$) endA1 nupG] (Invitrogen, Basel, Switzerland), WK6 [Δ(lac-proAB), galE, strA/F' lacI$^q$, lacZΔM15, proA$^+$B$^+$] (Zell & Fritz, 1987) and BL21 cells (Invitrogen).

Plasmids pHEN4 (Ghahroudi et al. 1997), pHEN6 (Lauwereys et al. 1998), pMES4 (genbank GQ907248), pBad-MycHis (Invitrogen), pcDNA3.1. (Invitrogen) and pMC2 (Robinson et al. 2006) were used.

Immunization, Isolation, Expression and Purification of Nanobodies Against α-Synuclein A dromedary (one) was six times immunized subcutaneously with α-synuclein during a six-week period. A second dromedary (two) was immunized with α-synuclein Ala53Thr and β-synuclein. From both animals, total RNA was isolated from about $10^7$ lymphocytes as described by Chomczynski and Sacchi (1987). First strand cDNA synthesis was prepared using a dN6 primer and the superscript RT according to the manufacturer's (Invitrogen) instructions. From dromedary one, the gene fragments encoding VHH genes were amplified by PCR using specific primers as described previously (Conrad et al. 2001). For the nested PCR, one primer that anneals at the framework 1 (5'-GATGTGCAGCTG-CAGGAGTCTGGRGGAGG-3') (SEQ ID NO:43) and three other primers (5'-GTAGCGGC-CGCTGGGGTCTTCGGGGTGGT-GCGCTGAGGA-GACGGTGACCTGGGT-3' (SEQ ID NO:44), 5'-GTAGCGGCCGCTTGGTTGGGGTATCTTGGGTTCT-GAGGAGA-CGGTGACCTGGGT-3' (SEQ ID NO:45), 5'-GTAGCGGCCGCTTACTTCATTCGTTCCTGAGGA-GACGGTGA-CCTGGGT-3') (SEQ ID NO:46) that anneal at the different hinge regions of the heavy chain of the heavy chain dromedary immunoglobulins (Conrad et al. 2003) were used. VHH genes were cloned in the pHEN4 vector (Ghahroudi et al. 1997) using the NcoI and the NotI restriction enzymes and transformed into TG1 cells (genepulser, Biorad) according to standard protocols. From dromedary two, the gene fragments encoding the VHH genes were amplified and cloned as described by Conrad et al. (2001). The VHH repertoire of both libraries was expressed on the phage after superinfection with M13K07. In vitro selection from the first library occurred on solid-phase coated α-synuclein (10 µg/well) in the wells of a maxisorp microtiter plate (Nunc) or on solid-phase coated α-synuclein Ala53Thr or β-synuclein for the second library. Bound phage were eluted with 100 mM triethylamine (pH 11). Subsequent steps, the recloning of the selected binders, the expression, and purification was done as described by Conrad et al. (2001).

Library Construction and Phage Display Using EPEA (SEQ ID NO:1) Tag

A cDNA library was constructed and all VHH genes were amplified as described above. To clone the VHH genes into the pMESy2 vector, vector and PCR products were digested with PstI and the Eco91I restriction enzymes, purified and ligated with T4 DNA ligase overnight. Insert analysis was done by PCR with primers RP and GIII. The VHH repertoire of the library was expressed on the phage after superinfection with helperphage. Specific binders were selected in vitro from the library on solid phase-coated protein (2×5 µg/well) in the wells of a maxisorp microtiter plate (Nunc).

Phages were recovered by incubating the coated wells with 100 mM triethylamine pH 10 for ten minutes and the eluate (containing phages) was neutralized by adding TrisHCl pH 6.8. This eluate was added to freshly grown TG1 cells. The coated wells were then washed once with TrisHCl pH 6.8 and several times with PBS, and freshly grown TG1 cells were added to the wells to recover the non-eluted phages. Colony screening for specific binders was done by ELISA using the NbSyn-AP as described above.

A new phage display vector combining the hexa histidines tag and the EPEA (SEQ ID NO:1) tag was constructed: pMESy4 (referred to as CA3198) was made as follows: Primers EP177: (5'-GTCACCGTCT-CCTCACACCAC-CATCACCATCACGAACCTGAAGCCTAGTACCC-3') (SEQ ID NO:47) and EP178: (5'-GTACGGGTACTAG-GCTTCAGGTTCGTGATGGTGATGGTGGTGTGAGGA-GACG-3') (SEQ ID NO:48) were mixed together at a concentration of 50 µM. Both primers were heated to 95° C. in a water bath and very slowly cooled down to room temperature. Hereafter, the primers were diluted to a concentration of 1 µM. One hundred ng or 0.034 pmol of purified pMES4 cut with BsIWI and Eco91I was mixed with 1.7 pmol of primers and ligated ON with T4 DNA ligase. WK6 *E. coli* cells were transformed, analyzed by PCR and sequenced.

NMR Measurements

All NMR experiments were performed using Bruker Avance 500 MHz or 700 MHz spectrometers equipped with cryoprobes. All NMR data were subsequently processed using NMRpipe72 and the program SPARKY73 was used for analysis of the data.

$^{15}$N—$^1$H HSQC Measurements With or Without $^{14}$N NbSyn2 and Assignment of the Bound Form of Labeled α-Synuclein Standard $^{15}$N—$^1$H HSQC experiments were carried out on a Bruker Avance 700 MHz instrument equipped with a cryoprobe. Spectra of $^{15}$N-labeled α-synuclein were recorded at different molar equivalents of unlabeled NbSyn2 (0.25, 0.5, 0.75, 1.0, 1.25, 1.5, 1.75, 2.0, 2.5, 3.0, 3.25) by titration of small volumes of a concentrated stock solution of NbSyn2. All experiments were recorded in 10 mM phosphate buffer pH 7.4 and at 10° C. The amide resonances and $C_β$ and $C_α$ chemical shifts were determined previously (Dedmon et al. 2005a; 2005b) and used in the further analysis of the data. The chemical shifts of the α-synuclein resonances in complex with NbSyn2 were assigned using a series of standard 3D experiments: CBCA(CO)NH and HNCACB. Sample integrity checks were performed between and after each 3D experiment by recording $^{15}$N—$^1$H HSQC spectra.

$^{13}$C—$^{15}$N CON Measurements of $^{15}$N $^{13}$C-Labeled α-Synuclein With or Without $^{14}$N NbSyn2

$^{13}$C—$^{15}$N CON experiments, which correlate the $^{13}$C carbonyl chemical shift of residue n with the $^{15}$N chemical shift of residue n+1, were performed as described previously (Bermel et al. 2006). The assignments of all cross-peaks in the spectra were obtained from Bermel et al. 2006. In total, two CON spectra were recorded for $^{15}$N$^{13}$C-labeled α-synuclein free and after addition of one equivalent of $^{14}$N NbSyn2. The spectra were recorded on a 500 MHz Bruker Avance spectrometer equipped with a cryoprobe. The sample buffer was 10 mM phosphate buffer at pH 7.4 and the temperature was set at 283 K. The assignments of the CON cross-peaks of α-synuclein in the bound form were obtained by comparing the $^{15}$N chemical shifts for the corresponding peaks in the assigned $^{15}$N—$^1$H HSQC spectrum for bound α-synuclein.

$^{15}$N—$^1$H HSQC Measurements and Assignment of $^{15}$N $^{13}$C-Labeled NbSyn2 Bound to Full-Length α-Synuclein and a Peptide Fragment of α-Synuclein We have reported the assignments of the backbone resonances of NbSyn2 elsewhere (Vuchelen et al. 2009). The backbone assignments of samples of $^{15}$N$^{13}$C-labeled NbSyn2 at 0.3 mM in 20 mM phosphate buffer at pH 7.4 bound to α-synuclein were obtained by means of HNCA experiments using a Bruker Avance 700 MHz spectrometer equipped with a cryoprobe. Titrations of full-length $^{14}$N α-synuclein and a $^{14}$N 12-residue peptide, N-SEEGY-QDYEPEA-C (SEQ ID NO:7) (Genemed Synthesis, Inc, New York), were carried out with $^{15}$N-labeled NbSyn2 at 0.3 mM in 20 mM phosphate buffer pH 7.4 at 298 and 283 K.

Isothermal Calorimetry Measurements

Calorimetric measurements were recorded using a MCS-ITC calorimeter (MicroCal, LLC, Northampton, Mass., USA). A solution of 273 μl NbSyn2, at a concentration of 75 μM was titrated in aliquots of 10 μl into the calorimetric cell, containing 1.4 ml of 5 μM α-synuclein. Both proteins were dialyzed prior to measurements in exactly the same buffer containing 10 mM phosphate, 150 mM sodium chloride at a pH of 7.4. Each injection was performed every four minutes at the desired temperature. A titration of NbSyn2 in the sample cell containing only buffer was subtracted from the actual binding experiment before analysis. The thermodynamic analysis was performed using the Microcal analysis software (Origin 7.0) with a 1:1 binding model. The temperature dependence of ΔH, allowed the calculation of ΔCp through the relationship ΔCp=δΔH/δT. The contribution of protonation to the ΔH was evaluated using a 10 mM Tris-HCL buffer 100 mM NaCl at pH 7.4.

Cloning, Expression in E. Coli and Purification of Tagged GFP

Four different tags were attached to the gfp gene by PCR using Takara Ex Taq polymerase (TAKARA BIO INC). The same specific primer EP124 (5' TAATCATGAG-CAAAGGAGAAGAACTTTTCAC 3') (SEQ ID NO:67) was used in all constructs; it anneals at the N-terminus of the gene. Different primers were used to fuse the coding sequence of different tags at the C-terminus: for GYQDYE-PEA (SEQ ID NO:2), primer EP126 (5'-TTCGAATT-CAT-TACGCTTCCGGTTCATAATCCTGATATCCTTTGTA-GAGCTCATCCATGC 3') (SEQ ID NO:49) was used, for YQDYEPEA (SEQ ID NO:4), we used primer EP127 (5'-TTCGAATTCATTACGCTTCCGGTTCATAATCCTGAT-ATTTGTAGAGCT-CATCCATGCC-3') (SEQ ID NO:50), and for QDYEPEA (SEQ ID NO:5), primer EP128 (5'-TTCGAATTCATTACGCTTCCGGTTCATAAT-CCT-GTTTGTAGAGCTCATCCATGCC-3') (SEQ ID NO:51) was used. Amplification conditions were four minutes at 94° C., 28 times (40 seconds at 94° C., 40 seconds at 50° C., one minute at 72° C.) and ten minutes at 72° C. The amplified gfp fusions coding for GFP fusion molecules with different epitope tags were cut with BspHI and EcoRI. The PCR products were ligated into the pBADmycHis vector, opened with NcoI and EcoRI. Finally, the ligation product was transformed into E. coli Top10. To construct GFP with the GYQDYEPE (SEQ ID NO:6) tag, 1 μl of the EP124-EP126-amplified GFP fragment was used as template for an extra PCR using primers EP124 and EP129 (5' TTCGAATTCAT-TATTCCGGTTCATAATCCTG 3') (SEQ ID NO:52). The amplified PCR product was cloned to the pBADmycHis vector as written above.

To express the differently tagged GFP fusions, E. coli cell cultures were induced by the addition of 0.02% arabinose at a cell density of $OD_{600}$=0.7 and were further incubated overnight at 37° C. The cells from a 330 ml LB culture were harvested by centrifugation (ten minutes at 4000 rpm at 4° C.) and the pellet was resuspended in 20 ml 50 mM Tris-HCl pH 7.5 with 1 mM PMST. Cells were lysed by a C5 EmulsiFlex High Pressure Homogeniser 86-001 (AVESTIN, Germany). The insoluble material was pelleted by centrifugation (30 minutes at 4000 rpm at 4° C.) and the supernatant (cytoplasmatic fraction) was collected.

To purify the tagged GFP in complex with the hexahistidines-tagged (His-tagged) NbSyn2, a periplasmatic fraction of the His-tagged NbSyn2 was mixed with one cytoplasmatic fraction of each tagged GFP. An IMAC was done as described before. The NbSyn2-GFP tagged fusion complexes were eluted with 1 M imidazol.

Cloning, Expression in E. Coli and Purification of VHH-EPEA-Tagged Fusions

On 1 ng of pMES4, a PCR was performed with Takara Ex Taq polymerase using primers EP138 (5'-ACCCAGGT-CACCGTCTCCTCAGGGTATCAAGACTACGAACCT-GAAGCCTAGTACC CGTACGACGT) (SEQ ID NO:53) and FP (5'-CGCCAGGGTTTTCCCAGTCACGAC-3') (SEQ ID NO:54) to construct pMESy1 (CA2857) and using primers EP139 (5'-ACCCAGGTCACCGTCTCCTCA-GGGGCAGCGGAACCTGAAGCCTAGTACCCGTAC-GACGTTC-3') (SEQ ID NO:55) and FP to construct pMESy2 (CA2741). Amplification conditions were four minutes at 94° C., 28 times (40 seconds at 94° C., 40 seconds at 55° C., one minute at 72° C.) and ten minutes at 72° C. Both PCR products and the pMES4 vector were cut with BamHI and Eco91I and purified. Ligation with T4 DNA polymerase of 100 ng vector to 50 ng PCR product was carried out overnight at 4° C. The mixture was transformed into WK6 cells and grown overnight at 37° C. Analysis was done by PCR using primers MP57 (5'-TTATGCTTCCG-GCTCGTATG-3') (SEQ ID NO:56) and GIII (5'-CCACA-GACAGCCCTCATAG-3') (SEQ ID NO:57) and SpeI digestion. Clones were sequenced and from the correct ones, DNA was prepared (Qiagen).

The Nb458 was amplified using primer RP and primer EP101 (5'-TGAGGGAGACGGTGACCTGGGT-3') (SEQ ID NO:58) with the same amplifications conditions as written above and cloned in the pMESy1 (CA2857) or the pMESy2 (CA2741) vector using the PstI and the Eco9I restriction enzymes. Insert analysis was done by PCR with primers RP and GIII. Expression was done as described by Conrad et al. (2001). Nb458 in pMESy1 is fused to the sequence of the GYQDYEPEA (SEQ ID NO:2) tag and is referred to as CA2944 while in pMESy2, it has the gaaEPEA (SEQ ID NO:8) tag and is referred to as CA2945.

NbSyn2 Affinity Column Purification

Purified His-tagged NbSyn2 was coupled to a CNBr-activated sepharose (GE Health Care Life Science) following the manufacturer's instructions. The column was equilibrated with 50 mM TrisHCl pH7.5. Lysate of tagged fusions (GFP or VHH) was brought onto the beads for 1 hour. The column was washed with 10 column volumes (cv) of 50 mM TrisHCl pH7.5 and elution was performed with 10 cv of 50 mM TrisHCl with extra compounds (see Examples), all pH7.5. In the last experiments, elution buffer was either 50 mM TrisHCl pH7.5 with 1 M or 2 M NaCl, 50 mM Tris-HCl pH7.5 with 0.5 M adipic acid or Tris-HCl pH7.5 with 750 μM of peptide (GYQDYEPEA (SEQ ID NO:2)).

Solid Phase ELISA with His-Tagged NbSyn2

Maxisorp™ 96-well plates (Nunc) were coated with Nb458-gaaEPEA (SEQ ID NO:8) or Nb458-GYQDYEPEA (SEQ ID NO:2) preparations overnight at 4° C. at 2 µg/ml in sodium bicarbonate buffer pH 8.2. Residual protein binding sites in the wells were blocked for two hours at room temperature with 2% milk in PBS. NbSyn2-His6tagged was added at 2 µg/ml in PBS with 0.2% milk. Detection of NbSyn2 Nanobodies™ was performed with a mouse anti-histidine-tag (Serotec). Subsequent detection of the mouse anti-his antibody was done with an alkaline phosphatase anti-mouse-IgG conjugate (Sigma). The absorption at 405 nm was measured 15 minutes after adding the enzyme substrate p-nitrophenyl phosphate.

Solid Phase ELISA, Western Blot with NbSyn2 Conjugated to Alkaline Phosphatase 0.5 mg of His-tagged NbSyn2 in PBS was conjugated with 2.5 mg of alkaline phosphatase in a final volume of 0.5 ml as described by Harlow & Lane (1988). Maxisorb 96-well plates (Nunc) were coated with protein preparations overnight at 4° C. with 2 ug/ml in sodium bicarbonate buffer pH 8.2. SDS-PAGE and Western blot were done according to standard protocols. Residual protein binding sites in the wells or on the membranes were blocked for two hours at room temperature with 2% milk in PBS. Detection of the tags was performed with a dilution of 1/1000 NbSyn2-AP conjugate. For ELISA, the absorption at 405 nm was measured 15 to 30 minutes after adding the enzyme substrate p-nitrophenyl phosphate. For Western blot, NBT/BCIP substrate (Roche) was used as described by the manufacturer.

Crystallization of the NbSyn2-Peptide Complex

Crystallization of the NbSyn2 complexed with a synthetic peptide (sequence NH2-GYQDYEPEA-COOH (SEQ ID NO:2)) (BIO-SYNTHESIS, INC., Texas) was achieved using a crystallization robot Phoenix (Art Robbins Instruments) and a sitting drop vapor diffusion assay. 133 µl of 10 mg/ml of NbSyn2 was first mixed with 15 µl of peptide (at 20 mg/ml) before dispension in a JB Classic 1-4 (G10) screen (Jena Biosciences). 100 nl drops were mixed with 100 nl of the precipitant solution. Crystals were obtained under the following conditions: 25% w/v PEG 6000, 100 mM HEPES, pH 7.5 and 100 mM LiCl. Crystals were subsequently harvested and transferred in a cryo-protectant solution (25% w/v PEG 6000, 100 mM HEPES, pH 7.5 and 100 mM LiCl and 10% PEG400) and flash-frozen in liquid nitrogen for data collection.

Data Collection and Structure Solution

Diffraction patterns for frozen crystals of the NbSyn2-peptide complex were obtained at the X11 beam line equipped with a MAR555 detector, at the European Molecular Biology Laboratory (EMBL) using the Deutsches Elektronen Synchrotron (DESY Hamburg, Germany). Data were processed using Mosflm65, and Pointless and Scala were used to determine the space group and scale and merge the data, respectively. Molecular replacement using the program Phaser66 and a model for NbSyn2, namely, pdb entry 1HCV67, was used to obtain the phase information associated with the structure factors. Model building and refinement were achieved using the programs Arp/Warp68 and Refrnac569. The graphics program Coot70 was used to interpret the electron density maps and for refinement of the model. The change in solvent-accessible surface area (ASA) upon the formation of the NbSyn2:α-synuclein complex was calculated using web-based server PROTORP71.

Cloning of the Long (GYQDYEPEA (SEQ ID NO:2)) and Short (EPEA (SEQ ID NO:1)) Tag for Expression in HeLa Cells The two different tags GYQDYEPEA (SEQ ID NO:2) and EPEA (SEQ ID NO:1) were C-terminal fused to Rev by PCR using Takara Ex Taq polymerase (TAKARA BIO INC). A PCR was performed on pcDNARev-mKO1 (kindly given to us by Dirk Daekenans) with primer T7 (5'-ATTAATAC-GACTCACTATAGG-3') (SEQ ID NO:59) and primer EP136 (5'-TCGAGCGGCCGCTTAGGCTTCAGGTTCG-TAGTCTTGATACCCTGAAGCTCCTGCACCATTCTC-3') (SEQ ID NO:60) to amplify the rev gene fused to the DNA sequence of GYQDYEPEA (SEQ ID NO:2) at the C-terminus. To fuse the EPEA (SEQ ID NO:1) tag to Rev, primers T7 and EP176 (5'-TCGAGCGGCCGCTTAGGCT-TCAGGTTCAGCTCCTGCACCATTCTC-3') (SEQ ID NO:61) were used. Amplification conditions were two minutes at 94° C., 25 times (30 seconds at 94° C., 30 seconds at 52° C., one minute 72° C.) and ten minutes at 72° C. The amplified DNA fragments were cut with KpnI and NotI and ligated into the pcDNA3.1 vector. The ligation product was electroporated into E. coli Top10. Clones were analyzed by PCR and sequence analysis. At the same time, both tags were also fused to GFP as described above, using primer EP180 (5'-GCTTGGTACCTCATGAGCAAAGGA-GAAGAAC-3') (SEQ ID NO:62) and primer EP126 (5'-TTCGAATTCATTACGCT-TCCGGTTCATAATCCTGA-TATCCTTTGTAGAGCTCATCCATGC-3') (SEQ ID NO:63) to fuse it to the GYQDYEPEA (SEQ ID NO:2) and primer EP180 and primer EP181 (5'-TTCGAATTCAT-TACGCTTCCGGTTCT-GCGGCTCCTTTGTAGA-GCT-CATCCATGCC-3') (SEQ ID NO:64) to fuse GFP to EPEA (SEQ ID NO:1). The amplified DNA fragments were cut with KpnI and EcoRI and ligated into the pcDNA3.1 vector. The ligation product was then electroporated into E. coli Top10, and clones were analyzed by PCR and sequence analysis.

Transfection of HeLa Cells

HeLa, human epithelial cells were maintained using standard procedures until confluent in DMEM medium with 10% fetal calf serum. For transfection of plasmid DNA in HeLa, cells were harvested by a Trypsin/EDTA treatment, counted and plated onto glass bottom microwell dishes (MatTek corporation). Transfections were preformed according to manufacturer's manual: the $4 \times 10^5$ cells were seeded in a 35 mm dish. 1.2 µg DNA, or in the case where two different plasmids are cotransfected twice, 1 µg is mixed with 4.5 µl transfect (Qiagen, Valencia, Calif.), dropped onto the cells and incubated overnight.

Confocal Microscopy

Transfected HeLa cells were imaged with a laser scanning SP5 confocal microscope (Leica Microsystems) equipped with an AF 6000 microscope and an AOBS, using a HCX PL APO×63 (NA 1.2) water immersion objective magnification. GFP was monitored with the Ar laser using the 488-nm line for excitation, and emission was detected between 492 and 570 nm. mKusabira orange fluorescent protein (mKO) was imaged using the DPSS-561 nm laser for excitation, and emission was detected between 570 and 675 nm.

Cloning, Expression in E. Coli and Purification of Bivalent biNbSyn2

On 2 ng of the pHen6(c)NbSyn2 vector (EP358), two different PCRs were performed with kapa Taq polymerase using once primer SM17 (5'-CGCGGCCCAGCCGGC-CATGGCT-GATGTGCAGCTGGTG-GAGTCTGG-3') (SEQ ID NO:73) and primer VHH1-reverse-5GS-BamHI (5'-AGTAGGATCCGCCACCTCCTGAGGAGACCGT-GACCTGGGT-3') (SEQ ID NO:74) and once primer VHH2-forward-4GS-BamHI (5'-TCTTGGATCCGGCG-GAGGTAGTCAGGTGCAGCTGCAG- GAGTCTGGGGGAGG-3') (SEQ ID NO:75) and primer VHH2-reverse-TVSS-BsteII (5'-TGAGGAGACGGTGAC-CTGGGT-3') (SEQ ID NO:76) to amplify the NbSyn2 gene. Amplification conditions were four minutes at 94° C., 28 times (40 seconds at 94° C., 40 seconds at 55° C., one minute at 72° C.) and ten minutes at 72° C. The PCR product generated by using primer SM17 and VHH1-reverse-5GS-BamHI was cut with NcoI and BamHI, the second PCR product generated by using primers VHH2-forward-4GS-BamHI and VHH2-reverse-TVSS-BsteII was cut with BamHI and Eco91I. The pMES4 vector was cut with NcoI and BamHI and Eco91I. All digests were purified and the DNA concentration was measured. A three-point ligation with T4 DNA polymerase of 100 ng vector to 30 ng of both PCR products was carried out in 10 µl for two hours at room temperature. The mixture was diluted and cut with XbaI to eliminate the self-ligated vectors. The digest was purified and transformed into WK6 cells and grown overnight at 37° C. Analysis was done by PCR using primers MP57 (5'-TTATGCTTCCGGCTCGTATG-3') (SEQ ID NO:56) and GIII (5'-CCACAGACAGCCCTCATAG-3') (SEQ ID NO:57) and BamHI digestion. From the clones that had the correct PCR fragment size containing a BamHI site, the PCR fragment was sequenced, and from a correct plasmid, DNA was prepared (Qiagen) and referred to as pMES4biNbSyn2 (CA4394).

Expression and purification was done as described by Conrad et al. (2001). After IMAC purification, the sample was concentrated and ran on preparative superdex75 size exclusion column to separate the bivalent biNbSyn2 from contaminants or degradation products.

Solid Phase ELISA with biNbSyn2 Conjugated to Alkaline Phosphatase 0.66 mg of His-tagged biNbSyn2 in PBS was conjugated to 1.7 mg of alkaline phosphatase; in a parallel experiment, 0.33 mg of the monovalent NbSyn2 was conjugated to 1.7 mg of alkaline phosphatase. In both cases, the final volume was 0.33 ml and the conjugation occurred as described by Harlow & Lane (1988). Maxisorb 96-well plates (Nunc) were coated with 100 µl protein preparations overnight at 4° C. in sodium bicarbonate buffer pH 8.2 at a concentration of 1 µg/ml or 0.1 µg/ml. Residual protein binding sites in the wells were blocked for two hours at room temperature with 2% milk in PBS. Detection of the tags was performed with a dilution of 1/250 to 1/4000 of both NbSyn2-AP conjugate and biNbsyn2-AP conjugate. For ELISA, the absorption at 405 nm was measured 60 minutes after adding the enzyme substrate p-nitrophenyl phosphate and after overnight incubation.

Cloning, Expression in *E. Coli* of the CsgG Membrane Protein and its Detection/Purification To replace the C-terminal His tag of CsgG with a sequence encoding GGEPEA (SEQ ID NO:70), the pMC2 plasmid was used in the SLIM method (Chiu et al. 2004) with the following primers: 5'-GGCGGCGAACCG-GAAGCGTGACTGCAGGCATGCAAGCTTGGCT-3' (SEQ ID NO:77), 5'-TGACTGCAGGC-ATGCAAGCTTG-GCT-3' (SEQ ID NO:78), 5'-CGCTTCCGGTTCGCCGC-CATGGTGATGGTGATGGTGGGATTCC-3' (SEQ ID NO:79), and 5'-ATGGTGATGGTGATGGTGGGATTCC 3'(SEQ ID NO:80). PCR and sequence analysis confirmed the correct replacement. To confirm the expression of the CsgG protein, four different clones of the same construct were picked and a 25 ml *E. coli* culture was grown and induced. Cells were harvested and separated by SDS-PAGE and transferred to nitrocellulose membranes. The blot was blocked with 2% milk and washed five times with 20 ml PBS/TWEEN®. NbSyn2-AP conjugate (monovalent) was diluted 1 in 500 in 0.2% milk in PBS and shaken for one hour. The blot was washed five more times and developed with NBT/BCIP substrate (Roche) as described by the manufacturer.

To purify the expressed EPEA (SEQ ID NO:1)-tagged CsgG, 110 g of frozen cell pellet was resuspended in 330 ml 50 mM Tris, 150 mM NaCl, 1 mM DTT, 1 mM EDTA pH8.0. 20 µg DNase/1 g pellet and 0.1 mg lysozyme/ml buffer was added. Cells were lysed by the French press and the cell debris was removed by a short centrifugation step (7,500 g for twelve minutes at 4° C.). The supernatant was then centrifuged at high speed to recover the membranes (100000 g for 50 minutes at 4° C.). Membranes were homogenized in 100 ml 25 mM Tris, 150 mM NaCl, 1 mM DTT, 1 mM EDTA pH8.0 with 0.5% sarcosine. The suspension was centrifuged at high speed (100000 g for 50 minutes at 4° C.) and the pellet (=outer membranes) was collected. The pellet was resuspended in 100 ml 25 mM Tris, 150 mM NaCl, 1 mM DTT, 1 mM EDTA pH8.0 with 2 mM LDAO using a homogenizer. After centrifugation, the pellet (membranes) was washed by resuspending in 50 ml 25 mM Tris, 150 mM NaCl, 1 mM DTT, 1 mM EDTA pH8.0 with 0.002% DDM. Suspension was centrifuged (100000 g for 50 minutes at 4° C.) to collect the outer membranes. These were resuspended in 100 ml 25 mM Tris, 150 mM NaCl, 1 mM DTT and 1% DDM and left to shake overnight at 4° C. to solubilize the membranes. One last centrifugation step (100000 g for 50 minutes at 4° C.) was done to remove the insoluble parts: the supernatant was run over a small column containing the 1 ml CNBr—NbSyn2 cross-linked to Sepharose-beads as described in Example 4. The beads were washed with 5 ml 25 mM Tris pH8, 1 mM DTT, 0.02% DDM, 1% C8E4, 5 mM LDAO. The elution of bound protein was done with two times 1 ml 25 mM Tris pH8, 150 mM NaCl, 1 mM DTT, 0.02% DDM containing 750 µM of the small synthetic $NH_2$—SEPEA-COOH (SEQ ID NO:71) peptide.

REFERENCES

Ausubel et al. (1992). *Current Protocols in Molecular Biology*, Greene/Wiley, New York, N.Y.

Ausubel F. M., R. Brent, R. E. Kingston, D. D. Moore, J. G. Seidman, J. A. Smith, and K. Struhl (2007). *Current Protocols in Molecular Biology*, John Wiley and Sons, Inc.

Bermel W., I. Bertini, I. C. Felli, Y. M. Lee, C. Luchinat, and R. Pierattelli (2006). Protonless NMR experiments for sequence-specific assignment of backbone nuclei in unfolded proteins. *J. Am. Chem. Soc.* 128:3918-9.

Brizzard B. L., R. G. Chubet, and D. L. Vizard (1994). Immunoaffinity purification of FLAG epitope-tagged bacterial alkaline phosphatase using a novel monoclonal antibody and peptide elution. *BioTechniques* 16:730-735.

Brizzard B. (2008). Epitope Tagging. *BioTechniques* 44:693-695 (25th Anniversary Issue, April 2008).

Chiu J., P. E. March, R. Lee and D Tillett (2004). Site-directed, Ligase-Independent Mutagenesis (SLIM): a single-tube methodology approaching 100% efficiency in four hours. *Nucleic Acids Res.* 32:e174.

Chomczynski P. and N. Sacchi (1987). Single-step method of RNA isolation by acid guanidium thiocyanate-phenol-chloroform extraction. *Anal. Biochem.* 162:156.

Chong S., F. B. Mersha, D. G. Comb, M. E. Scott, D. Landry, L. M. Vence, F. B. Perler, J. Benner, et al. (1997). Single-column purification of free recombinant proteins using self-cleavable affinity tag derived from a protein splicing element. *Gene* 192:271-281.

Conrath K. E., M. Lauwereys, M. Galleni, A. Matagne, J. M. Frere, J. Kinne, L. Wyns, and S. Muyldermans (2001). Beta-lactamase inhibitors derived from single-domain antibody fragments elicited in the camelidae. *Antimicrob. Agents Chemother.* 45:2807-12.

Conrath K. E., U. Wernery, S. Muyldermans and V. K. Nguyen (2003). Emergence and evolution of functional heavy-chain antibodies in Camelidae. *Dev. Comp. Immunol.* 27:87-103.

Davis et al. (1999). New fusion protein systems designed to give soluble expression in Escherichia coli. *Biotechnol. Bioeng.* 65:382-388.

Dedmon M. M., J. Christodoulou, M. R. Wilson and C. M. Dobson (2005a). Heat shock protein 70 inhibits alpha-synuclein fibril formation via preferential binding to prefibrillar species. *J. Biol. Chem.* 280:14733.

Dedmon M. M., K. Lindorff-Larsen, J. Christodoulou, M. Vendruscolo, and C. M. Dobson (2005b). Mapping long-range interactions in alpha-synuclein using spin-label NMR and ensemble molecular dynamics simulations. *J. Am. Chem. Soc.* 127:476-7.

Desmyter A., T. R. Transue, M. A. Ghahroudi, M. H. Thi, F. Poortmans, R. Hamers, S. Muyldennans, and L. Wyns (1996). Crystal structure of a camel single-domain VH antibody fragment in complex with lysozyme. *Nat. Struct. Biol.* 3:803-11.

di Guan C., P. Li, P. D. Riggs, and H. Inouye (1988). Vectors that facilitate the expression and purification of foreign peptides in Escherichia coli by fusion to maltose-binding protein. *Gene* 67:21-30.

Evan G. I., G. K. Lewis, G. Ramsay, and J. M. Bishop (1985). Isolation of monoclonal antibodies specific for human c-myc proto-oncogene product. *Mol. Cell. Biol.* 5:3610-3616.

Field J., J. Nikawa, D. Broek, B. MacDonald, L. Rodgers, I. A. Wilson, R. A. Lerner, and M. Wigler (1988). Purification of RAS-responsive adenylyl cyclase complex from Saccharomyces cerevisae by use of an epitope addition method. *Mol. Cell. Biol.* 8:2159-2165.

Ghahroudi M. A., A. Desmyter, L. Wyns, R. Hamers, and S. Muyldermans (1997). Selection and identification of single domain antibody fragments from camel heavy-chain antibodies. *FEBS Lett* 414:521-526.

Giliams T, E. Degenst and C. M. Dobson (2010). "Nanobodies to Investigate the Mechanisms Underlying the α-Synuclein Related Parkinson's Disease." First year report.

Gloeckner C. J., K. Boldt, A. Schumacher, R. Roepman, and M. Ueffing (2007). A novel tandem affinity purification strategy for the efficient isolation of native protein complexes. *Proteomics* 7:4228-4234.

Hackbarth J. S., S. H. Lee, X. W. Meng, B. T. Vroman, S. H. Kaufmann, and L. M. Karnitz (2004). S-peptide epitope tagging for protein purification, expression monitoring, and localization in mammalian cells. *BioTechniques* 37:835-839.

Hamers-Casterman C., T. Atarhouch, S. Muyldermans, G. Robinson C. Hamers, E. G. Songa, N. Bendahman and R. Hamers (1993). Naturally occurring antibodies devoid of light chains. *Nature* 363:446-8.

Harlow E. and D. P. Lane (1988). *Antibodies: A Laboratory Manual* (Cold Spring Harbor Laboratory, Cold Spring Harbor, N.Y.).

Hochuli E., W. Bannwarth, H. Dobeli, R. Gentz, and D. Stuber (1988). Genetic approach to facilitate purification of recombinant proteins with a novel metal chelate. *Bio-Technology* 6:1321-1325.

Hopp et al. "A short polypeptide marker sequence useful for recombinant protein identification and purification," *Nature Biotechnology* 6:1204-1210 (1988).

Jarvik J. W. and C. A. Telmer (1998). Epitope tagging. *Annu. Rev. Genet.* 32:601-618.

Kapust R. B and D. S. Waugh (1999). Escherichia coli maltose-binding protein is uncommonly effective at promoting the solubility of polypeptides to which it is fused. *Protein Sci.* 1668-1674.

Kaufmann M., P. Linder, A. Honegger, K. Blank, M. Tschopp, G. Capitani, A. Pluckthun, and M. G. Grutter (2002). Crystal structure of the anti-His tag antibody 3D5 single-chain fragment complexed to its antigen. *J. Mol. Biol.* 318:135-147.

Kim T. D., S. R. Paik, and C. H. Yang (2002). Structural and functional implications of C-terminal regions of alpha-synuclein. *Biochemistry* 41(46):13782-90.

Kimple M. E., and J. Sondek (2004). Overview of affinity tags for protein purification. *Curr. Protoc. Protein Sci.* 2004 September; Chapter 9:Unit 9.9.

Kohler and Milstein (1975). *Nature* 256:495-497.

Korotkov K. V., E. Pardon, J. Steyaert, and W. G. Hol (2009). Crystal structure of the N-terminal domain of the secretin GspD from ETEC determined with the assistance of a nanobody. *Structure* 17:255-265.

Lauwereys M., M. Arbabi Ghahroudi, A. Desmyter, J. Kinne, W. Hölzer, E. De Genst, L. Wyns, and S. Muyldermans (1998). Potent enzyme inhibitors derived from dromedary heavy-chain antibodies. *EMBO J.* 17:3512-3520.

Lefranc M. P., E. Duprat, Q. Kaas, M. Tranne, A. Thiriot, and G. Lefranc (2005). IMGT unique numbering for MHC groove G-DOMAIN and MHC superfamily (MhcSF) G-LIKE-DOMAIN. *Dev. Comp. Immunol.* 29:917-38.

Li Y (2010). Commonly used tag combinations for tandem affinity purification. *Biotechnol. Appl. Biochem.* 55:73-83.

Lichty J. J. et al. (2005). *Protein Expression and Purification* May 2005, 41:98-105.

Loris R., I. Marianovsky, J. Lah, T. Laeremans, H. Engelberg-Kulka, G. Glaser, S. Muyldermans, and L. Wyns (2003). Crystal structure of the intrinsically flexible addiction antidote MazE. *J. Biol. Chem.* 278:28252-28257.

Maniatis et al. (1982). *Molecular Cloning: A Laboratory Manual; DNA Cloning: A Practical Approach*, volumes I and II (Glover, ed.).

Metzger et al. (1988). *Nature* 334:31-36.

Park S. M., H. Y. Jung, T. D. Kim, J. H. Park, C. H. Yang, and J. Kim (2002), Distinct roles of the N-terminal-binding domain and the C-terminal-solubilizing domain of alpha-synuclein, a molecular chaperone. *J. Biol. Chem.* 277(32):28512-20.

Perkins A., A. W. Cochrane, S. M. Ruben, and C. A. Rosen (1989). Structural and functional characterization of the human immunodeficiency virus rev protein. *J. Acquir. Immune Defic. Syndr.* 2:256-263.

Puig O., F. Caspary, G. Rigaut, B. Rutz, E. Bouveret, E. Bragado-Nilsson, M. Wilm, and B. Séraphin (2001). The tandem affinity purification (TAP) method: a general procedure of protein complex purification. *Methods* 24:218-29.

Rigaut G., A. Shevchenko, B. Rutz, M. Wilm, M. Mann, and B. Seraphin (1999). A generic protein purification method for protein complex characterization and proteome exploration. *Nat. Biotechnol.* 17:1030-1032.

Rivers R. C., J. R. Kumita, G. G. Tartaglia, M. M. Dedmon, A. Pawar, M. Vendruscolo, and C. M. Dobson, J. Christodoulou (2008). Molecular determinants of the aggregation behavior of alpha- and beta-synuclein. *Protein Sci.* 17:887-98.

Robinson L. S., E. M. Ashman, S. J. Hultgren, and M. R. Chapman (2006). Secretion of curli fibre subunits is mediated by the outer membrane-localized CsgG protein. *Mol. Microbiol.* 59:870-81.

Saerens D., G. H. Ghassabeh, and S. Muyldermans (2008). Single-domain antibodies as building blocks for novel therapeutics. *Curr. Opin. Pharmacol.* 8:600-8.

Sambrook et al. (1989). *Molecular Cloning: A Laboratory Manual*, 2nd Ed., Cold Spring Harbor, N.Y.: Cold Spring Harbor Laboratory Press, pp. 16.30-16.55.

Schmidt T. G. M. and A. Skerra (2007). The Streptag system for one-step purification and high-affinity detection or capturing of proteins. *Nat. Protocols* 2:1528-1535.

Smith M. C., T. C. Fuinian, T. D. Ingolia, C. Pidgeon (1988). *J. Biol. Chem.* 263:7211-7215.

Tucker J. and R. Grisshammer (1996). Purification of a rat neurotensin receptor expressed in *Escherichia coli*. *Biochem. J.* 317:891-899.

Uhlén M., B. Nilsson, B. Guss, M. Lindberg, S. Gatenbeck, and L. Philipson (1983). Gene fusion vectors based on the gene for staphylococcal protein A. *Gene* 23:369-378.

Van Leene J. et al. (2008). Boosting tandem affinity purification of plant protein complexes. *Trends in plant science* 13:517-520.

Van Leene J. et al. (2010). Targeted interactomics reveals a complex core cell cycle machinery in *Arabidopsis thaliana*. *Mol. Syst. Biol.* 6:397.

Vuchelen A., E. O'Day, E. De Genst, E. Pardon, L. Wyns, M. Dumoulin, C. M. Dobson, J. Christodoulou and S. T. Hsu (2009). (1)H, (13)C and (15)N assignments of a camelid nanobody directed against human alpha-synuclein. *Biomol. NMR Assign.* 3:231-3.

Watson J. D. et al. (1992). *Recombinant DNA* 2nd Ed., New York: W. H. Freeman and Co.

Waugh D. (2005). Making the most of affinity tags. *Trends in Biotechnology* 23:316-320.

Winnacker E. (1987). From *Genes to Clones*, New York: VCH Publishers.

Wu (1993). *Molecular Cloning*, Cold Spring Harbor Laboratory, Plainview, N.Y.

Y-B. Zhang et al. (2004). Protein aggregation during overexpression limited by peptide extensions with large net negative charge. *Protein Expr. Purif.* 36:207-216.

Zell R H. J. Fritz (1987). DNA mismatch-repair in *Escherichia coli* counteracting the hydrolytic deamination of 5-methyl-cytosine residues. *EMBO J.* 6:1809-1815.

---

The invention claimed is:

1. A method for purifying a non-naturally occurring fusion protein comprising (i) an epitope tag consisting of SEQ ID NO:1 and (ii) a target protein, the method comprising:

a) applying a solution containing the non-naturally occurring fusion protein to a solid support possessing an immobilized affinity ligand that binds to an epitope tag consisting of SEQ ID NO:1, wherein the solid support is a column or a bead, and wherein the affinity ligand is an antibody, antibody fragment, or single-domain antibody;

b) forming a complex between the immobilized affinity ligand and the non-naturally occurring fusion protein;

c) removing weakly bound or unbound molecules; and d) eluting bound molecules.

2. The method of claim 1, wherein the solid support is a bead.

3. A method for immobilizing and/or capturing a non-naturally occurring fusion protein on a solid support, wherein the non-naturally occurring fusion protein comprises (i) an epitope tag consisting of SEQ ID NO:1 and (ii) a target protein, the method comprising:
   a) applying a solution containing a non-naturally occurring fusion protein to a solid support possessing an immobilized affinity ligand that binds to an epitope tag consisting of SEQ ID NO:1, wherein the solid support is a column or a bead, and wherein the affinity ligand is an antibody, antibody fragment, or single-domain antibody;
   b) forming a complex between the immobilized affinity ligand and the fusion protein; and
   c) removing weakly bound or unbound molecules.

4. The method of claim 3, wherein the solid support is a bead.

5. The method of claim 3, wherein the solid support is a column.

6. The method of claim 1, wherein the solid support is a column.

* * * * *

UNITED STATES PATENT AND TRADEMARK OFFICE
CERTIFICATE OF CORRECTION

Page 1 of 1

PATENT NO. : 9,518,084 B2
APPLICATION NO. : 13/698624
DATED : December 13, 2016
INVENTOR(S) : Els Pardon, Jan Steyaert and Lode Wyns It is certified that error appears in the above-identified patent and that said Letters Patent is hereby corrected as shown below:

On the Title Page
In Item (75) Inventors:    change "Lubbeck (BE);" to --Wezemaal (BE);--
In Item (73) Assignees:    change "Brussels (BE)" to --Brussel (BE)--

In the Specification
Column 12,   Line 28,   change "hereof Antibodies" to --hereof. Antibodies--
Column 21,   Line 30,   change "the N-temiinal part" to --the N-terminal part--
Column 24,   Line 23,   change "the C-teriminal" to --the C-terminal--
Column 30,   Line 60,   change "for $^{15}N^{13}C$-labeled" to --$^{15}N$ $^{13}C$-labeled--
Column 31,   Line 9,    change "for $^{15}N^{13}C$-labeled" to --$^{15}N$ $^{13}C$-labeled--
Column 33,   Line 60,   change "Refrnac569." to --Refmac569.--
Column 37,   Line 29,   change "S. Muyldennans," to --S. Muyldermans,--
Column 39,   Line 25,   change "T. C. Fuinian," to --T. C. Furman,--

Signed and Sealed this
Eighteenth Day of April, 2017

Michelle K. Lee
*Director of the United States Patent and Trademark Office*

SEQUENCE LISTING

```
<160> NUMBER OF SEQ ID NOS: 81

<210> SEQ ID NO 1
<211> LENGTH: 4
<212> TYPE: PRT
<213> ORGANISM: Artificial Sequence
<220> FEATURE:
<223> OTHER INFORMATION: Epitope tag

<400> SEQUENCE: 1

Glu Pro Glu Ala
1

<210> SEQ ID NO 2
<211> LENGTH: 9
<212> TYPE: PRT
<213> ORGANISM: Artificial Sequence
<220> FEATURE:
<223> OTHER INFORMATION: Synthetic peptide

<400> SEQUENCE: 2

Gly Tyr Gln Asp Tyr Glu Pro Glu Ala
1               5

<210> SEQ ID NO 3
<211> LENGTH: 6
<212> TYPE: PRT
<213> ORGANISM: Artificial Sequence
<220> FEATURE:
<223> OTHER INFORMATION: alfa-synuclein

<400> SEQUENCE: 3

Asp Tyr Glu Pro Glu Ala
1               5
```

```
<210> SEQ ID NO 4
<211> LENGTH: 8
<212> TYPE: PRT
<213> ORGANISM: Artificial Sequence
<220> FEATURE:
<223> OTHER INFORMATION: Tag

<400> SEQUENCE: 4

Tyr Gln Asp Tyr Glu Pro Glu Ala
1               5

<210> SEQ ID NO 5
<211> LENGTH: 7
<212> TYPE: PRT
<213> ORGANISM: Artificial Sequence
<220> FEATURE:
<223> OTHER INFORMATION: Tag

<400> SEQUENCE: 5

Gln Asp Tyr Glu Pro Glu Ala
1               5

<210> SEQ ID NO 6
<211> LENGTH: 8
<212> TYPE: PRT
<213> ORGANISM: Artificial Sequence
<220> FEATURE:
<223> OTHER INFORMATION: Tag

<400> SEQUENCE: 6

Gly Tyr Gln Asp Tyr Glu Pro Glu
1               5

<210> SEQ ID NO 7
<211> LENGTH: 12
<212> TYPE: PRT
<213> ORGANISM: Artificial Sequence
<220> FEATURE:
<223> OTHER INFORMATION: 14N 12-residue peptide

<400> SEQUENCE: 7

Ser Glu Glu Gly Tyr Gln Asp Tyr Glu Pro Glu Ala
1               5                   10

<210> SEQ ID NO 8
<211> LENGTH: 7
<212> TYPE: PRT
<213> ORGANISM: Artificial Sequence
<220> FEATURE:
<223> OTHER INFORMATION: Tag

<400> SEQUENCE: 8

Gly Ala Ala Glu Pro Glu Ala
1               5

<210> SEQ ID NO 9
<211> LENGTH: 8
<212> TYPE: PRT
<213> ORGANISM: Artificial Sequence
<220> FEATURE:
<223> OTHER INFORMATION: Tag

<400> SEQUENCE: 9

Gly Ala Gly Ala Glu Pro Glu Ala
1               5

<210> SEQ ID NO 10
```

```
<211> LENGTH: 13
<212> TYPE: PRT
<213> ORGANISM: Artificial Sequence
<220> FEATURE:
<223> OTHER INFORMATION: Tag

<400> SEQUENCE: 10

Gly Ala Gly Ala Gly Tyr Gln Asp Tyr Glu Pro Glu Ala
1               5                   10

<210> SEQ ID NO 11
<211> LENGTH: 5
<212> TYPE: PRT
<213> ORGANISM: Artificial Sequence
<220> FEATURE:
<223> OTHER INFORMATION: Peptide table 5

<400> SEQUENCE: 11

Tyr Glu Pro Glu Ala
1               5

<210> SEQ ID NO 12
<211> LENGTH: 4
<212> TYPE: PRT
<213> ORGANISM: Artificial Sequence
<220> FEATURE:
<223> OTHER INFORMATION: Short linker sequence

<400> SEQUENCE: 12

Gly Ala Gly Ala
1

<210> SEQ ID NO 13
<211> LENGTH: 6
<212> TYPE: PRT
<213> ORGANISM: Artificial Sequence
<220> FEATURE:
<223> OTHER INFORMATION: Linker sequence

<400> SEQUENCE: 13

Glu Glu Gly Glu Pro Lys
1               5

<210> SEQ ID NO 14
<211> LENGTH: 6
<212> TYPE: PRT
<213> ORGANISM: Artificial Sequence
<220> FEATURE:
<223> OTHER INFORMATION: Linker sequence

<400> SEQUENCE: 14

Glu Glu Ala Glu Pro Lys
1               5

<210> SEQ ID NO 15
<211> LENGTH: 4
<212> TYPE: PRT
<213> ORGANISM: Artificial Sequence
<220> FEATURE:
<223> OTHER INFORMATION: Protease cleavage site

<400> SEQUENCE: 15

Ile Glu Gly Arg
1

<210> SEQ ID NO 16
<211> LENGTH: 4
```

```
<212> TYPE: PRT
<213> ORGANISM: Artificial Sequence
<220> FEATURE:
<223> OTHER INFORMATION: Thrombin cleavage site

<400> SEQUENCE: 16

Leu Val Pro Arg
1

<210> SEQ ID NO 17
<211> LENGTH: 5
<212> TYPE: PRT
<213> ORGANISM: Artificial Sequence
<220> FEATURE:
<223> OTHER INFORMATION: Enteroskinase cleaving site

<400> SEQUENCE: 17

Asp Asp Asp Asp Lys
1               5

<210> SEQ ID NO 18
<211> LENGTH: 127
<212> TYPE: PRT
<213> ORGANISM: Artificial Sequence
<220> FEATURE:
<223> OTHER INFORMATION: Nanobody Nb_85

<400> SEQUENCE: 18

Gln Val Gln Leu Gln Glu Ser Gly Gly Gly Ser Val Gln Ala Gly Gly
1               5                   10                  15

Ser Leu Arg Leu Ser Cys Ala Ala Ser Gly Leu Thr Tyr Ser Asn Tyr
            20                  25                  30

Cys Met Gly Trp Phe Arg Gln Ala Pro Gly Lys Ala Arg Glu Val Val
        35                  40                  45

Ala Arg Ile Ser Thr Arg Gly Ile Lys Thr Tyr Tyr Ala Asp Ser Val
    50                  55                  60

Asn Gly Arg Phe Thr Ile Ser Arg Asp Asn Ala Lys Asn Met Val Tyr
65                  70                  75                  80

Leu Gln Met Asn Ser Leu Lys Pro Glu Asp Thr Ala Ile Tyr Tyr Cys
                85                  90                  95

Ala Ala Val Ile Tyr Pro Gly Tyr Gly Asp Ser Cys Pro Trp Thr Thr
            100                 105                 110

Ser Val Asn Tyr Trp Gly Gln Gly Thr Gln Val Thr Val Ser Ser
        115                 120                 125

<210> SEQ ID NO 19
<211> LENGTH: 127
<212> TYPE: PRT
<213> ORGANISM: Artificial Sequence
<220> FEATURE:
<223> OTHER INFORMATION: Nanobody Nb_88

<400> SEQUENCE: 19

Gln Val Gln Leu Gln Glu Ser Gly Gly Gly Leu Val Gln Pro Gly Gly
1               5                   10                  15

Ser Leu Arg Leu Ser Cys Ala Ala Ser Gly Tyr Thr Tyr Ser Arg Ile
            20                  25                  30

Cys Met Gly Trp Phe Arg Gln Ala Pro Gly Lys Ala Arg Glu Val Val
        35                  40                  45

Ala Arg Ile Ser Thr Arg Gly Ile Lys Thr Tyr Tyr Ala Asp Ser Val
    50                  55                  60
```

Asn Gly Arg Phe Thr Ile Ser Arg Asp Asn Ala Lys Asn Met Val Tyr
65                  70                  75                  80

Leu Gln Met Asn Ser Leu Lys Pro Glu Asp Thr Ala Ile Tyr Tyr Cys
                85                  90                  95

Ala Ala Val Ile Tyr Pro Gly Tyr Gly Asp Ser Cys Pro Trp Thr Thr
            100                 105                 110

Ser Val Asn Tyr Trp Gly Gln Gly Thr Gln Val Thr Val Ser Ser
            115                 120                 125

<210> SEQ ID NO 20
<211> LENGTH: 126
<212> TYPE: PRT
<213> ORGANISM: Artificial Sequence
<220> FEATURE:
<223> OTHER INFORMATION: Nanobody Nb_Syn2 PstI

<400> SEQUENCE: 20

Gln Val Gln Leu Gln Glu Ser Gly Gly Gly Ser Val Gln Ala Gly Gly
1               5                   10                  15

Ser Leu Arg Leu Ser Cys Ala Ala Ser Gly Ile Asp Ser Ser Ser Tyr
            20                  25                  30

Cys Met Gly Trp Phe Arg Gln Arg Pro Gly Lys Glu Arg Glu Gly Val
        35                  40                  45

Ala Arg Ile Asn Gly Leu Gly Gly Val Lys Thr Ala Tyr Ala Asp Ser
    50                  55                  60

Val Lys Asp Arg Phe Thr Ile Ser Arg Asp Asn Ala Glu Asn Thr Val
65                  70                  75                  80

Tyr Leu Gln Met Asn Ser Leu Lys Pro Glu Asp Thr Ala Ile Tyr Tyr
                85                  90                  95

Cys Ala Ala Lys Phe Ser Pro Gly Tyr Cys Gly Gly Ser Trp Ser Asn
            100                 105                 110

Phe Gly Tyr Trp Gly Gln Gly Thr Gln Val Thr Val Ser Ser
            115                 120                 125

<210> SEQ ID NO 21
<211> LENGTH: 126
<212> TYPE: PRT
<213> ORGANISM: Artificial Sequence
<220> FEATURE:
<223> OTHER INFORMATION: Nanobody Nb_Syn2

<400> SEQUENCE: 21

Gln Gly Gln Leu Val Glu Ser Gly Gly Gly Ser Val Gln Ala Gly Gly
1               5                   10                  15

Ser Leu Arg Leu Ser Cys Ala Ala Ser Gly Ile Asp Ser Ser Ser Tyr
            20                  25                  30

Cys Met Gly Trp Phe Arg Gln Arg Pro Gly Lys Glu Arg Glu Gly Val
        35                  40                  45

Ala Arg Ile Asn Gly Leu Gly Gly Val Lys Thr Ala Tyr Ala Asp Ser
    50                  55                  60

Val Lys Asp Arg Phe Thr Ile Ser Arg Asp Asn Ala Glu Asn Thr Val
65                  70                  75                  80

Tyr Leu Gln Met Asn Ser Leu Lys Pro Glu Asp Thr Ala Ile Tyr Tyr
                85                  90                  95

Cys Ala Ala Lys Phe Ser Pro Gly Tyr Cys Gly Gly Ser Trp Ser Asn
            100                 105                 110

Phe Gly Tyr Trp Gly Gln Gly Thr Gln Val Thr Val Ser Ser
            115                 120                 125

<210> SEQ ID NO 22
<211> LENGTH: 126
<212> TYPE: PRT
<213> ORGANISM: Artificial Sequence
<220> FEATURE:
<223> OTHER INFORMATION: Nanobody Nb_Syn1b

<400> SEQUENCE: 22

```
Asp Val Gln Leu Val Glu Ser Gly Gly Gly Ser Val Gln Ala Gly Gly
1               5                   10                  15
Ser Leu Arg Leu Ser Cys Ala Pro Ser Gly Leu Asn Ala Ser Ser Tyr
            20                  25                  30
Cys Met Gly Trp Phe Arg Gln Ser Pro Gly Lys Glu Arg Glu Gly Val
        35                  40                  45
Ala Arg Ile Asn Gly Asn Ala Gly Ile Lys Thr Ala Tyr Ala Asp Ser
    50                  55                  60
Val Lys Asp Arg Phe Thr Leu Ser Arg Asp Asn Ala Lys Asn Thr Val
65                  70                  75                  80
Tyr Leu Gln Met Asn Ser Leu Lys Ala Glu Asp Ser Ala Met Tyr Tyr
                85                  90                  95
Cys Ala Ala Lys Ser Ser Pro Gly Tyr Cys Gly Gly Asn Trp Asp Asn
            100                 105                 110
Phe Gly Tyr Trp Gly Gln Gly Thr Gln Val Thr Val Ser Ser
        115                 120                 125
```

<210> SEQ ID NO 23
<211> LENGTH: 126
<212> TYPE: PRT
<213> ORGANISM: Artificial Sequence
<220> FEATURE:
<223> OTHER INFORMATION: Nb_Syn1c

<400> SEQUENCE: 23

```
Gln Val Gln Leu Val Glu Ser Gly Gly Gly Ser Val Gln Ala Gly Gly
1               5                   10                  15
Ser Leu Arg Leu Ser Cys Ala Pro Leu Gly Leu Asn Ala Ser Ser Tyr
            20                  25                  30
Cys Met Gly Trp Phe Arg Gln Ser Pro Gly Lys Glu Arg Glu Gly Val
        35                  40                  45
Ala Arg Ile Asn Gly Asn Ala Gly Ile Lys Thr Ala Tyr Ala Asp Ser
    50                  55                  60
Val Lys Asp Arg Phe Thr Leu Ser Arg Asp Asn Ala Lys Asn Thr Val
65                  70                  75                  80
Tyr Leu Gln Met Asn Ser Leu Lys Ala Glu Asp Ser Ala Met Tyr Tyr
                85                  90                  95
Cys Ala Ala Lys Ser Ser Pro Gly Tyr Cys Gly Gly Asn Trp Asp Asn
            100                 105                 110
Phe Gly Tyr Trp Gly Gln Gly Thr Gln Val Thr Val Ser Ser
        115                 120                 125
```

<210> SEQ ID NO 24
<211> LENGTH: 126
<212> TYPE: PRT
<213> ORGANISM: Artificial Sequence
<220> FEATURE:
<223> OTHER INFORMATION: Nb_Syn1a

<400> SEQUENCE: 24

-continued

Glu Val Gln Leu Val Glu Ser Gly Gly Ser Val Gln Ala Gly Gly
1               5                   10                  15

Ser Leu Ser Leu Ala Cys Ala Pro Ser Gly Leu Asn Ala Ser Ser Tyr
            20                  25                  30

Cys Met Gly Trp Phe Arg Gln Ser Pro Gly Lys Glu Arg Glu Gly Val
        35                  40                  45

Ala Arg Ile Asn Gly Asn Ala Gly Ile Lys Thr Ala Tyr Ala Asp Ser
    50                  55                  60

Val Lys Asp Arg Phe Thr Leu Ser Arg Asp Asn Ala Lys Asn Thr Val
65                  70                  75                  80

Tyr Leu Gln Met Asn Ser Leu Lys Ala Glu Asp Ser Ala Ile Tyr Phe
                85                  90                  95

Cys Ala Ala Lys Ser Ser Pro Gly Tyr Cys Gly Gly Asn Trp Asp Asn
            100                 105                 110

Phe Gly Tyr Trp Gly Gln Gly Thr Gln Val Thr Val Ser Ser
            115                 120                 125

<210> SEQ ID NO 25
<211> LENGTH: 124
<212> TYPE: PRT
<213> ORGANISM: Artificial Sequence
<220> FEATURE:
<223> OTHER INFORMATION: Nb_86

<400> SEQUENCE: 25

Gln Val Gln Leu Gln Glu Ser Gly Gly Gly Ser Val Gln Ala Gly Gly
1               5                   10                  15

Ser Leu Arg Leu Ser Cys Ala Leu Ser Gly Tyr Thr Phe Arg Gly Asn
            20                  25                  30

Arg Met Ala Trp Phe Arg Gln Ala Pro Gly Lys Glu Arg Glu Gly Val
        35                  40                  45

Ala Arg Ile Asn Thr Gly Gly Val Asn Thr Tyr Val Ala Asp Ser Val
    50                  55                  60

Lys Gly Arg Phe Thr Ile Ser Gln Asp Asn Ala Lys Asn Thr Val Tyr
65                  70                  75                  80

Leu Gln Met Asn Asn Leu Gln Pro Glu Asp Thr Ala Met Tyr Phe Cys
                85                  90                  95

Ala Ala Asp Leu Thr Gly Trp Arg Pro Val Gly Phe Ser Gly Tyr Asn
            100                 105                 110

Tyr Trp Gly Gln Gly Thr Gln Val Thr Val Ser Ser
            115                 120

<210> SEQ ID NO 26
<211> LENGTH: 122
<212> TYPE: PRT
<213> ORGANISM: Artificial Sequence
<220> FEATURE:
<223> OTHER INFORMATION: Nb_87

<400> SEQUENCE: 26

Gln Val Gln Leu Gln Glu Ser Gly Gly Gly Ser Val Gln Thr Gly Gly
1               5                   10                  15

Ser Leu Arg Leu Ser Cys Val Ala Ser Gly Tyr Ser Tyr Met Ala
            20                  25                  30

Trp Phe Arg Gln Ala Pro Gly Lys Glu Arg Glu Gly Ile Ala Ala Ile
        35                  40                  45

Tyr Arg Gly Asp Lys Ile Thr Tyr Tyr Ala His Ser Val Gln Gly Arg
    50                  55                  60

```
Phe Thr Ile Ser Gln Ala Asn Ala Lys Asn Thr Val Tyr Leu Leu Met
 65                  70                  75                  80

Asn Ser Leu Lys Pro Glu Asp Thr Ala Ile Tyr Tyr Cys Ala Ala Arg
                 85                  90                  95

Arg Val Val Ala Asp Ser Pro Leu Leu Ser Lys Thr Tyr Ala Tyr Trp
            100                 105                 110

Gly Gln Gly Thr Gln Val Thr Val Ser Ser
        115                 120

<210> SEQ ID NO 27
<211> LENGTH: 8
<212> TYPE: PRT
<213> ORGANISM: Artificial Sequence
<220> FEATURE:
<223> OTHER INFORMATION: CDR

<400> SEQUENCE: 27

Gly Leu Thr Tyr Ser Asn Tyr Cys
1               5

<210> SEQ ID NO 28
<211> LENGTH: 8
<212> TYPE: PRT
<213> ORGANISM: Artificial Sequence
<220> FEATURE:
<223> OTHER INFORMATION: CDR

<400> SEQUENCE: 28

Ile Ser Thr Arg Gly Ile Lys Thr
1               5

<210> SEQ ID NO 29
<211> LENGTH: 20
<212> TYPE: PRT
<213> ORGANISM: Artificial Sequence
<220> FEATURE:
<223> OTHER INFORMATION: CDR

<400> SEQUENCE: 29

Ala Ala Val Ile Tyr Pro Gly Tyr Gly Asp Ser Cys Pro Trp Thr Thr
1               5                   10                  15

Ser Val Asn Tyr
            20

<210> SEQ ID NO 30
<211> LENGTH: 8
<212> TYPE: PRT
<213> ORGANISM: Artificial Sequence
<220> FEATURE:
<223> OTHER INFORMATION: CDR

<400> SEQUENCE: 30

Gly Tyr Thr Tyr Ser Arg Ile Cys
1               5

<210> SEQ ID NO 31
<211> LENGTH: 8
<212> TYPE: PRT
<213> ORGANISM: Artificial Sequence
<220> FEATURE:
<223> OTHER INFORMATION: CDR

<400> SEQUENCE: 31

Gly Ile Asp Ser Ser Ser Tyr Cys
```

```
<210> SEQ ID NO 32
<211> LENGTH: 9
<212> TYPE: PRT
<213> ORGANISM: Artificial Sequence
<220> FEATURE:
<223> OTHER INFORMATION: CDR

<400> SEQUENCE: 32

Ile Asn Gly Leu Gly Gly Val Lys Thr
1               5

<210> SEQ ID NO 33
<211> LENGTH: 18
<212> TYPE: PRT
<213> ORGANISM: Artificial Sequence
<220> FEATURE:
<223> OTHER INFORMATION: CDR

<400> SEQUENCE: 33

Ala Ala Lys Phe Ser Pro Gly Tyr Cys Gly Gly Ser Trp Ser Asn Phe
1               5                   10                  15

Gly Tyr

<210> SEQ ID NO 34
<211> LENGTH: 8
<212> TYPE: PRT
<213> ORGANISM: Artificial Sequence
<220> FEATURE:
<223> OTHER INFORMATION: CDR

<400> SEQUENCE: 34

Gly Leu Asn Ala Ser Ser Tyr Cys
1               5

<210> SEQ ID NO 35
<211> LENGTH: 9
<212> TYPE: PRT
<213> ORGANISM: Artificial Sequence
<220> FEATURE:
<223> OTHER INFORMATION: CDR

<400> SEQUENCE: 35

Ile Asn Gly Asn Ala Gly Ile Lys Thr
1               5

<210> SEQ ID NO 36
<211> LENGTH: 18
<212> TYPE: PRT
<213> ORGANISM: Artificial Sequence
<220> FEATURE:
<223> OTHER INFORMATION: CDR

<400> SEQUENCE: 36

Ala Ala Lys Ser Ser Pro Gly Tyr Cys Gly Gly Asn Trp Asp Asn Phe
1               5                   10                  15

Gly Tyr

<210> SEQ ID NO 37
<211> LENGTH: 8
<212> TYPE: PRT
<213> ORGANISM: Artificial Sequence
<220> FEATURE:
<223> OTHER INFORMATION: CDR
```

```
<400> SEQUENCE: 37

Gly Tyr Thr Phe Arg Gly Asn Arg
1               5

<210> SEQ ID NO 38
<211> LENGTH: 8
<212> TYPE: PRT
<213> ORGANISM: Artificial Sequence
<220> FEATURE:
<223> OTHER INFORMATION: CDR

<400> SEQUENCE: 38

Ile Asn Thr Gly Gly Val Asn Thr
1               5

<210> SEQ ID NO 39
<211> LENGTH: 17
<212> TYPE: PRT
<213> ORGANISM: Artificial Sequence
<220> FEATURE:
<223> OTHER INFORMATION: CDR

<400> SEQUENCE: 39

Ala Ala Asp Leu Thr Gly Trp Arg Pro Val Gly Phe Ser Gly Tyr Asn
1               5                   10                  15

Tyr

<210> SEQ ID NO 40
<211> LENGTH: 5
<212> TYPE: PRT
<213> ORGANISM: Artificial Sequence
<220> FEATURE:
<223> OTHER INFORMATION: CDR

<400> SEQUENCE: 40

Gly Tyr Ser Gly Tyr
1               5

<210> SEQ ID NO 41
<211> LENGTH: 8
<212> TYPE: PRT
<213> ORGANISM: Artificial Sequence
<220> FEATURE:
<223> OTHER INFORMATION: CDR

<400> SEQUENCE: 41

Ile Tyr Arg Gly Asp Lys Ile Thr
1               5

<210> SEQ ID NO 42
<211> LENGTH: 18
<212> TYPE: PRT
<213> ORGANISM: Artificial Sequence
<220> FEATURE:
<223> OTHER INFORMATION: CDR

<400> SEQUENCE: 42

Ala Ala Arg Arg Val Val Ala Asp Ser Pro Leu Leu Ser Lys Thr Tyr
1               5                   10                  15

Ala Tyr

<210> SEQ ID NO 43
<211> LENGTH: 29
<212> TYPE: DNA
<213> ORGANISM: Artificial Sequence
```

-continued

```
<220> FEATURE:
<223> OTHER INFORMATION: Primer

<400> SEQUENCE: 43
gatgtgcagc tgcaggagtc tggrggagg                                29

<210> SEQ ID NO 44
<211> LENGTH: 54
<212> TYPE: DNA
<213> ORGANISM: Artificial Sequence
<220> FEATURE:
<223> OTHER INFORMATION: Primer

<400> SEQUENCE: 44
gtagcggccg ctggggtctt cggggtggtg cgctgaggag acggtgacct gggt    54

<210> SEQ ID NO 45
<211> LENGTH: 54
<212> TYPE: DNA
<213> ORGANISM: Artificial Sequence
<220> FEATURE:
<223> OTHER INFORMATION: Primer

<400> SEQUENCE: 45
gtagcggccg cttggttggg gtatcttggg ttctgaggag acggtgacct gggt    54

<210> SEQ ID NO 46
<211> LENGTH: 48
<212> TYPE: DNA
<213> ORGANISM: Artificial Sequence
<220> FEATURE:
<223> OTHER INFORMATION: Primer

<400> SEQUENCE: 46
gtagcggccg cttacttcat tcgttcctga ggagacggtg acctgggt          48

<210> SEQ ID NO 47
<211> LENGTH: 53
<212> TYPE: DNA
<213> ORGANISM: Artificial Sequence
<220> FEATURE:
<223> OTHER INFORMATION: Primer

<400> SEQUENCE: 47
gtcaccgtct cctcacacca ccatcaccat cacgaacctg aagcctagta ccc     53

<210> SEQ ID NO 48
<211> LENGTH: 52
<212> TYPE: DNA
<213> ORGANISM: Artificial Sequence
<220> FEATURE:
<223> OTHER INFORMATION: Primer

<400> SEQUENCE: 48
gtacgggtac taggcttcag gttcgtgatg gtgatggtgg tgtgaggaga cg      52

<210> SEQ ID NO 49
<211> LENGTH: 60
<212> TYPE: DNA
<213> ORGANISM: Artificial Sequence
<220> FEATURE:
<223> OTHER INFORMATION: Primer

<400> SEQUENCE: 49
ttcgaattca ttacgcttcc ggttcataat cctgatatcc tttgtagagc tcatccatgc  60
```

<210> SEQ ID NO 50
<211> LENGTH: 58
<212> TYPE: DNA
<213> ORGANISM: Artificial Sequence
<220> FEATURE:
<223> OTHER INFORMATION: Primer

<400> SEQUENCE: 50
ttcgaattca ttacgcttcc ggttcataat cctgatattt gtagagctca tccatgcc            58

<210> SEQ ID NO 51
<211> LENGTH: 55
<212> TYPE: DNA
<213> ORGANISM: Artificial Sequence
<220> FEATURE:
<223> OTHER INFORMATION: Primer

<400> SEQUENCE: 51
ttcgaattca ttacgcttcc ggttcataat cctgtttgta gagctcatcc atgcc               55

<210> SEQ ID NO 52
<211> LENGTH: 31
<212> TYPE: DNA
<213> ORGANISM: Artificial Sequence
<220> FEATURE:
<223> OTHER INFORMATION: Primer

<400> SEQUENCE: 52
ttcgaattca ttattccggt tcataatcct g                                         31

<210> SEQ ID NO 53
<211> LENGTH: 65
<212> TYPE: DNA
<213> ORGANISM: Artificial Sequence
<220> FEATURE:
<223> OTHER INFORMATION: Primer

<400> SEQUENCE: 53
acccaggtca ccgtctcctc agggtatcaa gactacgaac ctgaagccta gtacccgtac         60
gacgt                                                                     65

<210> SEQ ID NO 54
<211> LENGTH: 24
<212> TYPE: DNA
<213> ORGANISM: Artificial Sequence
<220> FEATURE:
<223> OTHER INFORMATION: Primer

<400> SEQUENCE: 54
cgccagggtt ttcccagtca cgac                                                 24

<210> SEQ ID NO 55
<211> LENGTH: 61
<212> TYPE: DNA
<213> ORGANISM: Artificial Sequence
<220> FEATURE:
<223> OTHER INFORMATION: Primer

<400> SEQUENCE: 55
acccaggtca ccgtctcctc aggggcagcg gaacctgaag cctagtaccc gtacgacgtt         60
c                                                                         61

<210> SEQ ID NO 56
<211> LENGTH: 20

```
<212> TYPE: DNA
<213> ORGANISM: Artificial Sequence
<220> FEATURE:
<223> OTHER INFORMATION: Primer

<400> SEQUENCE: 56
ttatgcttcc ggctcgtatg                                              20

<210> SEQ ID NO 57
<211> LENGTH: 19
<212> TYPE: DNA
<213> ORGANISM: Artificial Sequence
<220> FEATURE:
<223> OTHER INFORMATION: Primer

<400> SEQUENCE: 57
ccacagacag ccctcatag                                               19

<210> SEQ ID NO 58
<211> LENGTH: 21
<212> TYPE: DNA
<213> ORGANISM: Artificial Sequence
<220> FEATURE:
<223> OTHER INFORMATION: Primer

<400> SEQUENCE: 58
tgaggagacg gtgacctggg t                                            21

<210> SEQ ID NO 59
<211> LENGTH: 21
<212> TYPE: DNA
<213> ORGANISM: Artificial Sequence
<220> FEATURE:
<223> OTHER INFORMATION: Primer

<400> SEQUENCE: 59
attaatacga ctcactatag g                                            21

<210> SEQ ID NO 60
<211> LENGTH: 63
<212> TYPE: DNA
<213> ORGANISM: Artificial Sequence
<220> FEATURE:
<223> OTHER INFORMATION: Primer

<400> SEQUENCE: 60
tcgagcggcc gcttaggctt caggttcgta gtcttgatac cctgaagctc ctgcaccatt   60
ctc                                                                63

<210> SEQ ID NO 61
<211> LENGTH: 45
<212> TYPE: DNA
<213> ORGANISM: Artificial Sequence
<220> FEATURE:
<223> OTHER INFORMATION: Primer

<400> SEQUENCE: 61
tcgagcggcc gcttaggctt caggttcagc tcctgcacca ttctc                  45

<210> SEQ ID NO 62
<211> LENGTH: 31
<212> TYPE: DNA
<213> ORGANISM: Artificial Sequence
<220> FEATURE:
<223> OTHER INFORMATION: Primer
```

```
<400> SEQUENCE: 62
gcttggtacc tcatgagcaa aggagaagaa c                                31

<210> SEQ ID NO 63
<211> LENGTH: 60
<212> TYPE: DNA
<213> ORGANISM: Artificial Sequence
<220> FEATURE:
<223> OTHER INFORMATION: Primer

<400> SEQUENCE: 63
ttcgaattca ttacgcttcc ggttcataat cctgatatcc tttgtagagc tcatccatgc    60

<210> SEQ ID NO 64
<211> LENGTH: 55
<212> TYPE: DNA
<213> ORGANISM: Artificial Sequence
<220> FEATURE:
<223> OTHER INFORMATION: Primer

<400> SEQUENCE: 64
ttcgaattca ttacgcttcc ggttctgcgg ctcctttgta gagctcatcc atgcc         55

<210> SEQ ID NO 65
<211> LENGTH: 115
<212> TYPE: PRT
<213> ORGANISM: Artificial Sequence
<220> FEATURE:
<223> OTHER INFORMATION: Nanobody Nb_196

<400> SEQUENCE: 65

Gln Val Gln Leu Gln Val Ser Gly Gly Gly Leu Val Gln Pro Gly Gly
 1               5                  10                  15

Ser Leu Arg Leu Ser Cys Ala Ala Ser Gly Phe Thr Val Ser Asn Ser
            20                  25                  30

Arg Met Tyr Trp Val Arg Gln Ala Pro Gly Lys Gly Leu Glu Trp Val
        35                  40                  45

Ser Ser Ile Arg Pro Ser Gly Glu Val Ile Tyr Ala Thr Asp Ser Val
    50                  55                  60

Lys Gly Arg Phe Ile Ile Ser Arg Asp Asn Ala Lys Asn Thr Leu His
65                  70                  75                  80

Leu Gln Met Asn Ser Leu Lys Pro Glu Asp Thr Ala Arg Tyr Tyr Cys
                85                  90                  95

Ala Arg Glu Arg Pro Ser Gly Val Arg Gly Gln Gly Thr Gln Val Thr
            100                 105                 110

Val Ser Ser
        115

<210> SEQ ID NO 66
<211> LENGTH: 126
<212> TYPE: PRT
<213> ORGANISM: Artificial Sequence
<220> FEATURE:
<223> OTHER INFORMATION: Nanobody Nb_458

<400> SEQUENCE: 66

Gln Val Gln Leu Gln Glu Ser Gly Gly Gly Val Val Gln Ala Gly Gly
 1               5                  10                  15

Ser Leu Arg Leu Ser Cys Ala Ala Pro Gly Leu Ser Phe Ser Asn Tyr
            20                  25                  30

Ile Met Gly Trp Phe Arg Gln Ala Pro Gly Lys Ala Arg Glu Phe Val
```

```
            35                  40                  45

Ala Ala Ile Ser Trp Asn Gly Gly Glu Thr Asn Tyr Val Asp Ser Ala
         50                  55                  60

Lys Gly Arg Phe Thr Ile Ser Arg Asp Asn Ala Lys Asn Thr Val Tyr
 65                  70                  75                  80

Leu Gln Met Ser Ser Leu Lys Ser Glu Asp Thr Ala Val Tyr Tyr Cys
                 85                  90                  95

Ala Ala Asp Tyr Arg Ser Phe Ser Asn Pro Asp Ser Asp Pro Ser Arg
            100                 105                 110

Tyr Ala Tyr Trp Gly Gln Gly Thr Gln Val Thr Val Ser Ser
            115                 120                 125

<210> SEQ ID NO 67
<211> LENGTH: 31
<212> TYPE: DNA
<213> ORGANISM: Artificial Sequence
<220> FEATURE:
<223> OTHER INFORMATION: Primer

<400> SEQUENCE: 67
taatcatgag caaaggagaa gaactttcca c                            31

<210> SEQ ID NO 68
<211> LENGTH: 267
<212> TYPE: PRT
<213> ORGANISM: Artificial Sequence
<220> FEATURE:
<223> OTHER INFORMATION: Nanobody biNbSyn2

<400> SEQUENCE: 68

Gln Val Gln Leu Val Glu Ser Gly Gly Gly Ser Val Gln Ala Gly Gly
  1               5                  10                  15

Ser Leu Arg Leu Ser Cys Ala Ala Ser Gly Ile Asp Ser Ser Ser Tyr
             20                  25                  30

Cys Met Gly Trp Phe Arg Gln Arg Pro Gly Lys Glu Arg Glu Gly Val
             35                  40                  45

Ala Arg Ile Asn Gly Leu Gly Gly Val Lys Thr Ala Tyr Ala Asp Ser
         50                  55                  60

Val Lys Asp Arg Phe Thr Ile Ser Arg Asp Asn Ala Glu Asn Thr Val
 65                  70                  75                  80

Tyr Leu Gln Met Asn Ser Leu Lys Pro Glu Asp Thr Ala Ile Tyr Tyr
                 85                  90                  95

Cys Ala Ala Lys Phe Ser Pro Gly Tyr Cys Gly Gly Ser Trp Ser Asn
            100                 105                 110

Phe Gly Tyr Trp Gly Gln Gly Thr Gln Val Thr Val Ser Ser Gly Gly
            115                 120                 125

Gly Gly Ser Gly Gly Gly Ser Gln Val Gln Leu Gln Glu Ser Gly Gly
            130                 135                 140

Gly Ser Val Gln Ala Gly Gly Ser Leu Arg Leu Ser Cys Ala Ala Ser
145                 150                 155                 160

Gly Ile Asp Ser Ser Ser Tyr Cys Met Gly Trp Phe Arg Gln Arg Pro
            165                 170                 175

Gly Lys Glu Arg Glu Gly Val Ala Arg Ile Asn Gly Leu Gly Gly Val
            180                 185                 190

Lys Thr Ala Tyr Ala Asp Ser Val Lys Asp Arg Phe Thr Ile Ser Arg
            195                 200                 205

Asp Asn Ala Glu Asn Thr Val Tyr Leu Gln Met Asn Ser Leu Lys Pro
```

```
               210                 215                 220
Glu Asp Thr Ala Ile Tyr Tyr Cys Ala Ala Lys Phe Ser Pro Gly Tyr
225                 230                 235                 240

Cys Gly Gly Ser Trp Ser Asn Phe Gly Tyr Trp Gly Gln Gly Thr Gln
                245                 250                 255

Val Thr Val Ser Ser His His His His His
            260                 265
```

<210> SEQ ID NO 69
<211> LENGTH: 9
<212> TYPE: PRT
<213> ORGANISM: Artificial Sequence
<220> FEATURE:
<223> OTHER INFORMATION: Linker

<400> SEQUENCE: 69

```
Gly Gly Gly Gly Ser Gly Gly Gly Ser
1               5
```

<210> SEQ ID NO 70
<211> LENGTH: 6
<212> TYPE: PRT
<213> ORGANISM: Artificial Sequence
<220> FEATURE:
<223> OTHER INFORMATION: Tag

<400> SEQUENCE: 70

```
Gly Gly Glu Pro Glu Ala
1               5
```

<210> SEQ ID NO 71
<211> LENGTH: 5
<212> TYPE: PRT
<213> ORGANISM: Artificial Sequence
<220> FEATURE:
<223> OTHER INFORMATION: synthetic peptide

<400> SEQUENCE: 71

```
Ser Glu Pro Glu Ala
1               5
```

<210> SEQ ID NO 72
<211> LENGTH: 283
<212> TYPE: PRT
<213> ORGANISM: Artificial Sequence
<220> FEATURE:
<223> OTHER INFORMATION: EPEA tagged CsgG

<400> SEQUENCE: 72

```
Met Gln Arg Leu Phe Leu Leu Val Ala Val Met Leu Leu Ser Gly Cys
1               5                   10                  15

Leu Thr Ala Pro Pro Lys Glu Ala Ala Arg Pro Thr Leu Met Pro Arg
                20                  25                  30

Ala Gln Ser Tyr Lys Asp Leu Thr His Leu Pro Ala Pro Thr Gly Lys
            35                  40                  45

Ile Phe Val Ser Val Tyr Asn Ile Gln Asp Glu Thr Gly Gln Phe Lys
        50                  55                  60

Pro Tyr Pro Ala Ser Asn Phe Ser Thr Ala Val Pro Gln Ser Ala Thr
65                  70                  75                  80

Ala Met Leu Val Thr Ala Leu Lys Asp Ser Arg Trp Phe Ile Pro Leu
                85                  90                  95

Glu Arg Gln Gly Leu Gln Asn Leu Leu Asn Glu Arg Lys Ile Ile Arg
```

```
                100             105             110
Ala Ala Gln Glu Asn Gly Thr Val Ala Ile Asn Asn Arg Ile Pro Leu
        115                 120                 125

Gln Ser Leu Thr Ala Ala Asn Ile Met Val Glu Gly Ser Ile Ile Gly
    130                 135                 140

Tyr Glu Ser Asn Val Lys Ser Gly Gly Val Gly Ala Arg Tyr Phe Gly
145                 150                 155                 160

Ile Gly Ala Asp Thr Gln Tyr Gln Leu Asp Gln Ile Ala Val Asn Leu
                165                 170                 175

Arg Val Val Asn Val Ser Thr Gly Glu Ile Leu Ser Ser Val Asn Thr
                180                 185                 190

Ser Lys Thr Ile Leu Ser Tyr Glu Val Gln Ala Gly Val Phe Arg Phe
        195                 200                 205

Ile Asp Tyr Gln Arg Leu Leu Glu Gly Glu Val Gly Tyr Thr Ser Asn
        210                 215                 220

Glu Pro Val Met Leu Cys Leu Met Ser Ala Ile Glu Thr Gly Val Ile
225                 230                 235                 240

Phe Leu Ile Asn Asp Gly Ile Asp Arg Gly Leu Trp Asp Leu Gln Asn
                245                 250                 255

Lys Ala Glu Arg Gln Asn Asp Ile Leu Val Lys Tyr Arg His Met Ser
                260                 265                 270

Val Pro Pro Glu Ser Gly Gly Glu Pro Glu Ala
        275                 280

<210> SEQ ID NO 73
<211> LENGTH: 45
<212> TYPE: DNA
<213> ORGANISM: Artificial Sequence
<220> FEATURE:
<223> OTHER INFORMATION: Primer

<400> SEQUENCE: 73
cgcggcccag ccggccatgg ctgatgtgca gctggtggag tctgg              45

<210> SEQ ID NO 74
<211> LENGTH: 40
<212> TYPE: DNA
<213> ORGANISM: Artificial Sequence
<220> FEATURE:
<223> OTHER INFORMATION: Primer

<400> SEQUENCE: 74
agtaggatcc gccacctcct gaggagaccg tgacctgggt                    40

<210> SEQ ID NO 75
<211> LENGTH: 51
<212> TYPE: DNA
<213> ORGANISM: Artificial Sequence
<220> FEATURE:
<223> OTHER INFORMATION: Primer

<400> SEQUENCE: 75
tcttggatcc ggcggaggta gtcaggtgca gctgcaggag tctgggggag g        51

<210> SEQ ID NO 76
<211> LENGTH: 21
<212> TYPE: DNA
<213> ORGANISM: Artificial Sequence
<220> FEATURE:
<223> OTHER INFORMATION: Primer
```

```
<400> SEQUENCE: 76
tgaggagacg gtgacctggg t                                              21

<210> SEQ ID NO 77
<211> LENGTH: 43
<212> TYPE: DNA
<213> ORGANISM: Artificial Sequence
<220> FEATURE:
<223> OTHER INFORMATION: Primer

<400> SEQUENCE: 77
ggcggcgaac cggaagcgtg actgcaggca tgcaagcttg gct                      43

<210> SEQ ID NO 78
<211> LENGTH: 25
<212> TYPE: DNA
<213> ORGANISM: Artificial Sequence
<220> FEATURE:
<223> OTHER INFORMATION: Primer

<400> SEQUENCE: 78
tgactgcagg catgcaagct tggct                                          25

<210> SEQ ID NO 79
<211> LENGTH: 43
<212> TYPE: DNA
<213> ORGANISM: Artificial Sequence
<220> FEATURE:
<223> OTHER INFORMATION: Primer

<400> SEQUENCE: 79
cgcttccggt tcgccgccat ggtgatggtg atggtgggat tcc                      43

<210> SEQ ID NO 80
<211> LENGTH: 25
<212> TYPE: DNA
<213> ORGANISM: Artificial Sequence
<220> FEATURE:
<223> OTHER INFORMATION: Primer

<400> SEQUENCE: 80
atggtgatgg tgatggtggg attcc                                          25

<210> SEQ ID NO 81
<211> LENGTH: 5
<212> TYPE: PRT
<213> ORGANISM: Artificial Sequence
<220> FEATURE:
<223> OTHER INFORMATION: Linker

<400> SEQUENCE: 81

Gly Gly Gly Gly Ser
1               5
```